(12) United States Patent
Pappalardo et al.

(10) Patent No.: US 8,936,615 B2
(45) Date of Patent: Jan. 20, 2015

(54) BONE FIXATION SYSTEM INCLUDING K-WIRE COMPRESSION

(75) Inventors: Dana Pappalardo, West Chester, PA (US); Sherri Wykosky, West Chester, PA (US); Kenneth Kobayashi, West Chester, PA (US); Dipan Patel, West Chester, PA (US); William Kolb, Malvern, PA (US); Colleen Flesher, West Chester, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 457 days.

(21) Appl. No.: 13/095,339

(22) Filed: Apr. 27, 2011

(65) Prior Publication Data

US 2011/0264149 A1 Oct. 27, 2011

Related U.S. Application Data

(60) Provisional application No. 61/372,212, filed on Aug. 10, 2010, provisional application No. 61/328,278, filed on Apr. 27, 2010.

(51) Int. Cl.
*A61B 17/00* (2006.01)
*A61B 17/66* (2006.01)
(Continued)

(52) U.S. Cl.
CPC .......... *A61B 17/842* (2013.01); *A61B 17/8019* (2013.01); *A61B 17/8625* (2013.01); *A61B 17/863* (2013.01); *A61B 17/8635* (2013.01); *A61B 17/8866* (2013.01); *A61B 17/8057* (2013.01); *A61B 17/8061* (2013.01); *A61B 17/808* (2013.01); *A61B 17/848* (2013.01); *A61B 17/8861* (2013.01); *A61B 17/8014* (2013.01)

USPC ............ 606/207; 606/282; 606/105; 606/286

(58) Field of Classification Search
CPC .......................... A61B 17/282; A61B 17/8894
USPC ................ 606/90, 105, 207; 81/424.5, 426.5; 29/268

See application file for complete search history.

(56) References Cited

U.S. PATENT DOCUMENTS 1,649,423 A * 11/1927 Stieglitz ......................... 606/126
2,644,455 A * 7/1953 Benoit ........................... 606/205

(Continued)

FOREIGN PATENT DOCUMENTS

DE 7315277 8/1973
DE 20 2006-008031 10/2007

(Continued)

OTHER PUBLICATIONS

U.S. Appl. No. 61/328,278, filed Apr. 27, 2010, Kolb et al.

(Continued)

*Primary Examiner* — David Bates
(74) *Attorney, Agent, or Firm* — Baker & Hostetler LLP

(57) ABSTRACT

A bone fixation system includes a bone plate, bone anchors, temporary fixation members, and forceps. The temporary fixation members are configured to be inserted through apertures in the bone plate and into underlying bone segments that are separated by a bone gap. The forceps are configured to apply a force to the temporary fixation members that causes at least one of the underlying bone segments to translate with respect to the other bone segment, thereby reducing or distracting the bone segments without interfering with final fixation by screws of bone segments.

20 Claims, 33 Drawing Sheets

(51) Int. Cl.
  *A61B 17/58* (2006.01)
  *A61B 17/60* (2006.01)
  *A61F 2/00* (2006.01)
  *A61B 17/80* (2006.01)
  *A61B 17/84* (2006.01)
  *A61B 17/86* (2006.01)
  *A61B 17/88* (2006.01)

(56) References Cited

U.S. PATENT DOCUMENTS

| | | | |
|---|---|---|---|
| 2,977,150 A * | 3/1961 | Thomas | 294/118 |
| 3,209,753 A * | 10/1965 | Hawkins et al. | 606/207 |
| 3,647,186 A * | 3/1972 | Hartman | 254/248 |
| 4,024,870 A * | 5/1977 | Sandel | 606/207 |
| 4,192,313 A * | 3/1980 | Ogami | 606/207 |
| 4,844,068 A | 7/1989 | Arata et al. | |
| 4,887,612 A * | 12/1989 | Esser et al. | 600/564 |
| 5,147,369 A * | 9/1992 | Wagner | 606/107 |
| 5,281,223 A | 1/1994 | Ray | |
| 5,391,181 A * | 2/1995 | Johnson et al. | 606/207 |
| 5,562,447 A * | 10/1996 | Moy et al. | 433/150 |
| 5,624,454 A * | 4/1997 | Palti et al. | 606/151 |
| 5,693,069 A * | 12/1997 | Shallman | 606/205 |
| 5,697,933 A * | 12/1997 | Gundlapalli et al. | 606/96 |
| 5,746,757 A * | 5/1998 | McGuire | 606/148 |
| 5,891,161 A * | 4/1999 | Graser | 606/148 |
| 6,036,692 A | 3/2000 | Burel et al. | |
| 6,206,881 B1 | 3/2001 | Frigg et al. | |
| 6,306,136 B1 | 10/2001 | Baccelli | |
| 6,551,316 B1 | 4/2003 | Rinner et al. | |
| 6,660,006 B2 | 12/2003 | Markworth et al. | |
| 6,716,218 B2 | 4/2004 | Holmes et al. | |
| 6,746,449 B2 | 6/2004 | Jones et al. | |
| 7,044,947 B2 | 5/2006 | de la Torre et al. | |
| 7,210,378 B1 * | 5/2007 | Bibi | 81/9.4 |
| 7,326,218 B2 | 2/2008 | Sterett et al. | |
| 7,341,594 B2 | 3/2008 | Shluzas et al. | |
| 7,625,376 B2 | 12/2009 | Brumfield et al. | |
| 7,641,176 B2 * | 1/2010 | Clark et al. | 254/248 |
| 7,713,274 B2 | 5/2010 | Shluzas et al. | |
| 7,744,598 B2 | 6/2010 | Brumfield et al. | |
| 7,815,650 B2 | 10/2010 | Shluzas et al. | |
| 7,988,700 B2 | 8/2011 | Shluzas et al. | |
| 8,152,834 B2 * | 4/2012 | McGarity et al. | 606/205 |
| 8,647,120 B2 * | 2/2014 | Marteney et al. | 433/215 |
| 8,740,915 B2 | 6/2014 | Niederberger et al. | |
| 2005/0004590 A1 * | 1/2005 | Waters et al. | 606/170 |
| 2005/0191598 A1 * | 9/2005 | Anderson | 433/159 |
| 2006/0004380 A1 | 1/2006 | DiDomenico et al. | |
| 2007/0203492 A1 | 8/2007 | Needham et al. | |
| 2007/0244516 A1 * | 10/2007 | Chiu et al. | 606/207 |
| 2008/0140130 A1 | 6/2008 | Chan et al. | |
| 2008/0287995 A1 | 11/2008 | Gauthier | |
| 2009/0182345 A1 | 7/2009 | Medoff et al. | |
| 2009/0259262 A1 | 10/2009 | Nayet | |
| 2010/0016900 A1 | 1/2010 | Terres et al. | |
| 2010/0280560 A1 | 11/2010 | Brumfield et al. | |
| 2011/0098757 A1 | 4/2011 | Schelling | |
| 2011/0154958 A1 * | 6/2011 | Wang | 81/302 |
| 2011/0224734 A1 | 9/2011 | Schelling | |
| 2011/0264149 A1 | 10/2011 | Pappalardo et al. | |
| 2012/0197304 A1 | 8/2012 | Medoff et al. | |
| 2014/0214090 A1 | 7/2014 | Niederberger et al. | |

FOREIGN PATENT DOCUMENTS

| | | |
|---|---|---|
| EP | 1319372 | 6/2003 |
| EP | 1319372 B1 | 6/2003 |
| EP | 1923009 | 5/2008 |
| EP | 1923009 A3 | 6/2009 |
| WO | WO 96/24295 | 8/1996 |
| WO | WO 03/030395 | 4/2003 |
| WO | WO 2006/047581 | 5/2006 |
| WO | WO 2006/074792 | 7/2006 |
| WO | WO 2007/127994 | 11/2007 |
| WO | WO 2010/011477 | 1/2010 |
| WO | WO 2011/053520 | 5/2011 |
| WO | WO 2011/137163 | 11/2011 |
| WO | WO 2011/139740 | 11/2011 |

OTHER PUBLICATIONS

U.S. Appl. No. 61/372,212, filed Aug. 10, 2010, Kolb et al.
U.S. Appl. No. 61/328,347, filed Apr. 27, 2010, Neiderberger et al.
U.S. Appl. No. 61/328,381, filed Apr. 27, 2010, Neiderberger et al.

* cited by examiner

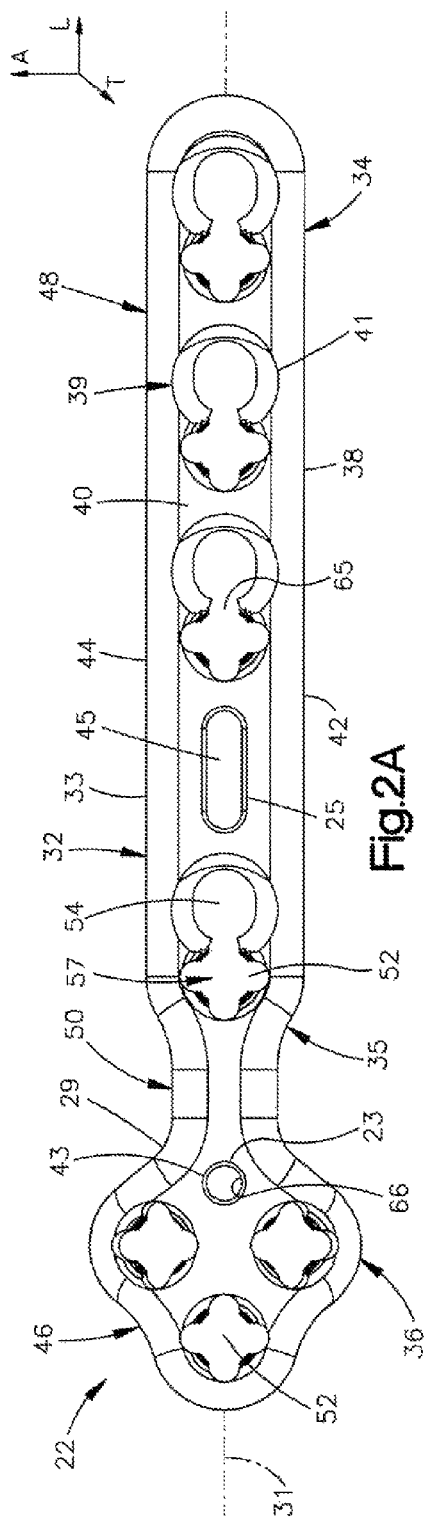
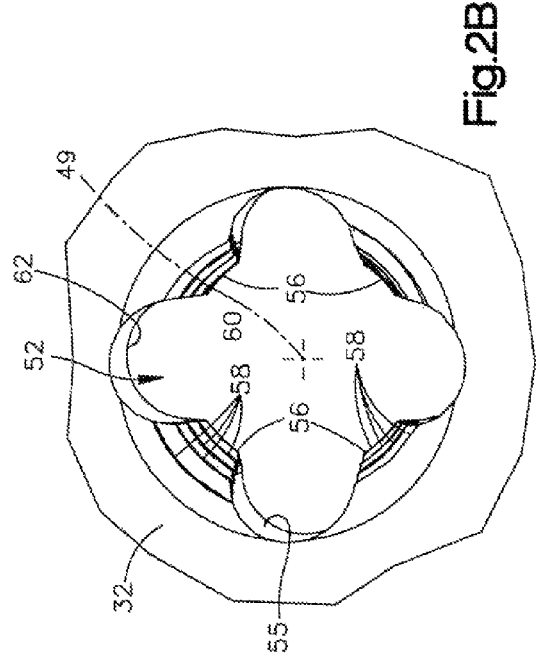

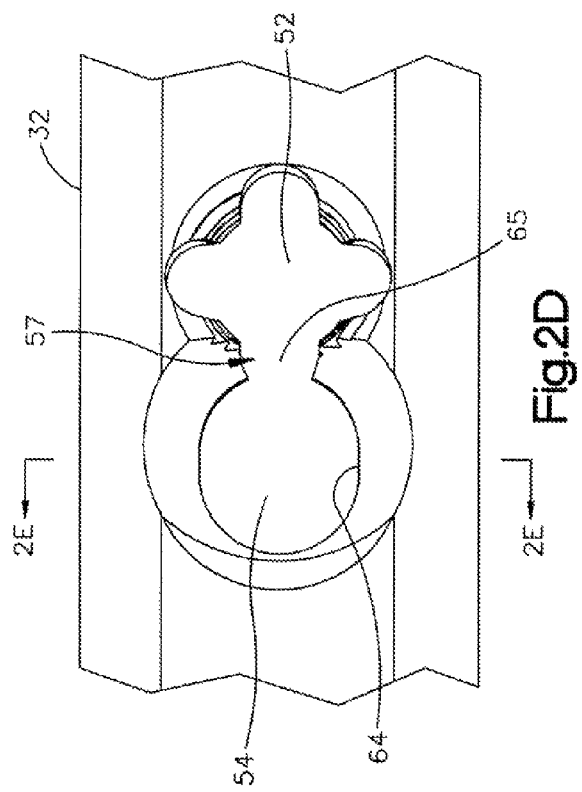
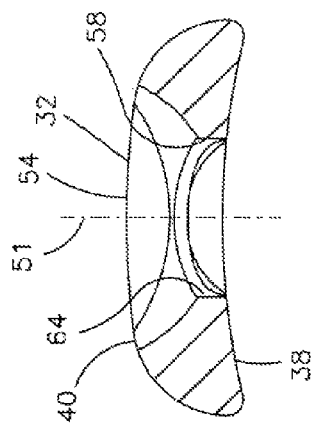
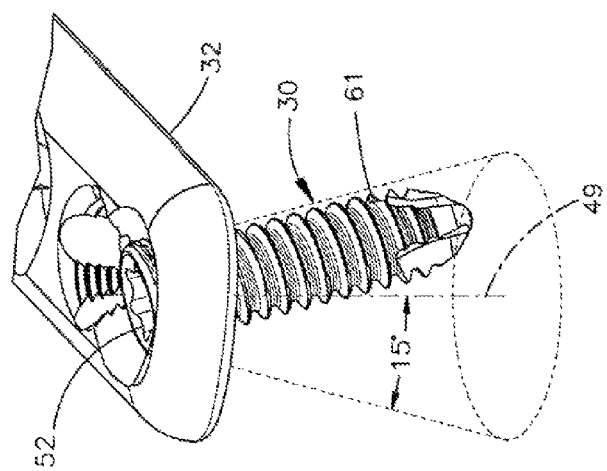

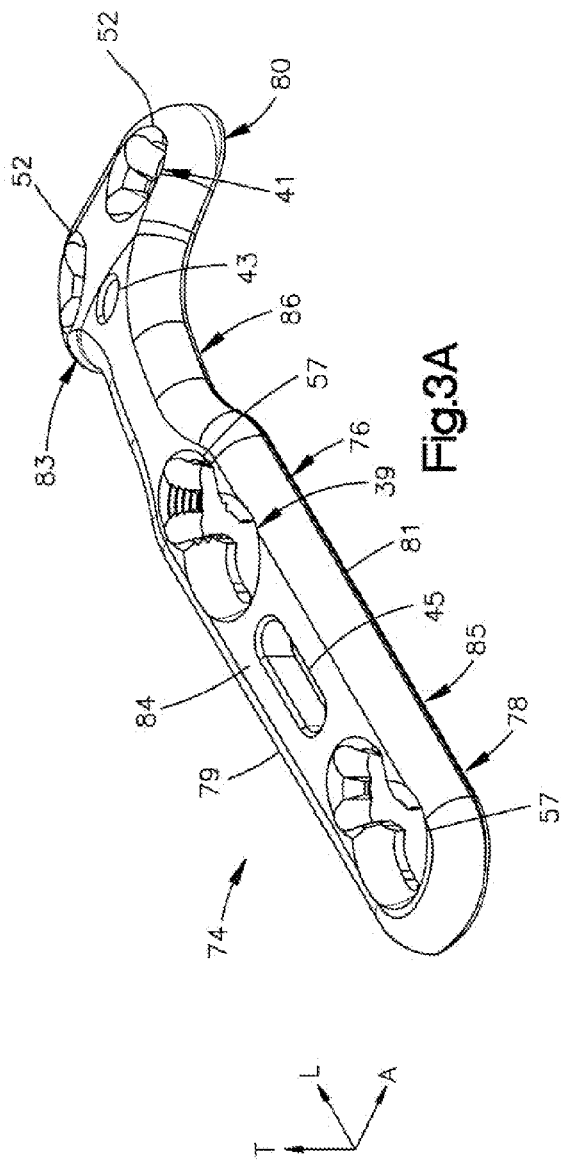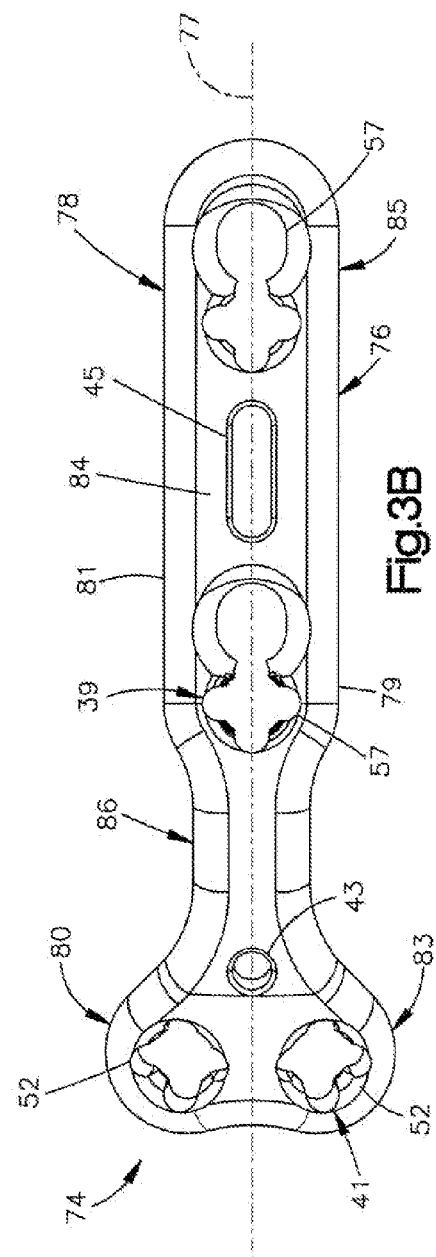

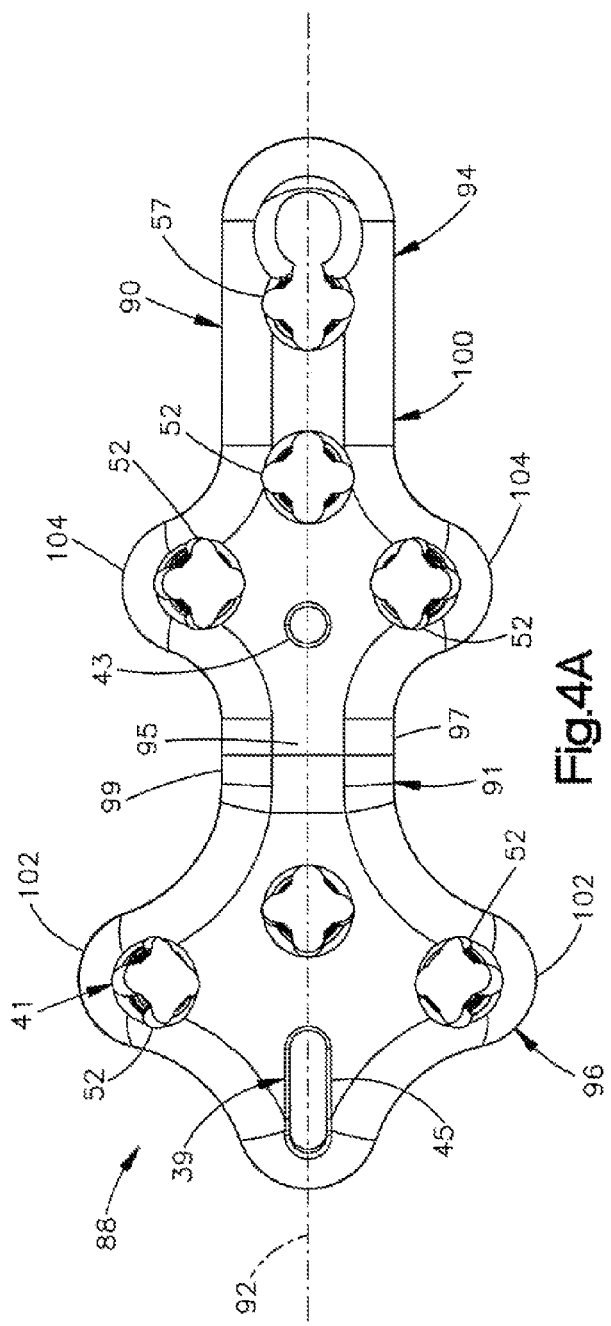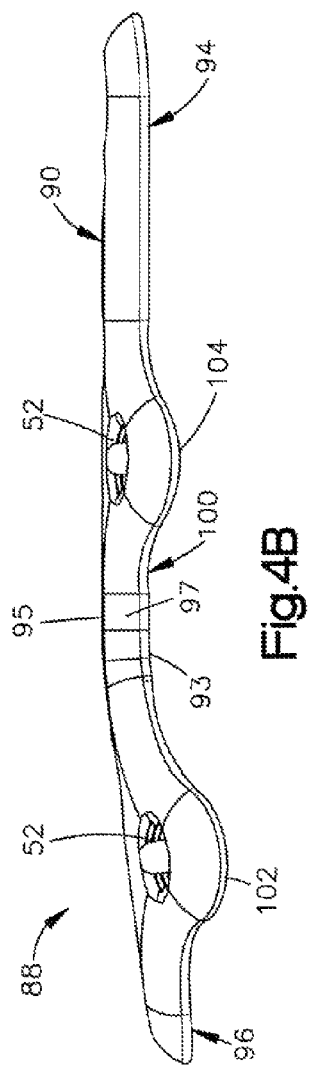

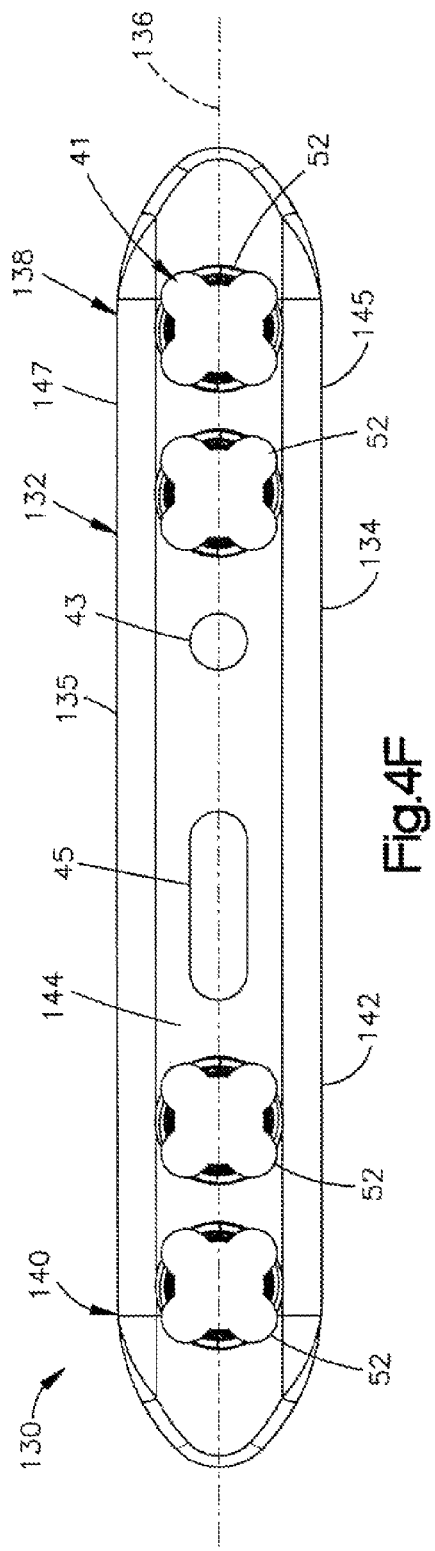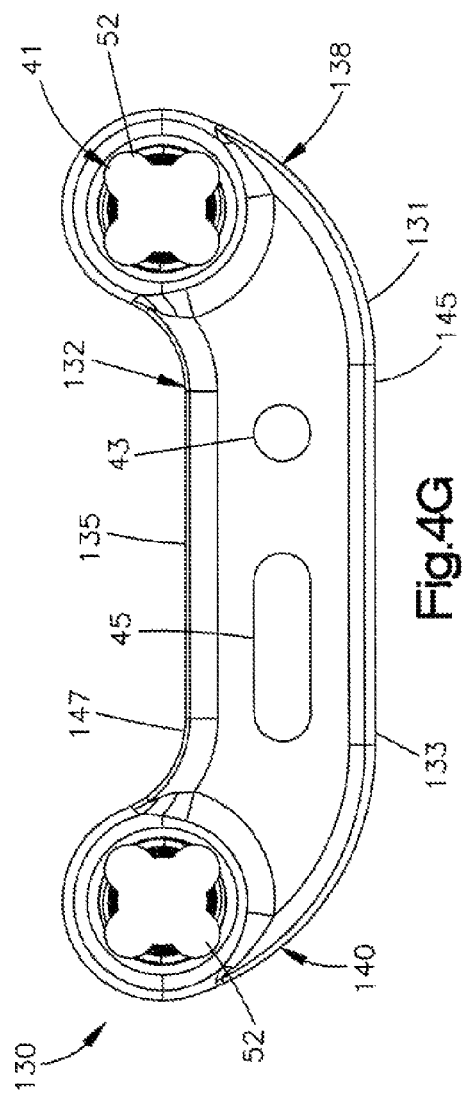

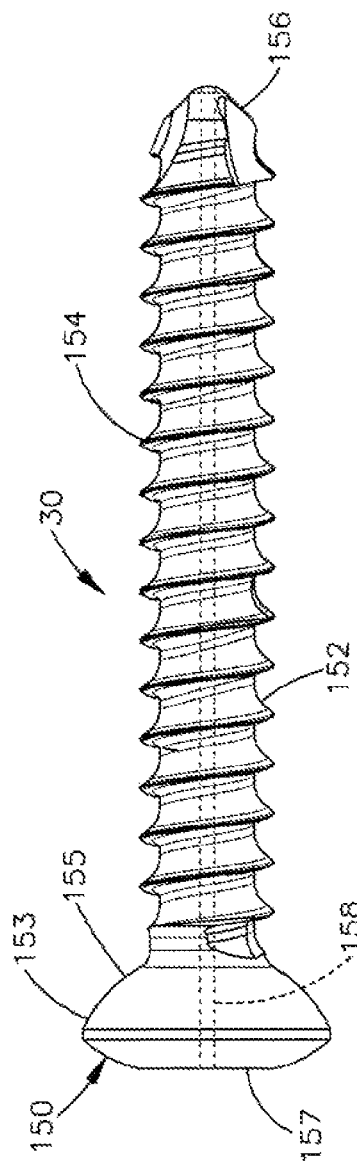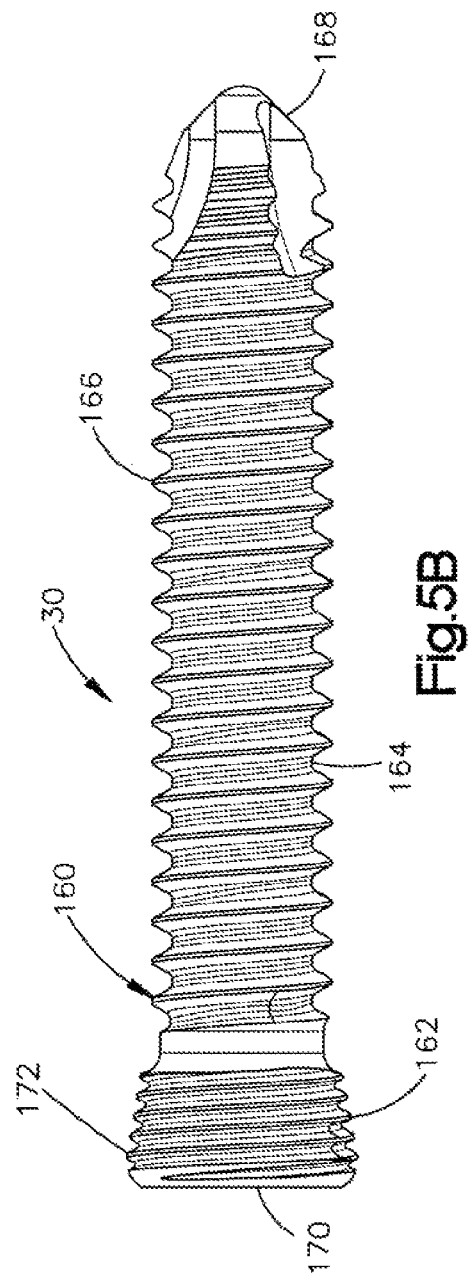

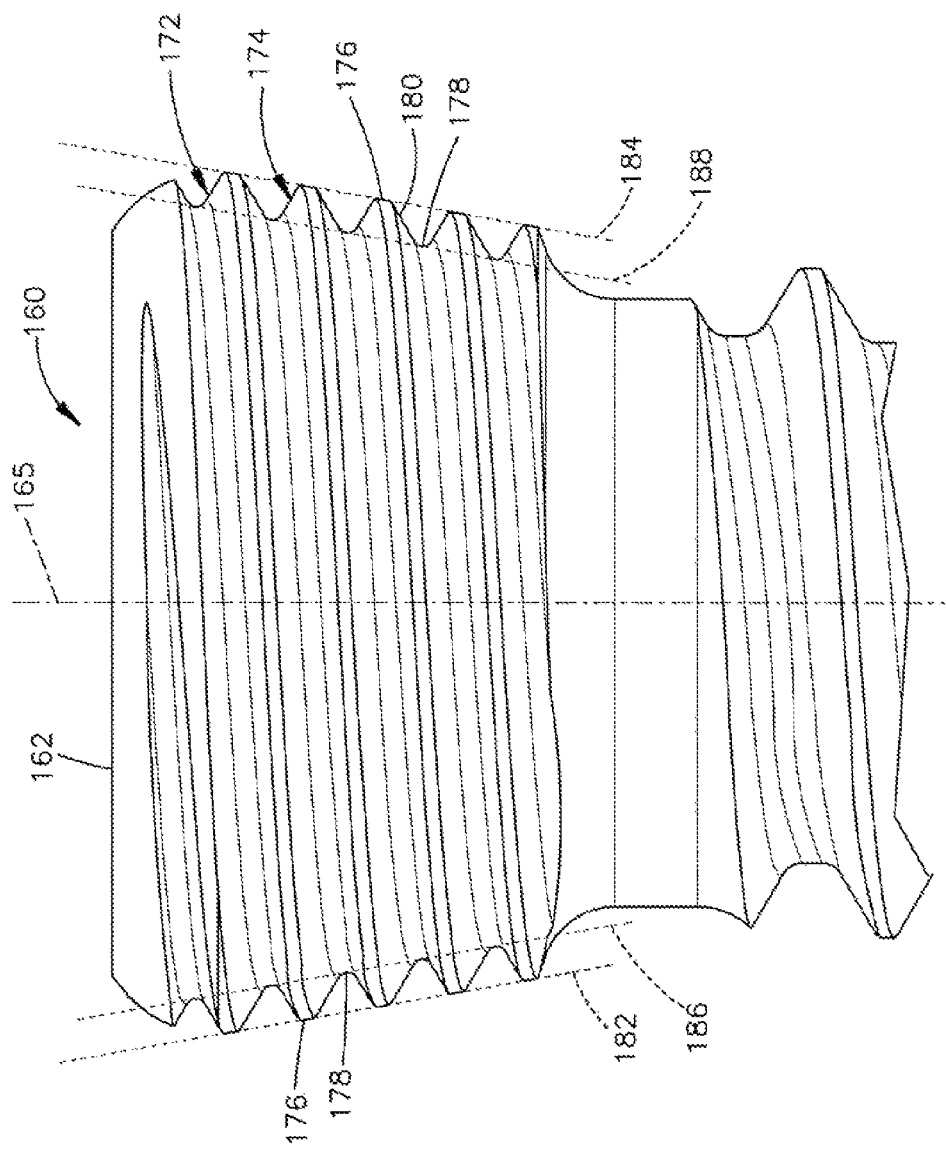

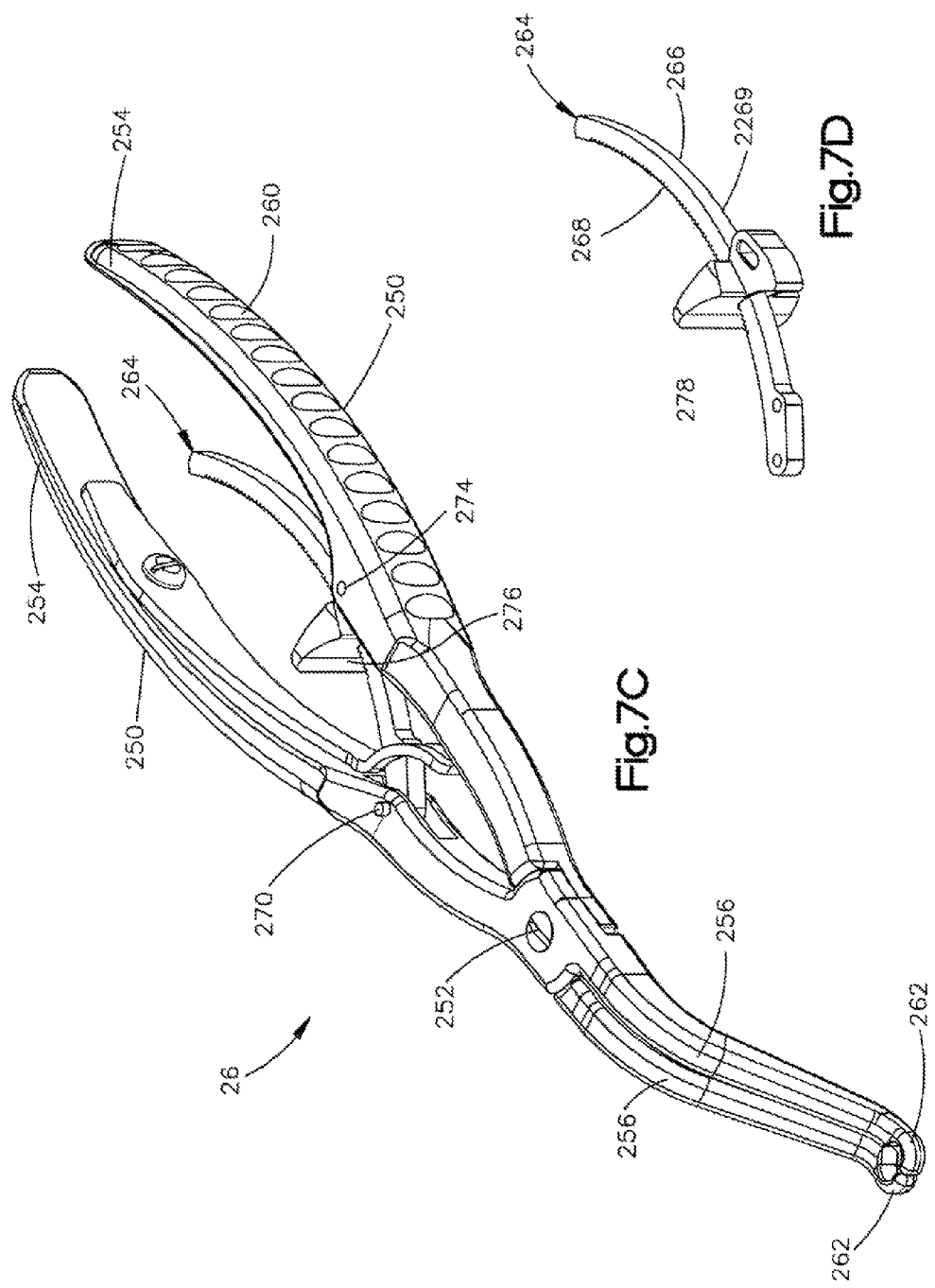

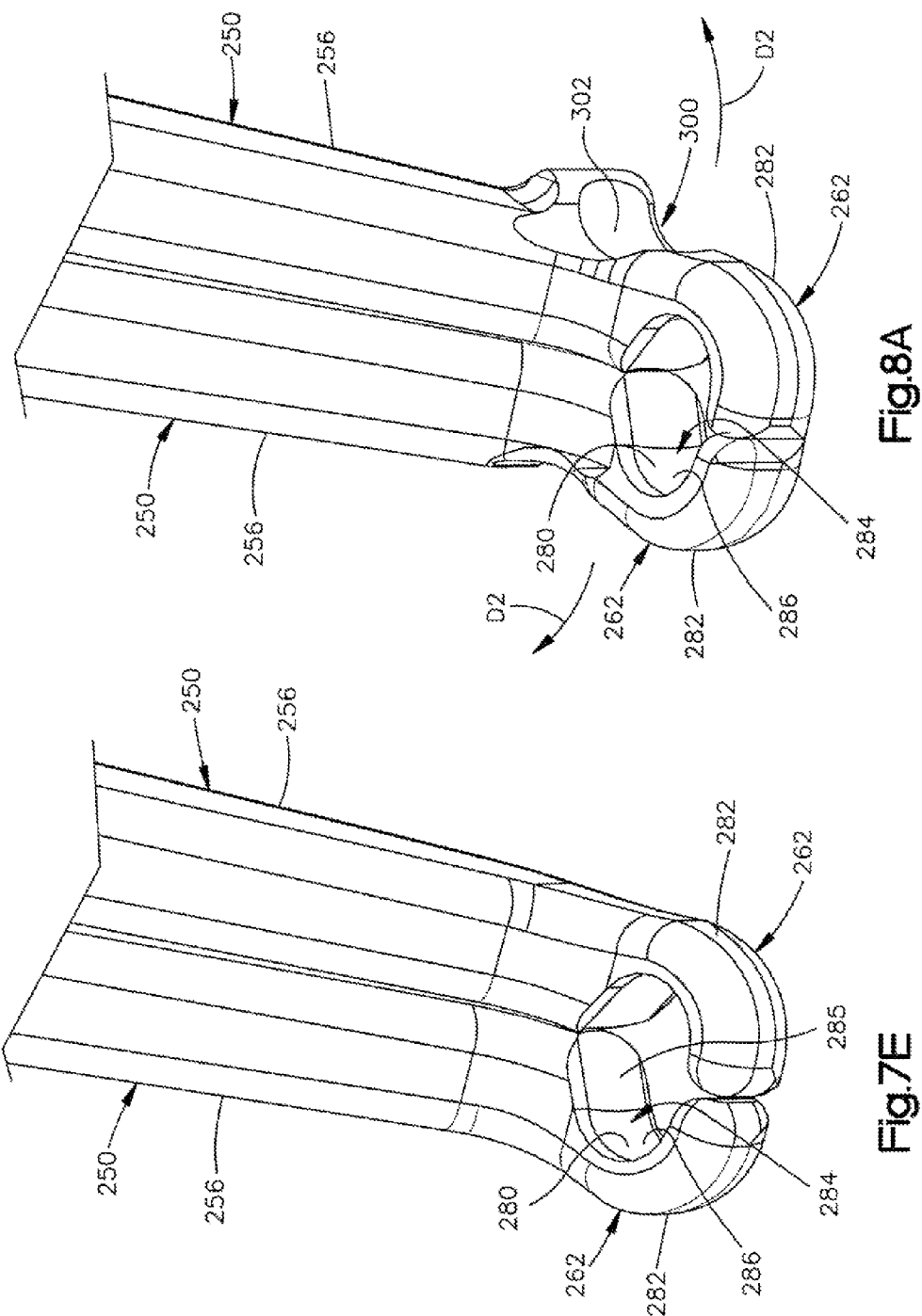

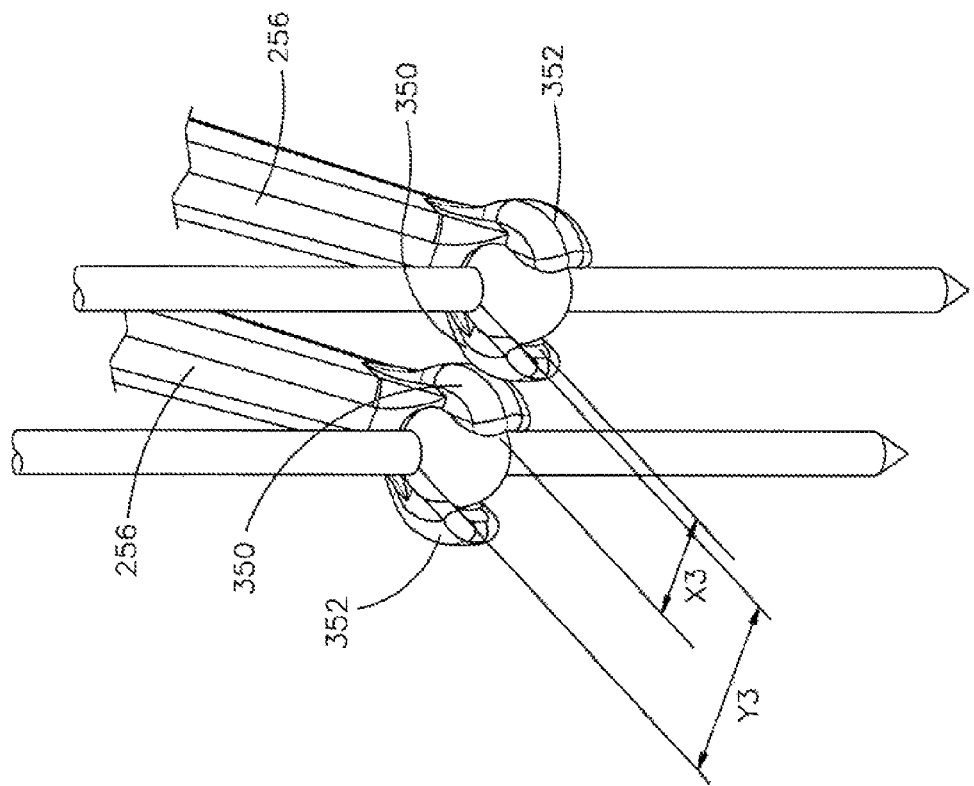
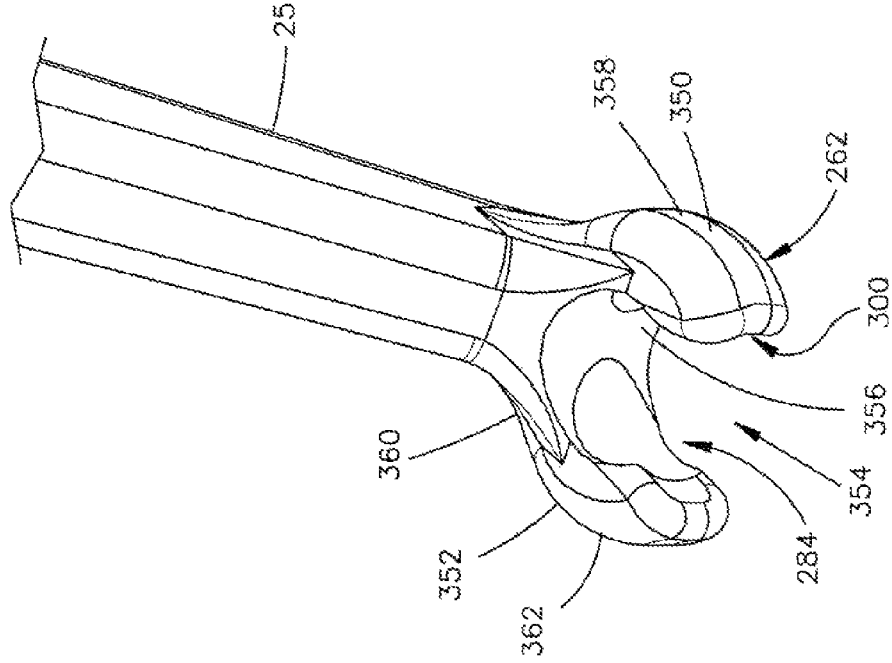
Fig.8E
Fig.8F

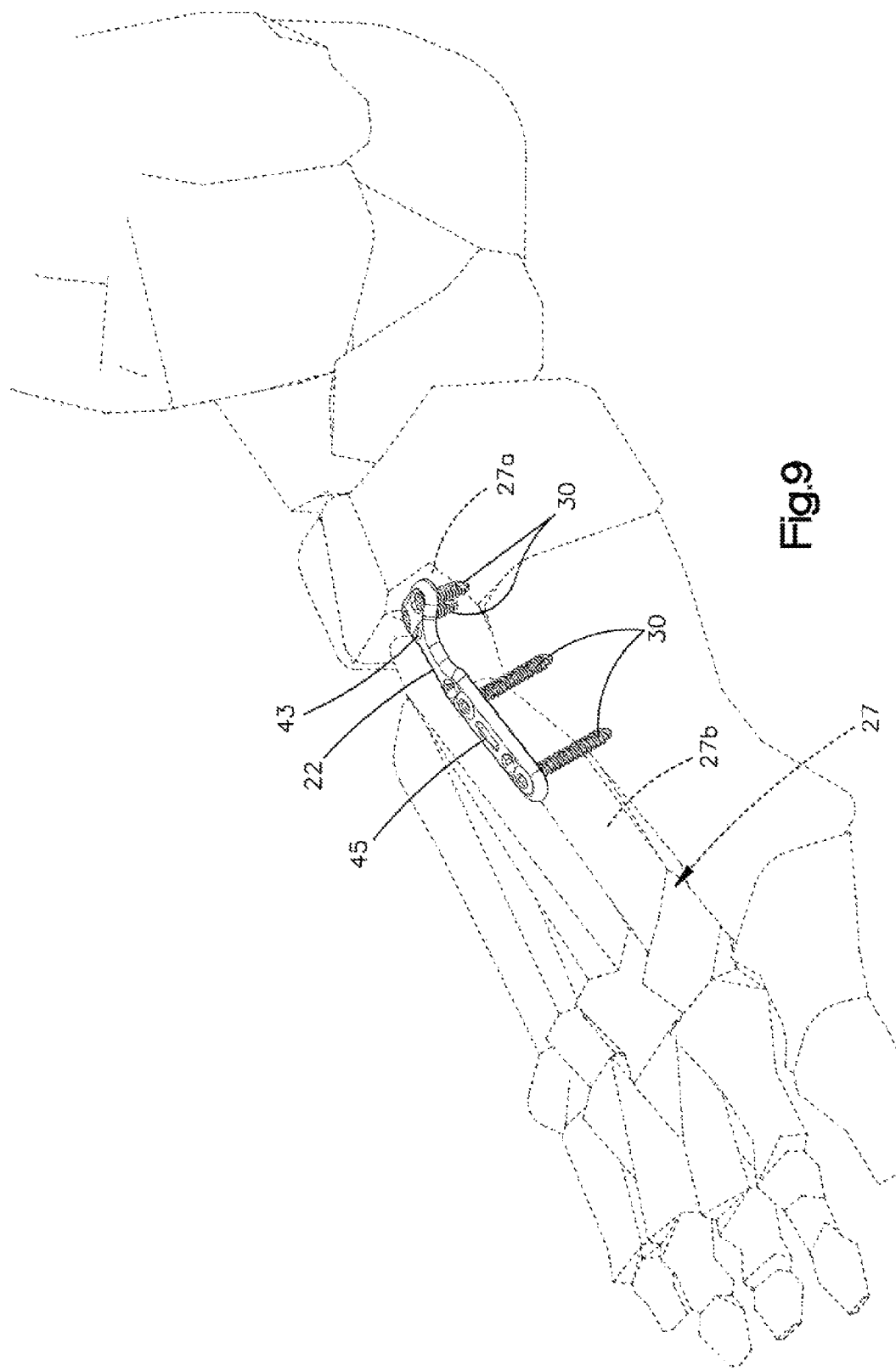

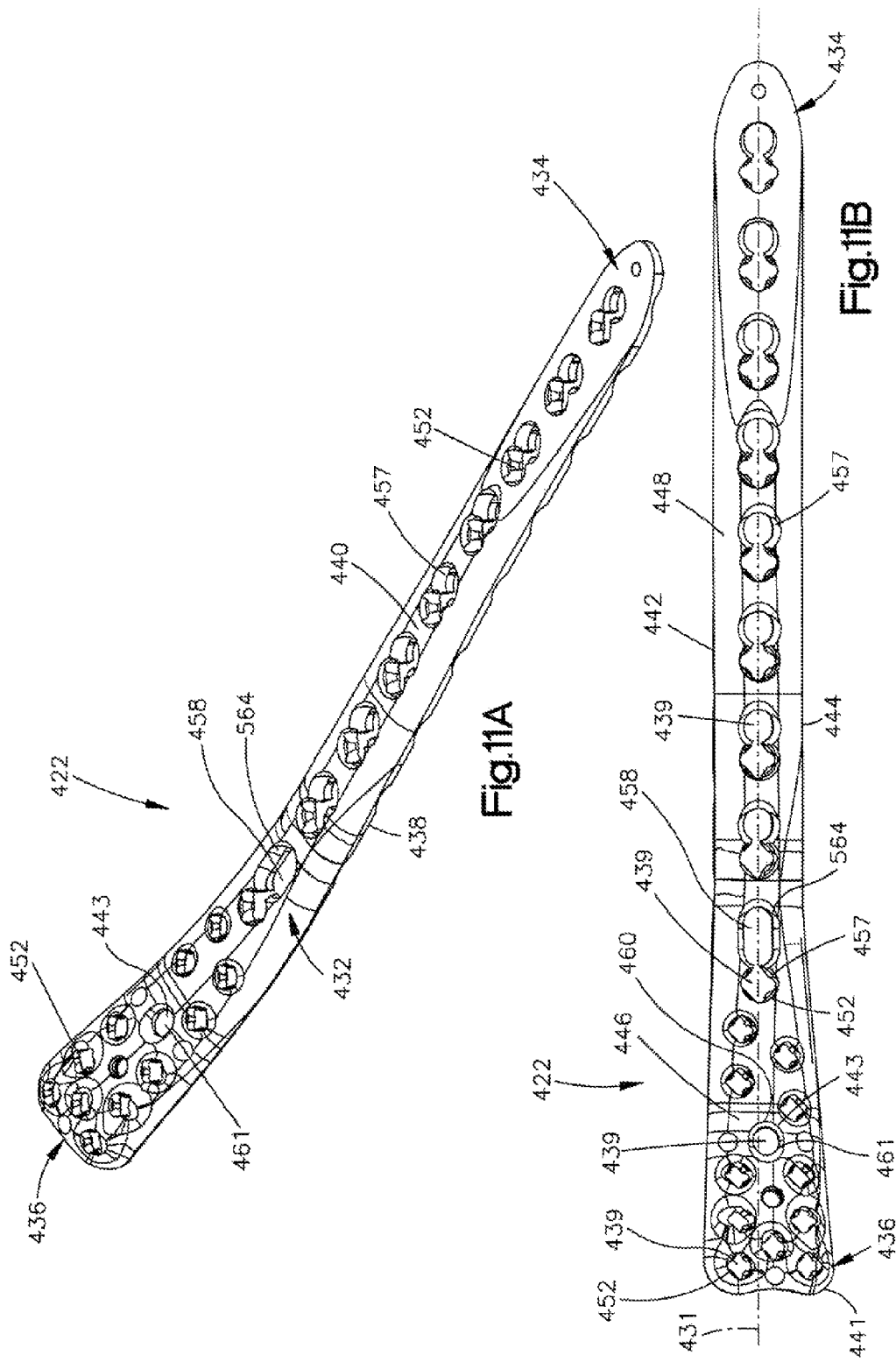

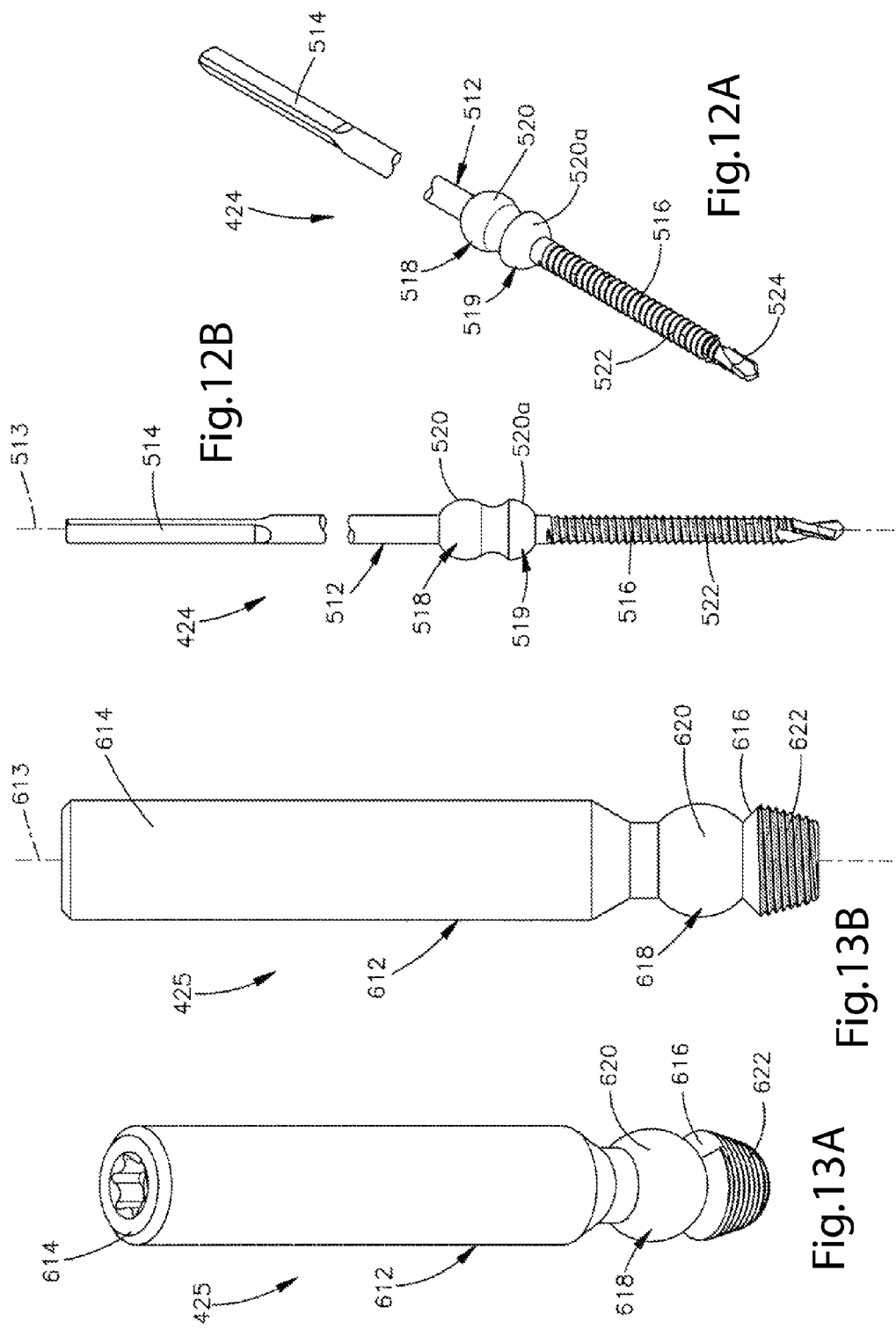

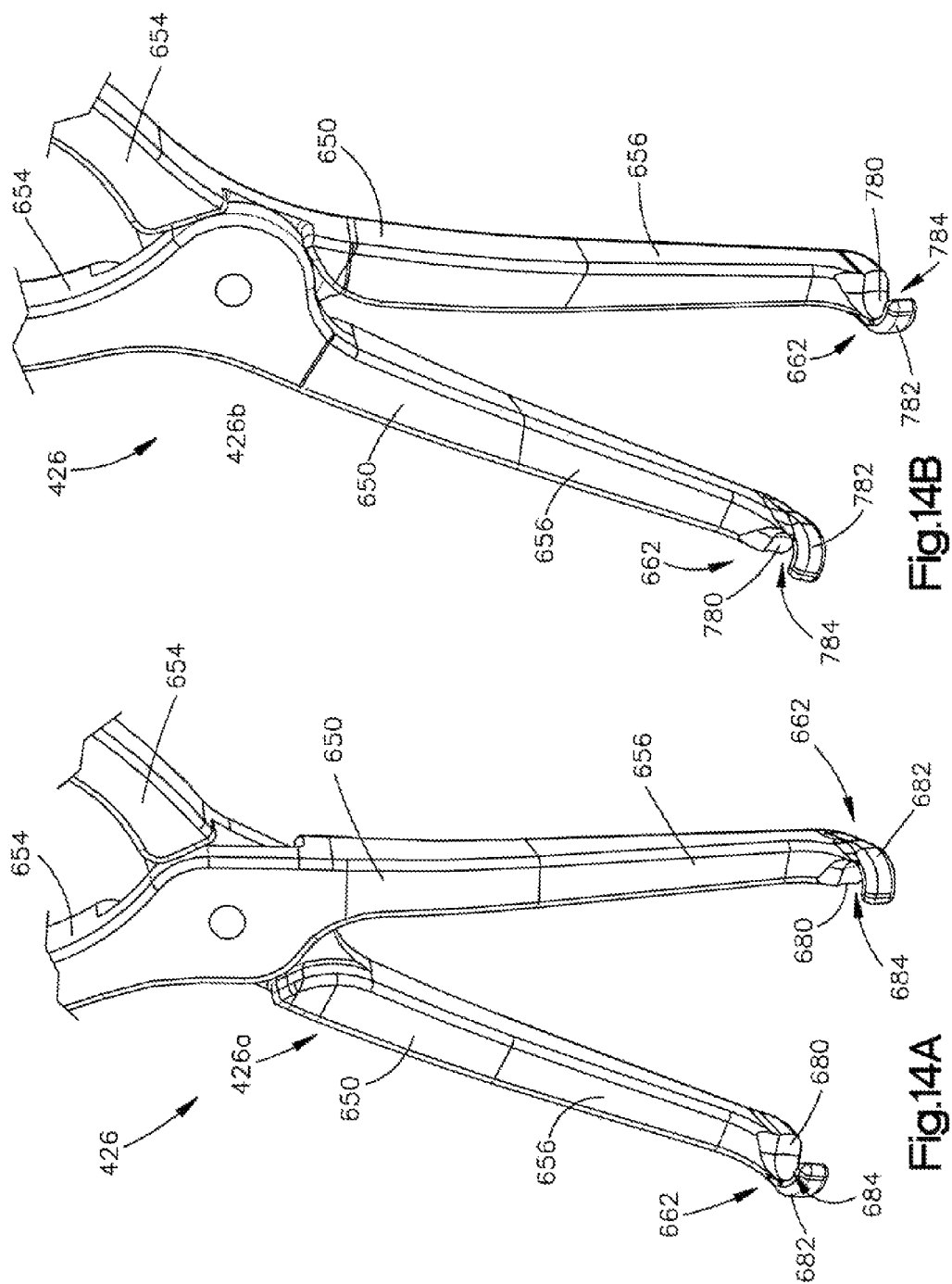

BONE FIXATION SYSTEM INCLUDING K-WIRE COMPRESSION

CROSS-REFERENCE TO RELATED APPLICATIONS

This application claims the benefit of U.S. Provision Application Ser. No. 61/372,212 filed Aug. 10, 2010, and U.S. Provisional Application Ser. No. 61/328,278 filed Apr. 27, 2010, the contents of each of which are incorporated herein by reference in their entirety.

BACKGROUND

Conventional bone fixation systems include a bone plate having screw holes that receive fixation members, such as screws that are configured to attach to underlying bone that includes, at a minimum, a pair of bone segments separated by a bone gap. The bone gap can be a fracture created by a traumatic event, an osteotomy, or can be the result of debridement of a joint of two discrete bones to be joined in an arthodesis. Thus, the bone plate can be affixed to the bone on opposed sides of the bone gap via the bone screws to promote union of the bone segments (e.g., healing of the fracture or ossification of the joint). Bone fixation systems can further include temporary Kirschner wires (K-wires) that are temporarily inserted into apertures of the bone fixation plate and into the underlying bone segments to determine proper length, rotation and alignment of the bone segments prior to permanent plate fixation. Once the bone fixation plate has been properly positioned, the permanent bone screws can be inserted into one or more bone screw holes on opposed sides of the bone gap and affixed to the underlying bone.

In one conventional system, a K-wire is screwed or otherwise driven through the screw holes of the plate on opposite sides of the bone gap. The K-wire is smaller in diameter as the screw holes, and is thus positioned so as to bear against opposing edges of the respective screw holes so as to prevent movement of the plate during imaging. The process of accurately positioning the K-wire so as to prevent movement of the bone plate has proven difficult and tedious, as any space between the K-wire and the outer edge of the screw hole can allow movement of the bone plate.

SUMMARY

In accordance with one embodiment, a method is provided for fixing a bone plate to first and second bone segments that are separated by a bone gap. The method includes the step of aligning the bone plate with the first and second bone segments such that a first plurality of apertures extending through the bone plate are aligned with the first bone segment and a second plurality of apertures extending through the bone plate are aligned with the second bone segment. A select one of the first plurality of apertures is a K-wire slot and a select one of the second plurality of apertures is a K-wire hole. The method further includes the steps of inserting a distal portion of a first K-wire through the K-wire slot and into the first bone segment, inserting a distal portion of a second K-wire through the K-wire hole and into the second bone segment, and actuating a forceps to bias at least one of the K-wires to translate relative to the other K-wire.

In accordance with another embodiment, a forceps is provided that is configured to apply a biasing force to a pair of temporary fixation members. Each temporary fixation member has a distal portion and an engagement member disposed proximal of the distal portion. The engagement member may define a dimension greater than that of the distal portion, and the engagement member may present an outer surface. The forceps may comprise a pair of arms that are pivotally connected at a joint. Each arm may have a proximal end and an opposed distal end. Each arm may further have an engagement member defining a pocket that extends into the distal end. The pocket may define an engagement surface having a shape corresponding to that of the engagement member of the temporary fixation members. Relative movement of the arms causes the distal ends to correspondingly move, such that each pocket at least partially receives a respective one of the temporary fixation members and the engagement surface applies a biasing force against the engagement member of the received temporary fixation member.

In accordance with another embodiment, a bone fixation kit is provided that includes at least one bone fixation plate, at least a pair of temporary fixation members, and a forceps. The plate may include a plurality of apertures, at least some of which are configured to receive respective bone fixation members. Each temporary fixation member may a proximal portion, a distal portion, and an engagement member disposed between the proximal portion and the distal portion. The engagement member may define a cross-sectional dimension greater than that of the distal portion, wherein at least one of the temporary fixation members is configured to extend through a respective one of the plurality of apertures and into an underlying bone segment of a pair of underlying bone segments that are separated by a bone gap. The forceps may include a pair of arms, each arm having a proximal end and an opposed distal end. The distal end may include an engagement member that defines a corresponding engagement surface that is configured to move along a direction so as to abut an engagement member of a respective one of the temporary fixation members, wherein further movement of the engagement surface along the direction causes at least one of the temporary fixation members to translate relative to the other temporary fixation member.

In accordance with another embodiment, a method is provided for positioning first and second bone segments that are disposed in a first relative position in relation to each other and are separated by a bone gap during a surgical procedure. The method includes the step of inserting a distal portion of a first temporary fixation member into the first bone segment, and inserting a distal portion of a second temporary bone fixation member into the second bone segment. The method further includes the step of actuating a forceps to bias at least one of the temporary bone fixation members relative to the other temporary bone fixation member, thereby adjusting the relative positions of the bone segments in relation to each other from the first relative position to a second different relative position. Prior to completion of the surgical procedure the first and second temporary fixation members may be removed from the first and second bone segments, respectively.

In accordance with another embodiment, a method is provided for positioning a bone plate to first and second bone segments that are disposed in a relative position in relation to each other and are separated by a bone gap. The method may include the steps of aligning the bone plate with the first and second bone segments, the bone plate including a plate body and a plurality of apertures extending through the plate body, wherein a first aperture of the plurality of apertures comprises a bone anchor hole that is aligned with the first bone segment, and a second aperture of the plurality of apertures comprises a coupler. The method further includes inserting a bone anchor through the bone anchor hole and into the first bone segment, inserting a distal portion of a post into the second aperture, the distal portion of the post defining a coupler that engages the coupler of the second aperture to thereby fixedly couple the post to the bone plate, and inserting a distal portion of a K-wire into the second bone segment. A forceps may then be actuated to bias at least one of the K-wire and the post to translate relative to the other, thereby adjusting the relative positions of the bone segments in relation to each other.

In accordance with another embodiment, a bone fixation kit is provided. The kit may include at least a pair of temporary bone fixation members, and a forceps. Each temporary bone fixation member may have a proximal portion, a distal portion, and an engagement member disposed between the proximal portion and the distal portion, the engagement member defining a cross-sectional dimension greater than that of the distal portion, wherein the temporary bone fixation members are configured to extend through respective ones of the plurality of apertures and into respective underlying bone segments that are separated by a bone gap. The forceps may include a pair of arms, each arm having a proximal end and an opposed distal end, the distal end including an engagement member that defines a corresponding engagement surface that is configured to move along a direction so as to abut a respective one of the temporary bone fixation members. Further movement of the engagement surface along the direction causes at least one of the temporary bone fixation members to translate relative to the other temporary bone fixation member.

BRIEF DESCRIPTION OF THE DRAWINGS

The foregoing summary, as well as the following detailed description of an example embodiment of the application, will be better understood when read in conjunction with the appended drawings, in which there is shown in the drawings an example embodiment for the purposes of illustration. It should be understood, however, that the application is not limited to the precise arrangements and instrumentalities shown. In the drawings:

FIG. 2A is a top plan view of the bone fixation plate illustrated in FIG. 1A;

FIG. 2B is a top plan view of a variable angle locking hole of the bone fixation plate illustrated in FIG. 2A;

FIG. 2C is a perspective view showing a bone anchor installed in the variable angle locking hole illustrated in FIG. 2B;

FIG. 2D is a top plan view of a combination hole of the bone fixation plate illustrated in FIG. 2A;

FIG. 2E is a sectional side elevation view of the bone fixation plate illustrated in FIG. 2D taken along line 2E-2E so as to illustrate a screw hole;

FIG. 3A is a perspective view of a bone fixation plate constructed in accordance with another embodiment;

FIG. 3B is a top plan view of the bone fixation plate illustrated in FIG. 3A;

FIG. 4A is a top plan view of a bone fixation plate constructed in accordance with another embodiment;

FIG. 4B is a side elevation view of the bone fixation plate illustrated in FIG. 4A;

FIG. 4F is a top plan view of a bone fixation plate constructed in accordance with another embodiment;

FIG. 4G is a top plan view of a bone fixation plate constructed in accordance with another embodiment;

FIG. 5A is a side elevation view of a non-locking bone anchor constructed in accordance with one embodiment;

FIG. 5B is a side elevation view of a locking bone anchor constructed in accordance with an alternative embodiment;

FIG. 5C is a side elevation view of a head portion of the bone anchor illustrated in FIG. 5B;

FIG. 7C is a perspective view of the forceps illustrated in FIG. 7B shown in a closed configuration;

FIG. 7D is a perspective view of a portion of the forceps illustrated in FIG. 7A, showing a ratchet mechanism;

FIG. 7E is an enlarged perspective view of a distal end of the forceps illustrated in FIG. 7A, showing a compression engagement member;

FIG. 8A is an enlarged perspective view of a distal end of the forceps illustrated in FIG. 7A, but constructed in accordance with an alternative embodiment, including compression and distraction engagement members;

FIG. 8E is an enlarged perspective view of a distal end of one arm of the forceps illustrated in FIG. 7A, but constructed in accordance with an alternative embodiment, including a compression and distraction engagement members FIG. 8F is a perspective view of the distal end illustrated in FIG. 8E, schematically showing the compression and distraction engagement members operatively coupled to respective K-wires;

FIG. 9 is a schematic perspective view of a bone fastener secured to bone segments using the bone fixation system illustrated in FIG. 1A;

FIG. 11A is a perspective view of a bone fixation plate constructed in accordance with an alternative embodiment, and illustrated in FIG. 10;

FIG. 11B is a top plan view of the bone fixation plate illustrated in FIG. 11A;

FIG. 12A is a partial perspective view of a K-wire constructed in accordance with an alternative embodiment, and illustrated in FIG. 10;

FIG. 12B is a side elevation view of the K-wire illustrated in FIG. 12A;

FIG. 13A is a front perspective view of a post constructed in accordance with one embodiment, and illustrated in FIG. 10;

FIG. 13B is a side elevation view of the post illustrated in FIG. 13A;

FIG. 14A is a front perspective view of a forceps constructed in accordance with an alternative embodiment, the forceps having compression engagement members;

FIG. 14B is a front perspective view of the forceps illustrated in FIG. 14A, but constructed in accordance with an alternative embodiment, including a distraction engagement members;

DETAILED DESCRIPTION

Figure 1A:
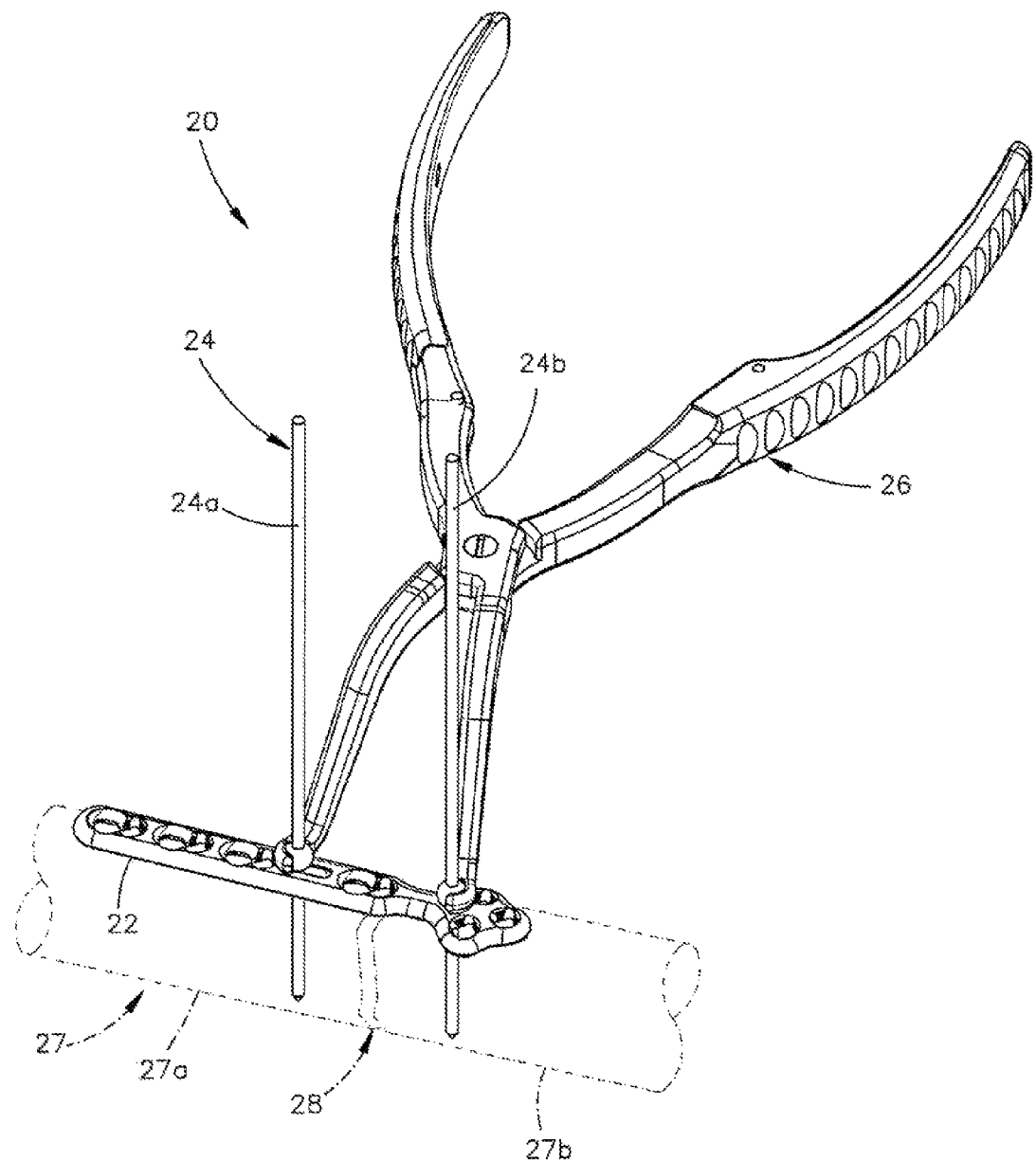
FIG. 1A is a perspective view of a bone fixation system constructed in accordance with one embodiment operatively coupled to a pair of schematically illustrated bone segments separated by a bone gap, the bone fixation system including a bone fixation plate, a pair of K-wires, and a forceps.
Figure 1B:
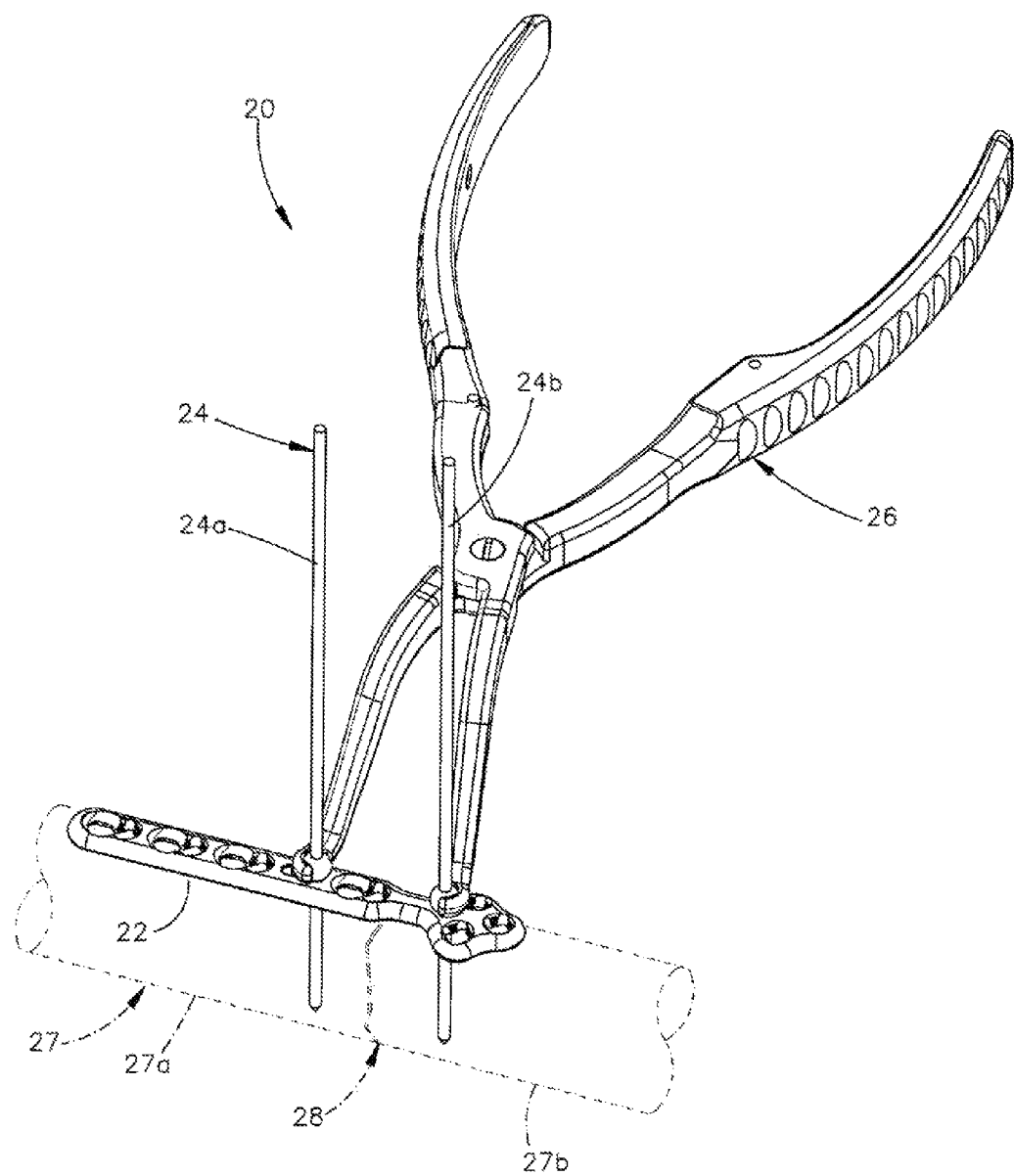
FIG. 1B is a perspective view similar to FIG. 1A, but showing the bone gap reduced by the bone fixation system.

Referring initially to FIG. 1A, a bone fixation system 20 includes a bone fixation plate 22, at least one guide wire or temporary fixation member illustrated as a K-wire 24, such as a pair of opposing K-wires 24a and 24b, and a forceps 26 configured to engage the K-wires 24a and 24b. The bone fixation plate 22 can be operatively coupled to an underlying bone 27 having bone segments 27a and 27b separated by a bone gap 28. The bone gap can be a fracture created by a traumatic event, an osteotomy, or can be the result of debridement of a joint of two discrete bones to be joined in an arthodesis. The bone fixation plate 22 is placed against or in proximity with the underlying bone 27, the K-wires 24a and 24b are inserted through the plate 22 and into the respective bone segments 27a and 27b, and the forceps 26 can apply a force onto the K-wires so as to translate at least one of or both of the bone segments 27a and 27b, thereby adjusting the relative positions of the bone segments 27a and 27b in relation to each other. For instance, the forceps 26 can apply a compressive force that brings at least one or both of the bone segments 27a and 27b toward the other, thereby reducing the bone gap 28 to promote union of the bone segments 27a and 27b, as illustrated in FIG. 1B. In accordance with certain embodiments, the forceps 26 can apply a distractive force onto the K-wires so as to urge one or both of the bone segments 27a and 27b away from the other, thereby distracting the bone gap 28, for instance from the position illustrated in FIG. 1B to the position illustrated in FIG. 1A. The bone fixation plate 22 can be geometrically configured for fixation to bone 27, which can be the forefoot, midfoot, hindfoot, distal tibia, or any bone in the human body as desired, either in vivo or ex vivo. The bone fixation plate 22 can alternatively be fixed in the manner described above to any suitable non-human animal body bone, in vivo or ex vivo.

The bone fixation system 20 can further include a plurality (e.g., at least two) bone anchors 30 (see FIG. 2C) that secure the bone fixation plate 22 to the underlying bone 27 on opposed sides of the bone gap 28. The bone fixation system 20 and components of the bone fixation system 20 can be made from any suitable biocompatible material, such as titanium, including titanium alloys, stainless steel, ceramics, or polymers such as polyetheretherketone (PEEK), cobalt chromium molybdenum (CoCrMo) with a porous plasma-sprayed titanium coating, or any suitable alternative material as desired.

Referring now to FIG. 2A, the bone fixation plate 22 can be made in different shapes and sizes for use in a wide variety of clinical applications. The bone fixation plate 22 is elongate along a longitudinal direction L, defines a width along a lateral direction A that is perpendicular or substantially perpendicular to the longitudinal direction L, and a thickness along a transverse direction T that is perpendicular or substantially perpendicular to both the longitudinal direction L and the lateral direction A. In this regard, it should be appreciated that the various directions can extend along directions that are 90° angularly offset from each other, or anywhere within the range of approximately 45° and approximately 90° angularly offset from each other.

The bone fixation plate 22 includes a plate body 32 that extends substantially along a central longitudinal axis 31, and defines a proximal end 34 and a distal end 36 opposite the proximal end 34 along the longitudinal axis 31. The plate body 32 further includes a bone-facing inner surface 38 and an opposed outer surface 40 spaced from the inner surface 38 along the transverse direction T. The plate body 32 further defines opposed side surfaces 42 and 44 that are spaced from each other along the lateral direction A. The plate body 32 includes a head portion 46 at the distal end 36 that can be configured and dimensioned to conform to the contour of the near cortex of the underlying bone 27, and a shaft portion 48 connected to the head portion 46 and disposed longitudinally proximal from the head portion 46. The shaft portion 48 can be configured and dimensioned to conform to the contour of the near cortex of the underlying bone 27. In accordance with the illustrated embodiment, the head portion 46 resembles the shape of a cloverleaf, though it should be appreciated that the head portion 46 can assume any geometric shape as desired. The cloverleaf-shaped plate can be used in a number of bony applications, especially where a short bone segment is present. The cluster of the "cloverleaf" design allows the surgeon to place three screws for three points of fixation in a small surface area which can provide greater stability than two points of fixation in the same surface area.

The bone facing surface 38 of the head portion 46 can be generally coplanar with or offset from the bone facing surface 38 of the shaft portion 48. For instance, the bone facing surface 38 of the head portion 46 and the shaft portion 48 can be curved so as to conform to the contours of the underlying bone 27. The plate body 32 can further include a neck portion 50 connected between the head portion 46 and the shaft portion 48. The neck portion 50 can be straight, curved, and can define a lateral thickness that is greater than, less than, or substantially equal to that of the head portion and the shaft portion 48. In accordance with the illustrated embodiment, the neck portion 50 has a lateral thickness less than that of the head portion 46 and the shaft portion 48.

With continuing reference to FIG. 2A, the bone plate 22 includes a plurality of apertures 39 that extend transversely through the plate body 32, from the bone-facing inner surface 38 through to the outer surface 40. The apertures 39 can include at least one such as a plurality of bone anchor holes 41, at least one such as a plurality of K-wire holes 23 which can be dedicated K-wire holes 43, and at least one such as a plurality of longitudinally elongate K-wire slots 25 which can be dedicated K-wire slots 45. As will become appreciated from the description below, the K-wire hole 43 and the K-wire slot 45 can be dedicated to receive respective K-wires, or can each also be configured as a bone anchor hole that are configured to receive both a bone anchor and a K-wire.

As will now be described with respect to FIGS. 2A-2G, one or more of the bone anchor holes 41 up to all of the bone anchor holes 41 can be configured as a variable angle hole 52, a fixed axis hole 54, a combination hole 57 including a variable angle hole portion and a fixed angle hole portion, and can further be configured as a compression hole, a threaded locking hole, or a combination of both. It should be appreciated that at least one up to all of the bone anchor hole 41, the K-wire hole 43, and the K-wire slot 45 can extend through the head portion 46, the shaft portion 48, and/or the neck portion 50 as desired. In accordance with the illustrated embodiment, the bone plate 22 includes a plurality of variable angle holes 52 that extend through the head portion 46. For instance, the bone plate 22 includes a pair variable angle holes 52 extending through the head portion 46 that are laterally spaced from each other and aligned along the lateral direction A, and a third variable angle hole 52 that extends through the head portion 46 at a location distal of and laterally between the holes 52.

Referring now also to FIG. 2B, each variable angle hole 52 is defined by an interior surface 55 of the bone plate body 32. The interior surface 55 includes a plurality of vertical or transversely extending columns 56. In accordance with the illustrated embodiment, four columns 56 are equidistantly spaced circumferentially about the hole 52, though the plate body 32 can alternatively include any number of columns as desired, spaced circumferentially equidistantly as illustrated, or at circumferentially variable distances as desired. Each column 56 presents internal threads 58 that face the hole 52 such that, if the columns 56 were expanded to join each other (i.e. if extended completely around the interior surface 55), the columns 56 would form a continuous helical thread that extend about the central transverse axis 49. Thus, it can be said that the threads 58 of adjacent columns 56 are operatively aligned with each other.

It should be appreciated that while the columns 56 present internal helical threads 58 as illustrated, the columns 56 alternatively can define threads that are provided as teeth formed thereon. The columns of teeth, if expanded to join each other (i.e., if extended completely around the interior surface 55), will not form a helical thread, but a series of concentric ridges and grooves perpendicular to the central axis 49 of the bone plate hole 52. Thus, it can be said that the teeth can be operatively aligned with each other. The columns 56 are circumferentially spaced from each other so as to define corresponding axes that are angled with respect to the transverse central axis 49, such that a screw can extend through the hole 52 at any of the angled axes while threadedly fixed to the threads 58.

The interior surface 55 that defines the hole 52 further includes a plurality of arcuate pockets 60 that project into the plate body 32 at a location circumferentially between the adjacent columns 56. The pockets 60 each presents an arcuate surface 62 that is concave with respect to a direction radially outward from the central axis 49 of the hole 52. As illustrated in FIG. 2C, and as described in more detail below, the bone anchor 30 can be provided as a variable locking bone anchor 61 that can threadedly engage the threads 58 at variable angular positions. Alternatively, the bone anchor 30 can be provided as a fixed angle locking screw that purchases with the threaded columns 56 and extends along the transverse axis 49. The variable angle holes 52 can be configured to allow the bone anchor to engage the threads 58 at any angular orientation as desired, up to +/−15° (e.g., within a 30° range) with respect to the central axis 49, which extends along the transverse direction T. The variable angle hole 52 is further described in U.S. Patent Application Publication No. 2008/0140130, published Jun. 12, 2008, the disclosure of which is hereby incorporated by reference as if set forth in its entirety herein.

Referring now also to FIGS. 2D-E, the fixed axis hole 54 can be generally cylindrical, such that the bone plate body 32 defines a substantially cylindrical interior surface 64 that is substantially cylindrical and at least partially defines the hole 54. The hole 54, and thus the interior surface 64 can extend entirely through the plate body 32, from the bone facing surface 38 through to the outer surface 40 along a central transverse axis 51. The interior surface 64 can be enclosed, or the plate body 32 can define a circumferential gap 65 that extends longitudinally through a portion of the interior surface 64, so as to extend between the fixed axis hole 54 and the variable angle hole 52 of the combination hole 57. The gap 65 can extend transversely entirely through the plate body 32, from the outer surface 40 through to the inner surface 38. The interior surface 64 of the combination hole 57 illustrated in FIG. 2D can be unthreaded such that a screw head of a screw inserted into the hole 54 of the combination hole 57 can compress the bone plate 22 to the underlying bone 27, and/or compress the bone fragments 27a and 27b together. For instance, the screw can be inserted into the underlying bone 27 at one side of the hole 54 at a location offset with respect to the central axis of the hole, such that as the screw is compressed against the plate 22, the hole 54 aligns with the screw, which causes the bone plate 22 to translate in a direction that compresses the bone fragments 27a and 27b.

Thus, it should be appreciated that the plate 22 can define at least one or more discrete variable angle holes 52 and fixed axis holes 54, or the plate 22 can define at least one or more combination holes 57 that include a variable angle hole 52 and a fixed axis hole 54 connected by the gap 65 that extends transversely through the plate body 32. In accordance with the illustrated embodiment, the variable angle hole 52 of a given combination hole 57 is spaced longitudinally distal with respect to, and longitudinally aligned with, the respective variable angle hole 52 of a given combination hole 57. The combination hole 57 is further described in U.S. Patent Application Publication No. 2008/0140130, published Jun. 12, 2008, the disclosure of which is hereby incorporated by reference as if set forth in its entirety herein.

The interior surface 64 can extend in a transverse direction, such that the hole 54 has a constant diameter along its length through the plate body 32. As illustrated in FIG. 2E, the interior surface 64 can present internal threads 58 that are configured to engage complementary threads of the head of a locking bone anchor, as described in more detail below. It should be appreciated that a screw having a fixed-angle head (also referred to as a fixed angle screw) can be inserted into the fixed axis hole 54 along the transverse axis of the hole 54. For instance, the fixed angle screw can include a conically-shaped screw head. Alternatively, a screw having a variable angle head, (also referred to as a variable angle screw) can be inserted into the fixed axis hole 54 at an angle with respect to the transverse central axis 51. For instance, the variable angle screw can be provided as a cortical screw, or a screw whose screw head defines an outer cancellous thread.

Figure 2F:
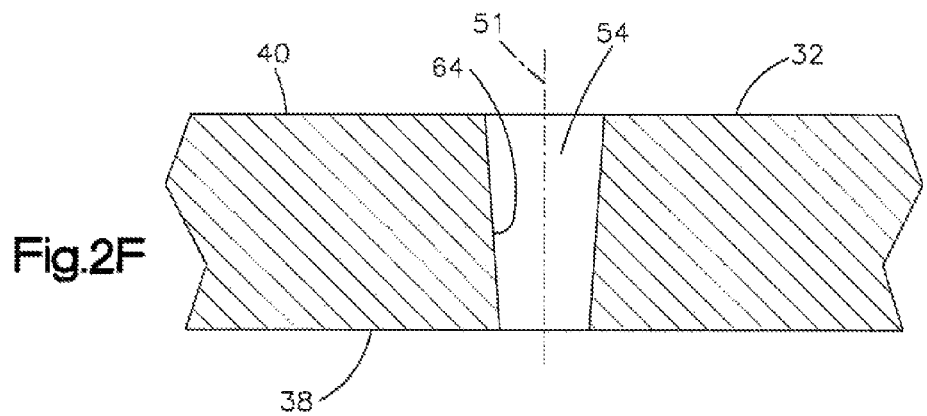
FIG. 2F is a sectional side elevation view of the bone fixation plate similar to FIG. 2E, but showing the screw hole constructed in accordance with an alternative embodiment.

Alternatively, as illustrated in FIG. 2F, the interior surface 64 can be tapered radially inward along the transverse direction from the outer surface 40 to the inner bone facing surface 38. The interior surface 64 can be unthreaded and configured to engage an unthreaded head of a compression bone anchor that provides a compressive force against the plate 22 in a direction toward the underlying bone, as will be described in more detail below. Alternatively, the interior surface 64 can be threaded, as described in U.S. Pat. No. 6,206,881, the disclosure of which is hereby incorporated by reference as if set forth in its entirety herein, so as to mate with complementary threads of the head of a locking bone anchor. Alternatively still, an outer region of the interior surface 64 can be unthreaded so as to engage a compression bone anchor head, and an inner region of the interior surface 64 can be threaded so as to mate with complementary threads of a locking bone anchor head.

Figure 2G:
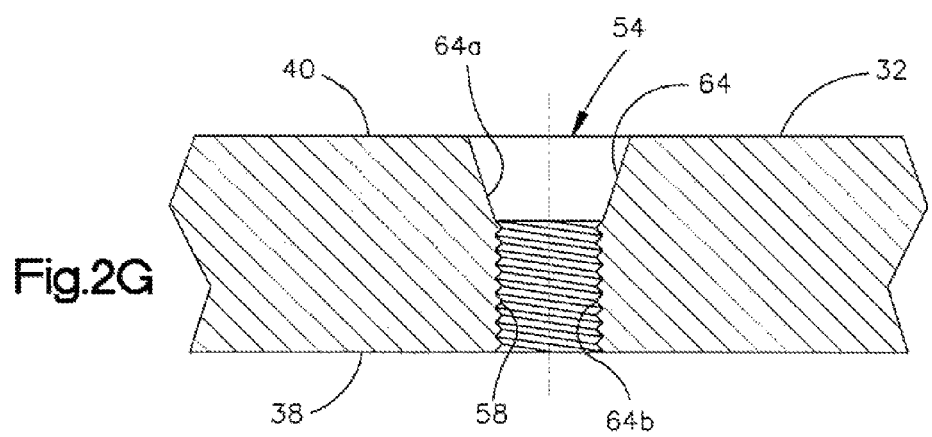
FIG. 2G is a sectional side elevation view of the bone fixation plate similar to FIG. 2F, but showing the screw hole constructed in accordance with an alternative embodiment.

Alternatively still, as illustrated in FIG. 2G, a portion of the interior surface 64 can be tapered radially inward along the transverse direction from the outer surface 40 toward the inner bone facing surface 38. Thus, the fixed axis hole 54 can define a diameter that decreases along a direction from the outer surface 40 to the inner surface 38. A portion or all of the interior surface 64 can be substantially linear (e.g., frusto-conical or generally conically tapered), such that the diameter of the hole 54 decreases linearly, or part or all of the interior surface 64 can be curved, such that the diameter of the hole 54 decreases variably along the transverse direction from the outer surface 40 toward the inner surface 38.

For instance, the interior surface 64 can define a first or outer transverse region 64a that extends transversely from the outer surface 40 toward the inner surface 38, and a second or inner transverse region 64b extending from the outer transverse region 64a towards, and to, the bone facing surface 38. The outer transverse region 64a can be tapered along the transverse direction from the outer surface 40 toward the inner surface 38, and can be unthreaded and configured to engage an unthreaded head of a non-locking or compression bone anchor that provides a compressive force against the plate 22 in a direction toward the underlying bone. The inner transverse region 64b can extend in a transverse direction, so as to define a substantially constant diameter along its transverse length. The inner transverse region 64b can present internal threads 58 that are configured to engage complementary threads of the head of a locking bone anchor.

It should be appreciated that while the bone plate 22 is illustrated as including variable angle holes 52 extending through the head portion 46 and combination holes 57 extending through the shaft portion 48, the bone plate 22 can alternatively include any bone anchor hole 41 of the embodiment described above that extends through the head portion 46 and the shaft portion 48. Furthermore, multiple embodiments of the bone anchor hole 41 can extend through head portion 46, while multiple embodiments of the bone anchor hole 41 can extend through the shaft portion 48. The anchor holes 41 extending through the head portion 46 can be the same or different as the anchor holes 41 that extend through the shaft portion 48.

Referring again to FIGS. 1A-2A, the K-wire hole 43 and the K-wire slot 45 are separated by an intermediate portion 35 configured to extend over the bone gap 28 of the underlying bone 27, such that the proximal end 34 can be fastened to one bone segment 27a or 27b and the distal end 36 can be fastened to the other bone segment 27a or 27b. In this regard, it can be said that the K-wire hole 43 extends through a first portion 29 of the bone plate body 32, and the K-wire slot 45 extends through a second portion 33 of the bone plate body 32 that is longitudinally proximally spaced from the first portion 29. Alternatively or additionally, a K-wire slot 45 can extend through the first portion 29 and a K-wire hole 43 can extend through the second portion 33. The K-wire slot 45 can be longitudinally aligned with, the K-wire hole 43, and the intermediate portion 35 is disposed between the first and second portions 31 and 33. At least one bone anchor hole 41 can extend through the bone plate body 32 at a location proximate to the K-wire hole 43 (for instance at the first portion 29), and at least one bone anchor hole 41 can extend through the bone plate body 32 at a location proximate to the K-wire slot 45 (for instance at the second portion 33).

The intermediate portion 35 can include one or more up to all of a proximal end of the head portion 46 and a distal end of the shaft portion 48, a neck portion that may extend between the head portion 46, and the shaft portion 48. Alternatively, it should be appreciated that certain bone plates may not define a discrete shaft portion, neck portion, and/or head portion. Accordingly, the K-wire hole 43 is operatively aligned with one bone segment 27a or 27b and the K-wire slot 45 is operatively aligned with the other bone segment 27a or 27b.

In accordance with the illustrated embodiment, the K-wire hole 43 extends transversely through the head portion 46, from the outer surface 40 through to the inner surface 38 at a laterally location disposed proximal of the variable angle holes 52.

The dedicated K-wire hole 43 is defined by an interior surface 66 of the bone plate 22 that extends transversely through the plate body 32, from the outer surface 40 through to the inner surface 38. The hole 43 can be centrally located on the longitudinal axis 31 as illustrated, or laterally offset with respect to the longitudinal axis 31. The interior surface 66 can be circular in cross-section as illustrated, such that the hole 43 is cylindrical, or the interior surface 66 and hole 43 can define any shape as desired. The hole 43 defines a diameter or cross-sectional dimension less than that of the bone anchor holes 41 and substantially equal to the diameter of the K-wire 24 that is inserted through the hole 43 and into the underlying bone 27. Thus, the hole 43 defines a lateral dimension substantially equal to that of the K-wire 24, and the longitudinal dimension substantially equal to that of the K-wire 24. As a result, the K-wire 24 can be configured to abut the interior surface 66 as the bone gap 28 is reduced and distracted. In this regard, it should be appreciated that the hole 43 can alternatively be sized greater than the K-wire 24, and the K-wire can be positioned in the hole 43 so as to abut the interior surface 66 at the location that is closest to the K-wire slot 45 when the underlying bone gap is to be reduced, and at the location that is furthest from the K-wire slot 45 when the underlying bone gap is to be distracted. In accordance with the illustrated embodiment, the hole 43 is longitudinally aligned with the slot 45, such that the underlying bone gap 28 can be reduced and distracted in the longitudinal direction L as desired.

Figure 2H:
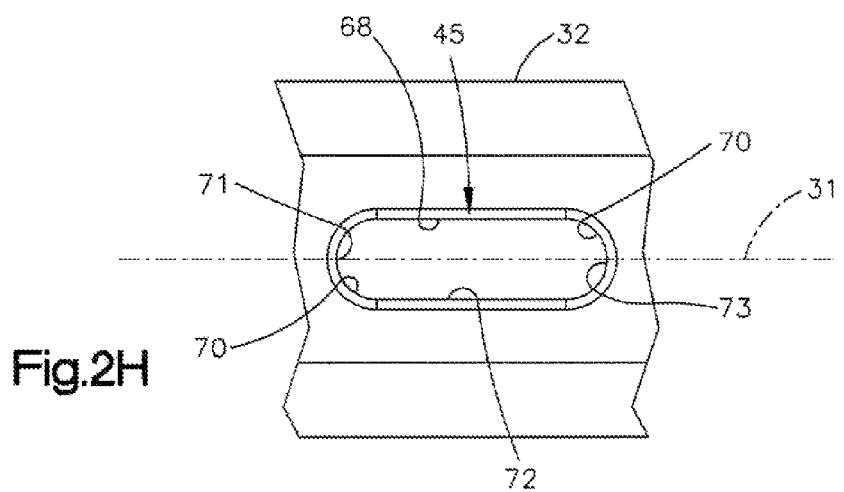
FIG. 2H is an enlarged top plan view of the bone fixation plate illustrated in FIG. 2A, showing a dedicated K-wire slot.

Referring also to FIG. 2H, the dedicated K-wire slot 45 is defined by an interior surface 68 of the bone plate 22 that extends transversely through the plate body 32, from the outer surface 40 through to the inner surface 38. The slot 45 can be centrally located on the longitudinal axis 31 as illustrated, or laterally offset with respect to the longitudinal axis 31. The interior surface 68 includes a pair of longitudinally opposed terminal end portions 70 and an intermediate portion 72 extending longitudinally between the end portions 70. Thus, the slot 45 is longitudinally elongate, and is longitudinally aligned with the K-wire hole 43.

The slot 45 defines a lateral width substantially equal to the diameter of the K-wire hole 43. Both the lateral width of the slot 45 and the diameter of the K-wire hole 43 can be substantially equal to that of respective K-wires 24, such that one K-wire 24 can be inserted through the hole 43 and fixed with respect to longitudinal and lateral motion relative to the bone plate 22, while the other K-wire is inserted through the slot 45 and into the underlying bone 27 and fixed with respect to lateral motion relative to the bone plate 22 but longitudinally translatable within the slot 45 relative to the bone plate 22. The end portions 70 of the interior surface 68, and thus of the slot 45, can be curved as illustrated, and can be defined by a radius R that is substantially equal to one-half the lateral width of the slot 45, such that the corresponding K-wire 24 is fixed with respect to lateral movement relative to the plate 22 when the K-wire 24 is disposed at the end portion 70. The end portions 70 can be configured in any alternative size and shape as desired. The end portions 70 define a leading edge 71 and an opposing trailing edge 73. The leading edge 71 is disposed closer to the K-wire hole 43, and limits the compression of the underlying bone segments 27a-b (and reduction of the bone gap 28). The trailing edge 73 is spaced further from the K-wire hole 43, and limits the distraction of the underlying bone segments 27a-b.

With continuing reference to FIG. 2A, the K-wire hole 43 is illustrated as extending through the head portion 46, and the K-wire slot 45 is illustrated as extending through the shaft portion 48. However, it should be appreciated that the K-wire hole 43 can alternatively extend through the head portion 46, the shaft portion 48, or the neck portion 50. Alternatively still, the bone plate 22 can include a plurality of K-wire holes 43, each extending through the head portion 46, the shaft portion 48, the neck portion 50, or a combination of one or more up to all of the head portion 46, the shaft portion 48, and the neck portion 50. Likewise, it should be appreciated that the K-wire slot 45 can alternatively extend through the head portion 46, the shaft portion 48, or the neck portion 50. Alternatively still, the bone plate 22 can include a plurality of K-wire slots 45, each extending through the head portion 46, the shaft portion 48, the neck portion 50, or a combination of one or more up to all of the head portion 46, the shaft portion 48, and the neck portion 50, alone or in combination with the one or more K-wire holes 43.

Figure 2I:
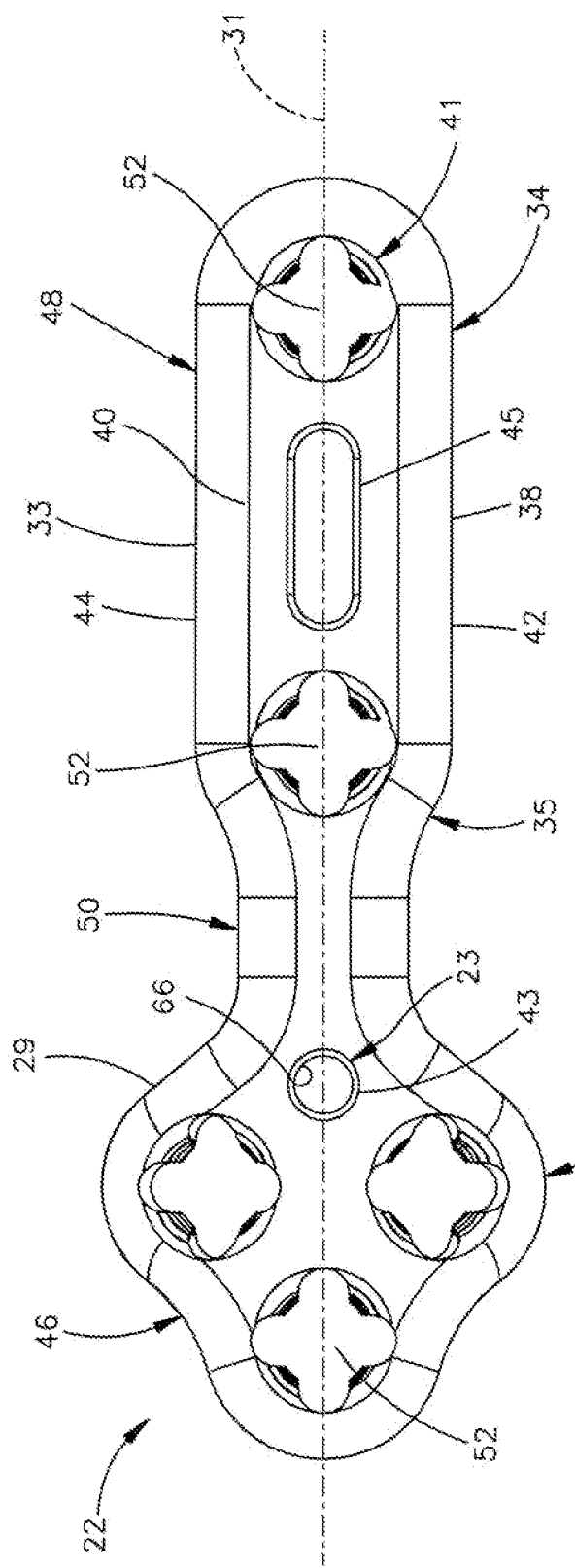
FIG. 2I is a top plan view of a bone fixation plate similar to FIG. 2A, but constructed in accordance with an alternative embodiment.

Furthermore, as illustrated in FIG. 2A, the K-wire hole 43 is disposed proximal of the bone anchor holes 41 that extend through the head portion 46. It should be appreciated, however, that the K-wire hole 43 can alternatively be disposed distally of the bone anchor holes 41 that extend through the head portion 46, or longitudinally between one or more bone anchor holes 41 that extend through the head portion 46. Thus, one or more bone anchor holes 41 extending through the head portion 46 can be disposed proximal to or distal of the K-wire hole 43. Similarly, one or more bone anchor holes 41 extending through the shaft portion 48 can be disposed proximate to or distal of the K-wire slot 45. For instance, as illustrated in FIG. 2I, the slot 45 is disposed between a pair of bone anchor holes 41 that are configured as variable angle holes 52.

Figure 3C:
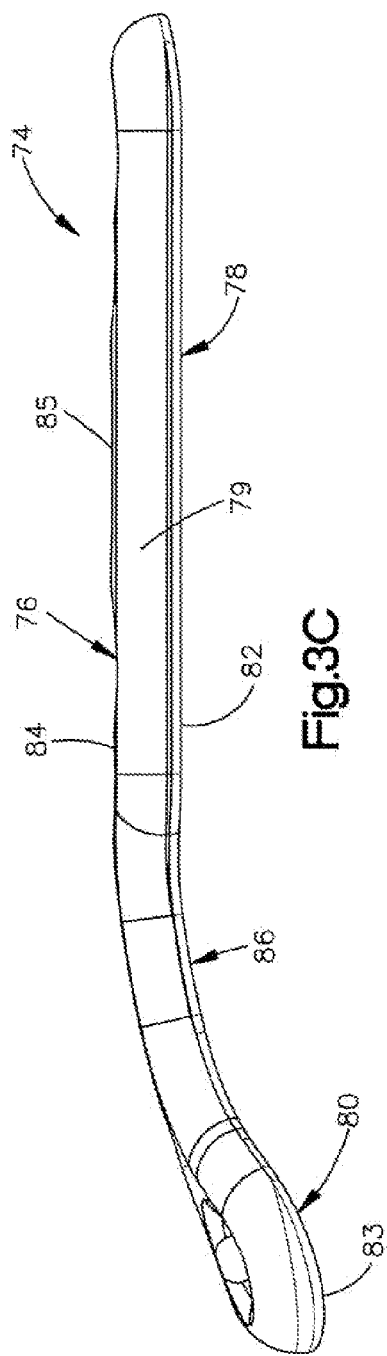
FIG. 3C is a side elevation view of the bone fixation plate illustrated in FIG. 3A.

It should be appreciated that the bone plate 22 has been described above in accordance with one embodiment, and that the bone fixation system 20 can include bone plates of different geometric configurations suitable for fixation to various bones throughout the body. For instance, referring to FIGS. 3A-C, a bone plate 74 is provided as a tarsal metatarsal joint fusion plate that is configured to join a tarsal bone (cuneiform) to either the second or third metatarsal. In accordance with the illustrated embodiment, the bone plate 74 includes a substantially T-shaped plate body 76 that extends substantially along a central longitudinal axis 77, and defines a proximal end 78 and a distal end 80 opposite the proximal end 78 along the longitudinal axis 77.

The plate body 76 further includes a bone-facing inner surface 82 and an opposed outer surface 84 spaced from the inner surface 82 along the transverse direction T. The plate body 76 further defines opposed side surfaces 79 and 81 that are spaced from each other along the lateral direction A. The plate body 76 includes a head portion 83 at the distal end 80 that can be configured and dimensioned to conform to the contour of the near cortex, and a shaft portion 85 connected to the head portion 83 and disposed longitudinally proximal from the head portion 83. The shaft portion 85 can be configured and dimensioned to conform to the contour of the near cortex. The head portion extends laterally outward with respect to the shaft on both sides of the longitudinal axis 77. The plate body 76 further includes a neck portion 86 connected between the head portion 83 and the shaft portion 85. The neck portion 86 defines a lateral width less than that of the shaft portion 85 and the head portion 83. In accordance with the illustrated embodiment, the head portion 83 and neck portion 86 are curved, and extend transversely inward with respect to the shaft portion 85 along the a longitudinal distal direction from the shaft portion 85.

The bone plate 74 can include a plurality of apertures 39 extending through the bone plate body 76 in the manner described above. The apertures 39 can include at least one bone anchor hole 41, at least one dedicated K-wire hole 43, and at least one longitudinally elongate dedicated K-wire slot 45. The bone anchor holes 41, the K-wire hole 43, and the K-wire slot 45 can be constructed as described above with respect to the bone plate 22. In accordance with the illustrated embodiment, the plate body 76 includes a pair of longitudinally spaced combination holes 57 extending through the shaft portion 85, and a longitudinally extending K-wire slot 45 disposed between the combination holes 57. The combination holes 57 and the K-wire slot 45 are illustrated as extending along the longitudinal axis 77. The plate body 76 includes a pair of laterally spaced variable angle holes 52 that extend through the head portion 83 on opposed sides of the longitudinal axis 77, and a K-wire hole 43 that extends through the head portion 83 at a location coincident with the longitudinal axis 77 and proximal from the variable angle holes 52.

Figure 3D:
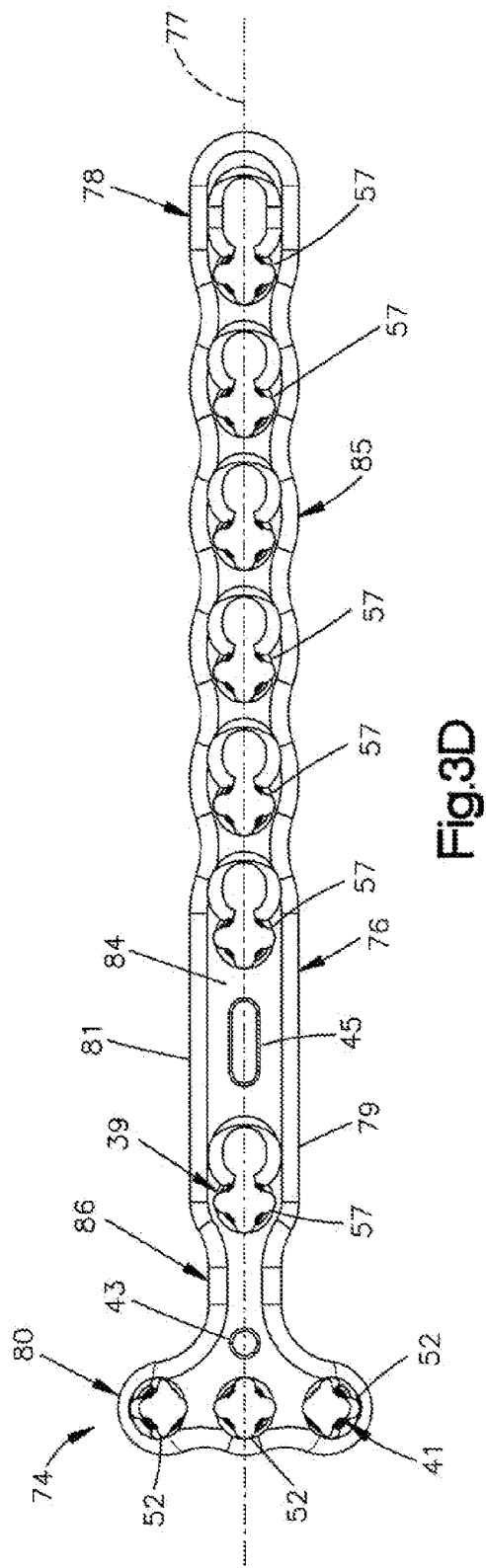
FIG. 3D is a top plan view of a bone fixation plate constructed similar to the bone plate illustrated in FIG. 3A, but in accordance with another embodiment.

Referring to FIG. 3D, the head portion 83 can be sized to accommodate any number of apertures 39 as desired. For instance, in accordance with the illustrated embodiment, head portion 83 can include three apertures 39, which are configured as variable angle holes 52. One of the variable angle holes 52 of the head portion 83 can be located centrally on the longitudinal axis 77, while a pair of the variable angle holes 52 of the head portion 83 can be disposed laterally outward with respect to the central variable angle hole 52. Furthermore, the shaft portion 85 can include a plurality of apertures 39, illustrated as combination holes 57, that are spaced longitudinally proximal of the K-wire slot 45.

Figure 3E:
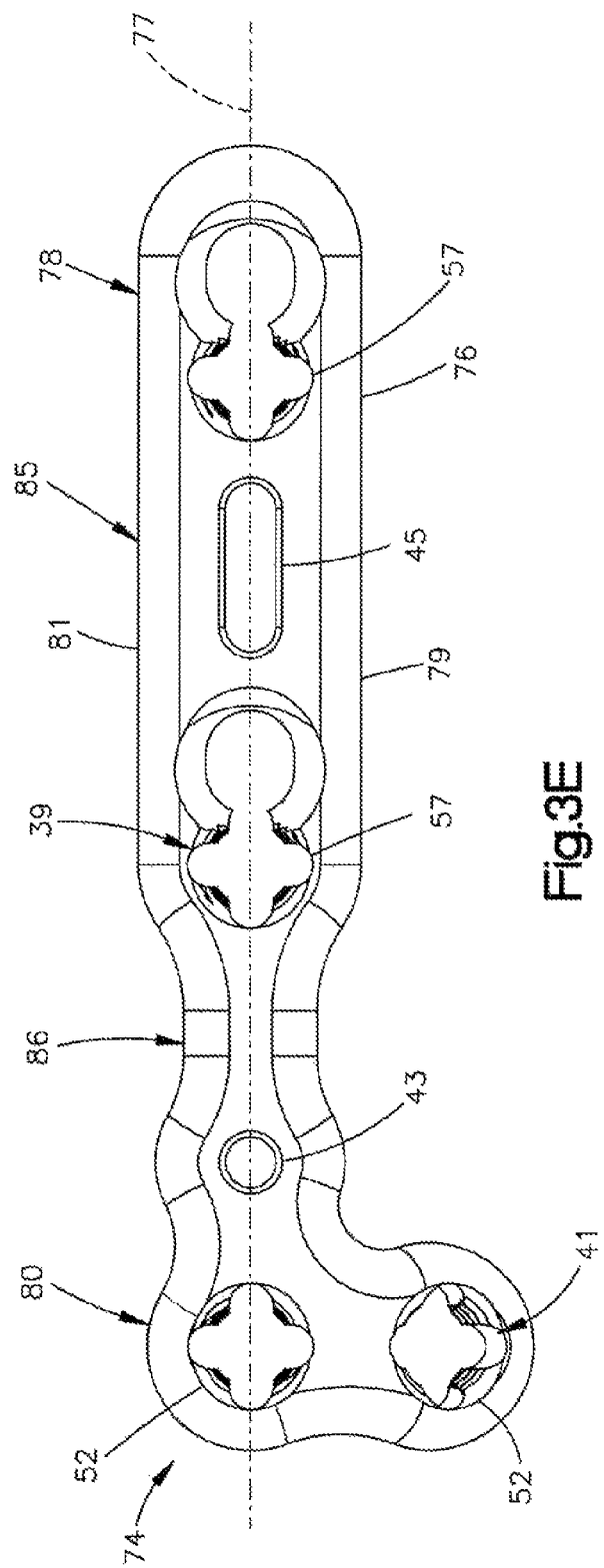
FIG. 3E is a top plan view of a bone fixation plate constructed similar to the bone plate illustrated in FIG. 3A, but in accordance with another embodiment.

Referring to FIG. 3E, the head portion 83 can configured so as to impart an "L" shape onto the plate body 76. In particular, one of the side surfaces 79 of the head portion 83 can be substantially in line with the side surface 79 of the shaft portion 85, while the other side surface 81 of the head portion 83 can be project laterally outward with respect to the side surface 81 of the shaft portion 85. In accordance with the illustrated embodiment, the head portion 83 is not sized to accommodate an aperture 39 contained between the side surface 79 and the longitudinal axis 77. Rather, the head portion 83 defines a first aperture 39 on the longitudinal axis 77, and a second aperture 39 disposed between the longitudinal axis 77 and the side surface 81.

Referring to FIG. 4A, and as described above, certain bone plates can be constructed without a discrete shaft portion, neck portion, and/or head portion. One example of such a bone plate 88 includes a bone plate body 90 that extends substantially along a central longitudinal axis 92, and defines a proximal end 94 and a distal end 96 opposite the proximal end 94 along the longitudinal axis 92. The plate body 90 further defines a bone-facing inner surface 93 and an opposed outer surface 95 spaced from the inner surface 93 along the transverse direction T. The plate body 90 further defines opposed side surfaces 97 and 99 that are spaced from each other along the lateral direction A. The plate body 90 includes a shaft portion 100 that extends between the proximal and distal ends 94 and 96, respectively, and a pair of longitudinally spaced wings 102 and 104 that project laterally out from both side surfaces 97 and 99 of the shaft portion 100. The wing 102 is disposed distal with respect to the wing 104, and extends laterally outward a distance greater than the wing 104, though it should be appreciated that the wing 104 can extend laterally outward a greater distance than the wing 102.

The bone plate 88 includes a plurality of apertures 40 that extend through the plate body 90 in the manner described above. For instance a K-wire slot 45 is disposed distal with respect to a K-wire hole 43. The bone plate 88 further includes a plurality of bone anchor holes 41 that extend through the body 90. For instance, a variable angle hole 52 extends through both lateral sides of the wings 102 and 104. A first variable angle hole 52 further extends through the shaft portion 100 at a location proximal of the K-wire slot 45, and a second variable angle hole 52 extends through the shaft portion 100 at a location proximal of the K-wire hole 43. A combination hole 57 extends through the shaft portion 100 at a location proximal of the K-wire hole 43, and proximal of the second variable angle hole 52. As illustrated in FIG. 4B, the plate body 90 defines the intermediate portion 91 disposed between the k-wire hole 43 and the K-wire slot 45.

The intermediate portion 91 can be coplanar with the remainder of the plate body 90, or can be angularly offset from a remaining portion of the plate body 90 with respect to a longitudinal direction of travel along the bone-facing inner surface 93. In particular, the inner surface 93 is concave at the intermediate portion 91 in accordance with the illustrated embodiment. The plate body 90 can further be curved with respect to a lateral direction along the bone-facing inner surface 93, for instance at the wings 102 and 104 alone or in combination with the shaft portion 100.

Figure 4C:
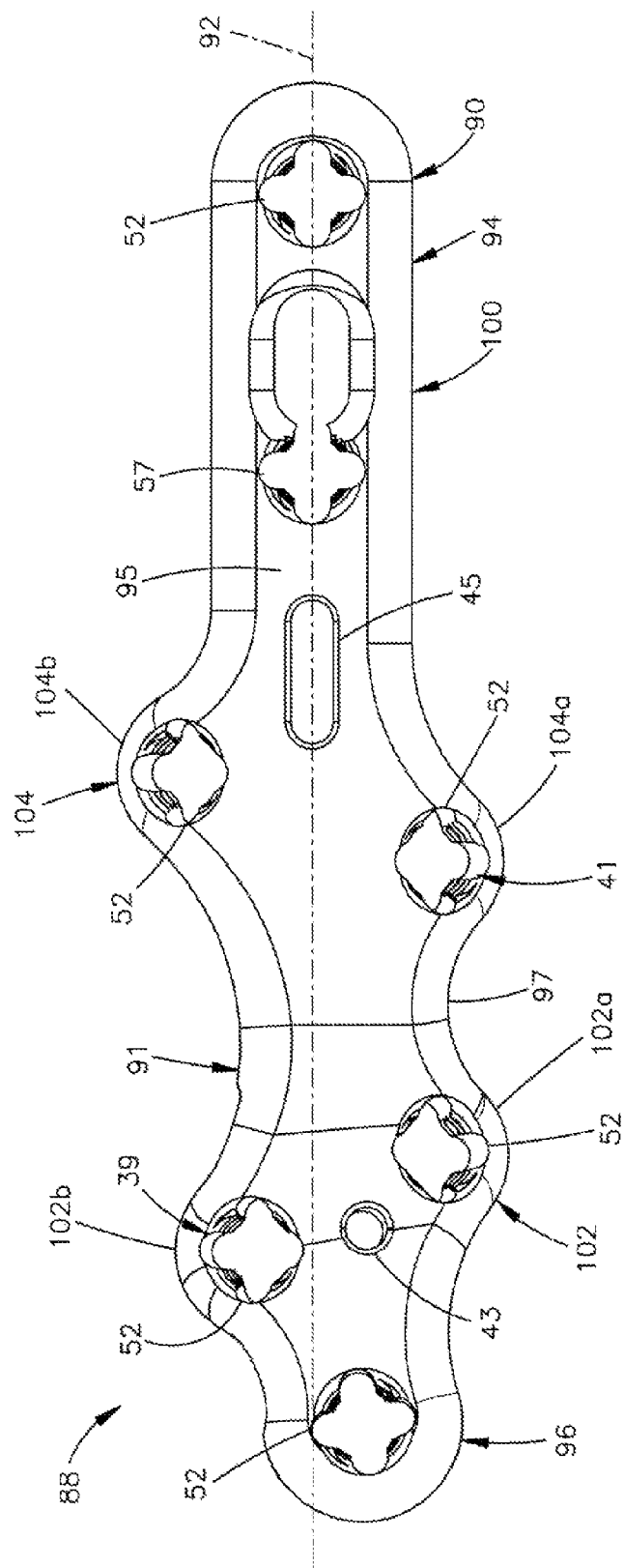
FIG. 4C is a top plan view of a bone fixation plate constructed in accordance with another embodiment.
Figure 4D:
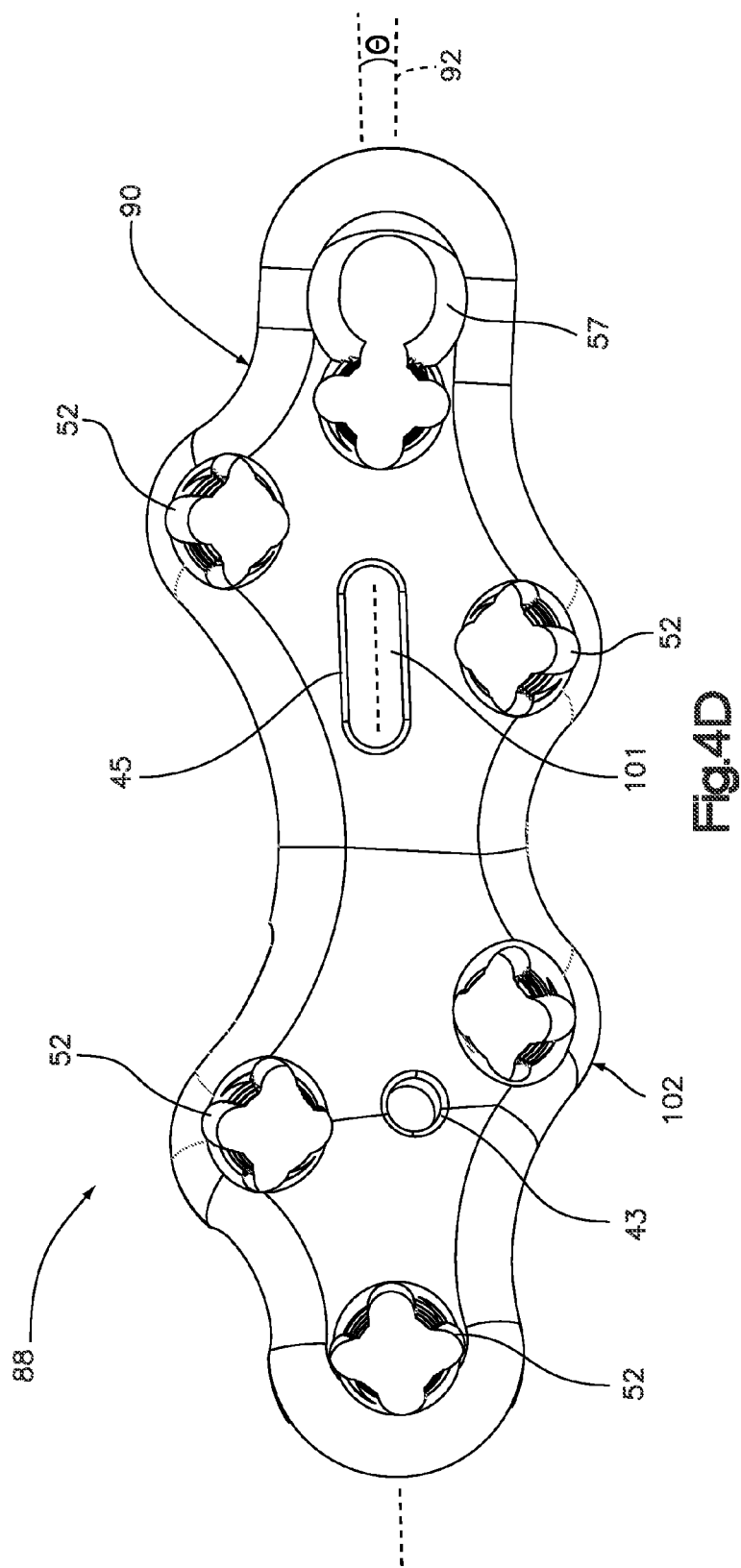
FIG. 4D is a top plan view of a bone fixation plate constructed similar to FIG. 4C, but in accordance with another embodiment.

Referring now to FIG. 4C, it should be appreciated that the K-wire hole 43 can be longitudinally offset with respect to the K-wire slot 45. In particular, the bone plate 88 is constructed substantially as described above with respect to FIG. 4A, however the wings 102 and 104 define respective first lateral extensions 102a and 104a that extend laterally out from the first side surface 97, and respective second lateral extensions 102b and 104b that extend laterally out from the second side surface 99 at a location distal with respect to the first extensions 102 and 104a. Furthermore, the proximal end 94 and the distal end 96 are laterally offset from each other. Accordingly, the K-wire slot 45 extends longitudinally, and the K-wire hole 43 is laterally offset with respect to the K-wire slot 45, such that the K-wire slot 45 and the K-wire hole 43 are not longitudinally aligned. Alternatively, as illustrated in FIG. 4D, the K-wire slot 45 and the K-wire hole 43 can both be angularly offset with respect to the central longitudinal axis 92, and longitudinally aligned with each other.

Figure 4E:
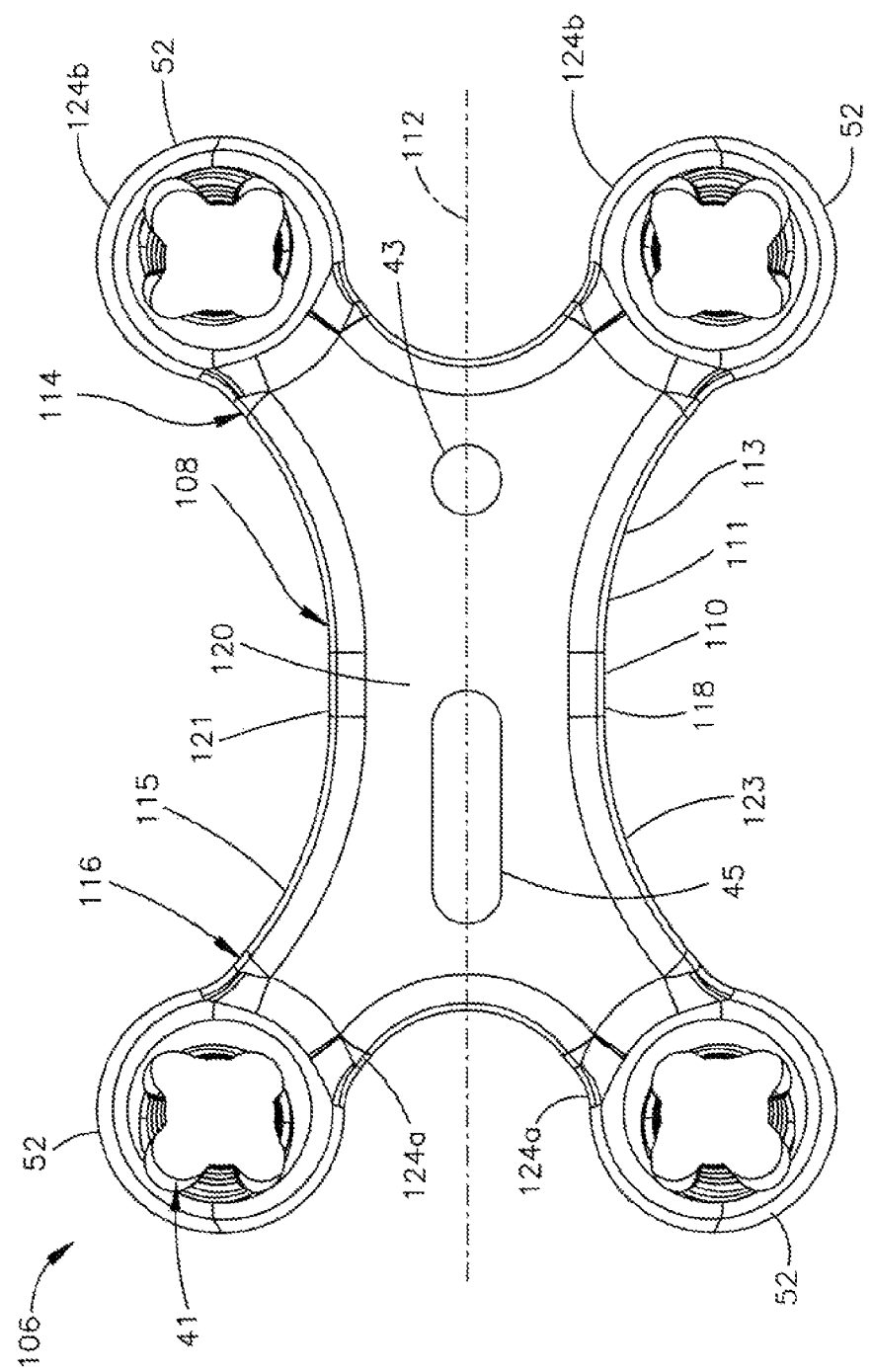
FIG. 4E is a top plan view of a bone fixation plate constructed in accordance with another embodiment.

Referring now to FIG. 4E, an alternatively constructed bone plate 106 includes a bone plate body 108 having a shaft portion 110 that extends substantially along a central longitudinal axis 112, and defines a proximal end 114 and a distal end 116 opposite the proximal end 114 along the longitudinal axis 112. The shaft portion 110 further includes an intermediate portion 111 that extends between the proximal end 114 and the distal end 116. The plate body 108 further defines a bone-facing inner surface 118 and an opposed outer surface 120 spaced from the inner surface 118 along the transverse direction T. The plate body 108 further defines opposed side surfaces 121 and 123 that are spaced from each other along the lateral direction A. The plate body 108 further includes a first pair of laterally opposed flared regions 124a that extend distally and laterally outward from the distal end 116 of the shaft portion 110, and a second pair of laterally opposed flared regions 124b that extend proximally and laterally outward from the proximal end 114 of the shaft portion 110. The shaft portion 110 and the flared regions 124a-b impart a substantial X-shape to the bone plate body 108.

The bone plate 106 includes a K-wire hole 43 that extends through a first portion 113 of the plate body 108, and a K-wire slot 45 that extends through a second portion 115 of the plate body 108 that is disposed proximal with respect to the first portion 113, though as described above it should be appreciated that the K-wire hole 43 can extend through the second portion 115 and the K-wire slot 45 can extend through the first portion 115. The intermediate portion 111 extends between the first and second portions 113 and 115 of the plate body 108. It should further be appreciated that the first portion 113 can include both a K-wire hole 43 and a K-wire slot 45, and the second portion 115 can likewise include both a K-wire hole 43 and a K-wire slot 45 so as to enhance the positional flexibility of the plate 106, and allow for either underlying bone segment 27a or 27b to be translated relative to the other bone segment 27a or 27b. The bone plate 106 further includes a bone anchor hole 41 illustrated as a variable angle hole 52 that extends transversely through each of the flared regions 124a-b. Thus, one or both of the K-wire hole 43 and the K-wire slot 45 can be laterally offset with respect to one or more bone anchor holes 41, up to all of the bone anchor holes 41.

Referring now to FIG. 4F, a substantially linear bone plate 130 constructed in accordance with still another alternative embodiment includes a bone plate body 132 having a shaft portion 134 that extends substantially along a central longitudinal axis 136, and defines a proximal end 138 and a distal end 140 opposite the proximal end 138 along the longitudinal axis 136. The shaft portion 134 further includes an intermediate portion 135 that extends between the proximal end 138 and the distal end 140. The plate body 132 further defines a bone-facing inner surface 142 and an opposed outer surface 144 spaced from the inner surface 142 along the transverse direction T. The plate body 132 further defines opposed side surfaces 145 and 147 that are spaced from each other along the lateral direction A.

The bone plate 130 further includes a K-wire hole 43 and the K-wire slot 45 that extend through respective first and second portions 131 and 133 of the plate body 132. The first portion 131 can be disposed proximal of or distal of the second portion 133, such that the intermediate portion 135 is disposed between the first and second portions. In accordance with the illustrated embodiment, the bone plate 130 includes a plurality of bone anchor holes 41 illustrated as variable angle holes 52 disposed longitudinally outward with respect to the K-wire hole 43 and the K-wire slot 45, such that the intermediate portion 135 is devoid of apertures 40. As illustrated in FIG. 4G, the proximal and distal ends 138 and 140 can flare laterally outward with respect to the intermediate portion 135 as desired.

Referring now to FIGS. 5A-D, it should be appreciated that the bone anchors 30 can be provided as a non-locking bone screw, a locking bone screw, a nail, pin, or any alternatively constructed fastener configured to secure the bone plate 22 to the underlying bone 27. Furthermore, one or more up to all of the bone anchors 30 can be provided as differently constructed bone anchors. For instance, one or more up to all of the bone anchors 30 can be provided as non-locking bone screws configured to be inserted through a bone plate (for instance in the head portion or the shaft portion) while one or more up to all of the bone anchors 30 can be provided as locking bone screws configured to be inserted through a bone plate (for instance in the head portion or the shaft portion).

Referring to FIG. 5A in particular, a bone anchor 30 is illustrated as a non-locking bone screw 150, also known as a cortex screw. The non-locking screw 150 includes a shaft 152 that extends distally from a screw head 153. The shaft 152 can be at least partially threaded or toothed, and thus configured to be secured in the underlying bone 27. As illustrated the shaft 152 defines helical threads 154 on the outer surface thereof. The length of shaft 152 and the configuration of the threads 154 (e.g., pitch, profile, etc.) can vary depending on the application. The shaft 152 defines a tip end 156 that can be self-tapping and/or self-drilling to facilitate implantation of the bone screw 150 into the underlying bone 27. The bone screw 150 can further include a cannula 158 that extends through the head 153 and the shaft 152, and is configured to receive a guide wire that assists in proper placement of the bone screw 150.

The head 153 defines an unthreaded inner engagement surface 155 configured to contact the bone plate 22, and an opposing outer drive surface 157 that includes an engagement member configured to mate with a complementary engagement member of a driving instrument that imparts a rotational movement on the bone screw 150 so as to drive the shaft 152 into the underlying bone 27. During operation, the bone screw 150 is aligned with a bone anchor hole 41 of the type described above, and the shaft 152 is driven through the aligned hole 41 and into the underlying bone 27. The shaft 152 can be driven into the underlying bone 27 until the inner engagement surface 155 abuts the bone plate 22, thereby applying a compression force against the bone plate 22 toward the underlying bone 27, and fixing the bone plate 22 to the underlying bone 27. The non-locking bone screw 150 can thus also be referred to as a compression bone screw. Generally the screw head 153 defines a substantially smooth surface at the inner engagement surface 155, and has any suitable size and geometry corresponding to a select bone anchor hole 41. The shape of head 102 may be, for example, conically tapered, straight-sided, spherical, hemispherical, and the like. In certain instances it may be desirable for the unthreaded engagement surface 155 to abut a corresponding unthreaded interior surface of the bone plate 22 that at least partially defines the bone anchor hole 41.

Referring now to FIGS. 5B-C, a bone anchor 30 is illustrated as a locking bone screw 160 having a head 162 and a shaft 164 extending distally from the head 162 along a central axis 165. The shaft 164 can be at least partially threaded or toothed, and thus configured to be secured in the underlying bone 27. As illustrated the shaft 164 defines helical threads 166 on the outer surface thereof. The length of shaft 164 and the configuration of the threads 166 (e.g., pitch, profile, etc.) can vary depending on the application. The shaft 164 defines a tip end 168 that can be self-tapping and/or self-drilling to facilitate implantation of the bone screw 160 into the underlying bone 27. The bone screw 160 can further include a cannula in the manner described above.

The head 162 defines a drive surface 170 configured to mate with a complementary engagement member of a driving instrument as described above, and a threaded engagement surface 172 configured to mate with corresponding threads of the bone plate 22. The engagement surface 172 defines helical threads 174 that define thread peaks 176 and troughs 178 connected to each other by flanks 180, two adjoining flanks 180 defining a thread angle. The head 162, which is conically shaped as is usual on known locking screws, is typically oriented such that the thread peaks 176 lie on a straight line, such as lines 182 or 184, and thread troughs 178 lie on another straight line, such as lines 186 or 188, wherein the pairs of lines (182, 186) and (184, 188) are substantially parallel to each other, and can be parallel or non-parallel to the central axis 165 of the screw 160. For instance, the outer diameter of the threads 174 can decrease along a direction from the head 162 toward the tip 168. The locking screw 160 can also have a constant thread pitch (the distance from peak to peak, or trough to trough) as measured along the central axis (e.g., 165).

During operation, a bone anchor 30 which can be provided as a non-locking screw 150 or a locking screw 160, can be inserted into one or more, up to all, of the bone anchor holes 41. Locking screws 160 and non-locking screws can be used alone or in combination with each other, in the head portion and/or the shaft portion of the bone plate 22. It should be appreciated that the non-locking screw 150 is configured to compress the bone plate 22 against the underlying bond 27 as it is tightened against the bone plate 22 in the bone anchor hole 41. The locking screw 160 is configured to threadedly mate with a threaded bone anchor hole 41, so as to lock the screw 160 to the bone plate 22, and affixing the bone plate 22 to the underlying bone 27 without causing compression of the bone plate 22 against the bone 27, or otherwise limiting compression of the bone plate 22 against the bone 27.

Figure 5D:
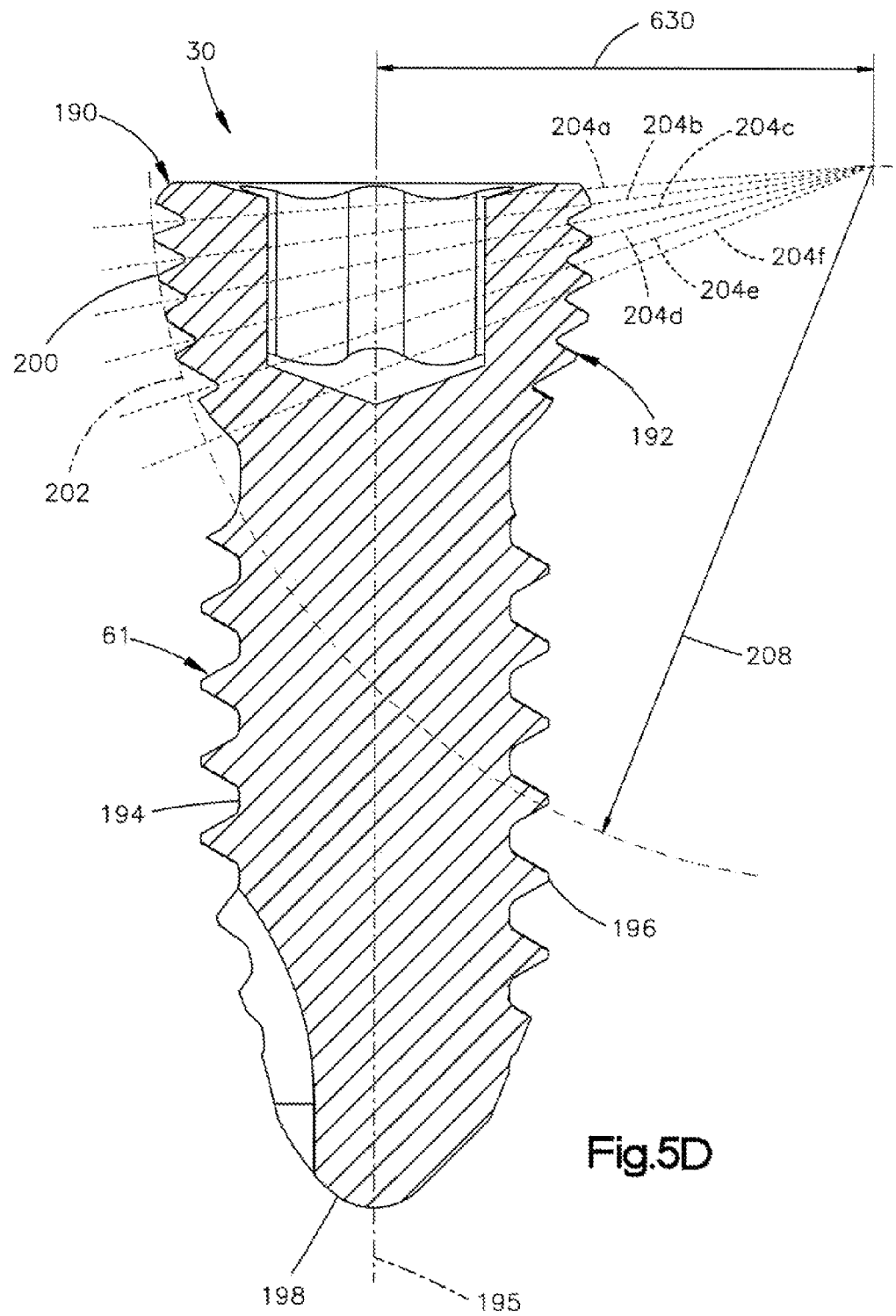
FIG. 5D is a sectional side elevation view of a locking bone anchor constructed in accordance with an alternative embodiment.

Referring now to FIG. 5D, the bone anchor 30 is illustrated as a variable-angle locking screw 190 having a head 192 and a shaft 194 extending distally from the head 192 along a central axis 195. The shaft 194 can be at least partially threaded or toothed, and thus configured to be secured in the underlying bone 27. As illustrated the shaft 194 defines helical threads 196 on the outer surface thereof. The length of shaft 194 and the configuration of the threads 196 (e.g., pitch, profile, etc.) can vary depending on the application. The shaft 194 defines a tip end 198 that can be self-tapping and/or self-drilling to facilitate implantation of the bone screw 190 into the underlying bone 27. The bone screw 190 can further include a cannula in the manner described above.

The screw head 192 is illustrated as at least partially spherical, and defines threads 200 on an outer surface thereof. The threads 200 can be double lead threads, and define an arc-shaped profile 202 (e.g., non-linear or curved) along a radius of curvature. The threads 200 thus define trough profile lines 204a-f that intersect a center 206 of the radius of curvature, which is a distance 208 (measured perpendicularly) from the central axis 195 of the screw 190. If, for example, the radius is 624 is 10 mm, the distance 208 may be about 8.2 mm for a 2.4 mm screw (the 2.4 mm refers to the major diameter of shaft 194). It should be appreciated, however, that as the radius of curvature increases, the head 192 becomes less and less spherical in shape, causing the thread profile to become more and more aligned with a straight line as described above with respect to the locking screw 160.

The thread pitch can be constant as measured along the radius of curvature, but can vary from narrow-to-wide-to-narrow as measured along the central axis 195 in a distal direction from the head 192 toward the tip 198. This thread profile allows the variable-angle locking screw to engage a variable angle hole 52 at a selectable angle within a range of angles while maintaining the same degree of contact with the bone plate regardless of the angle chosen. That is, the angle of the screw 190 with respect to the central axis of the bone plate hole 52 within the permissible range of angles does not affect the engagement of the screw head thread 200 with respect to the interior surface 55 of the plate hole 52. A tight lock is thus obtained between the screw 190 and the bone plate 22 regardless of the angle (within the range of angles) at which the screw 190 is inserted into the variable angle hole 52, because the threads 200 engage the columns 56 of thread segments 58 in precisely the same manner, ensuring a good fit.

The non-locking bone screw 150, the locking bone screw 160, and the variable-angle locking bone screw 190 are further described in more detail in U.S. Patent Application Publication No. 2008/0140130, published Jun. 12, 2008, the disclosure of which is hereby incorporated by reference as if set forth in its entirety herein.

Figures 6A, 6B:
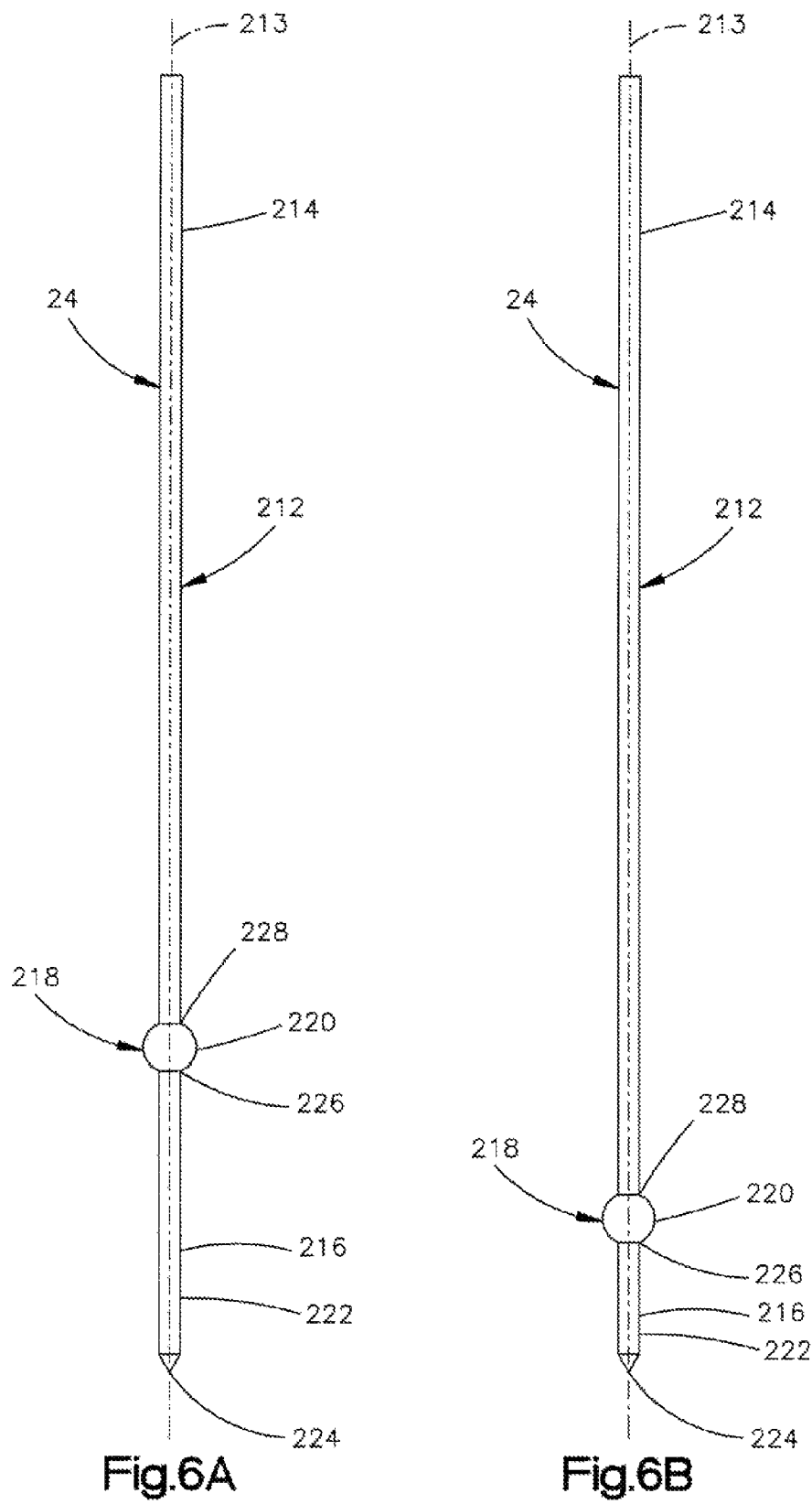
FIG. 6A is a side elevation view of the K-Wire illustrated in FIG. 1A.
FIG. 6B is a side elevation view of a K-wire constructed in accordance with an alternative embodiment.

Referring now to FIG. 6A, the K-wire 24 provides a temporary fixation member having a wire body 212 that is longitudinally elongate along a central axis 213. The wire body 212 defines a proximal portion 214 and an opposing distal portion 216 that is spaced from the proximal portion 214 along the central axis 213. The K-wire 24 includes an engagement member 218 that is attached to the wire body 212 and separates the distal portion 216 from the proximal portion 214. The proximal and distal portions 214 and 216 can be cylindrical in shape or can define any suitable alternative shape as desired. The engagement member 218 defines an outer engagement surface 220 that can be spherical as illustrated, or can define any suitable alternative shape. For instance, the outer surface 220 can be round (for instance cylindrical or otherwise curved), polygonal, or the like, and thus suitable to be engaged by the forceps 26.

The proximal portion 214 of the K-wire is configured to be engaged by an insertion tool so as to be rotatably driven. The distal portion 216 of the K-wire 24 is configured to be inserted through an aperture 39 of the bone plate 22, and temporarily driven into and thus fixed to the underlying bone 27. In particular, the K-wire 24 includes helical threads 222 at the distal portion 216 and a tapered or pointed driving end or tip 224 that can present one or more cutting flutes as desired such that the K-wire 24 can be self-tapping. The tip 224 is thus configured to be driven into an underlying bone to a depth such that rotation of the K-wire 24 causes the threads 222 to drive into the bone 27. The threads 222 extend along all or a region of the distal portion 216, for instance from a location proximate to the tip 224 a location proximate to the engagement member 218. The threads 222 can extend to the engagement member 218, or can terminate at a location spaced distally from the engagement member 218. Accordingly, the K-wire 24 can be driven into underlying bone to a depth that causes the abutment member 28 to apply compression against the bone plate 22, or to a depth that causes the abutment member 28 to be spaced from the bone plate.

The wire body 212 can be sized and shaped as desired, and in accordance with the illustrated embodiment is dimensioned such that the diameter of the proximal portion 214 and the outer diameter of the threads 222 are both approximately 1.25 mm, though it should be appreciated that the diameter of the proximal end 24 and the outer diameter threads can be sized as desired, for instance at approximately 1.6 mm, any distance between approximately 1.25 mm and approximately 1.6 mm, or any distance less than approximately 1.25 mm or greater than approximately 1.6 mm. In this regard, it should be appreciated that the outer diameter or cross-sectional dimension of the threads 222 can be substantially equal to, greater than, or less than the diameter or cross-sectional dimension of the proximal portion 214. As illustrated in FIG. 6A, the distal portion 216 can have a first length, and as illustrated in FIG. 6B, the distal portion 216' of another K-wire 24 can have a second length less than the first length of the distal portion 216. The distal portions of the K-wires 24 can have any length as desired, such as between approximately 1 mm and approximately 40 mm, or any alternative length suitable for extending through the bone plate and being fixed to the underlying bone 27.

With continuing reference to FIG. 6A, the engagement member 218 can include an outer surface 220 that is spherical as illustrated, but can have any shape suitable for receiving a force that biases the K-wire 24 and the underlying bone in a desired direction as defined by the bone plate aperture 40 through which the distal portion 216 extends. For instance, the outer surface 220 can be cylindrical in shape about the central axis 213, or about any axis coincident with or intersecting the central axis 213. In this regard, the outer surface 220 can define a circular cross-section, and oval cross-section, or any alternative curved or polygonal shape, regular or irregular, in cross-section. Accordingly, the outer surface 220 can define a curved surface in any direction as desired, or can be polygonal, regular or irregular, angled, or can define any alternative shape as desired. The spherical outer surface 220 allows the forceps 42 to engage the engagement member 218 at variable approach angles, as described in more detail below. The engagement member 218 can be integrally or discretely attached (e.g., welded) to the wire body 212.

The outer surface 220 of the engagement member 218 defines a distal bone-plate facing end 226, an opposing proximal end 228, and an intermediate engagement surface 230 disposed between the distal end 226 and the proximal end 228. As described above with respect to the outer surface 220, the engagement surface 230 can define a circular cross-section, and oval cross-section, or any alternative curved or polygonal shape, regular or irregular, in cross-section. Accordingly, the outer surface 220 can define a curved surface in any direction as desired, or can be polygonal, regular or irregular, angled, or can define any alternative shape as desired. The outer surface 220 can defines a diameter or cross-sectional dimension greater than that of the distal portion 216 of the wire body 212, and in particular a lateral dimension that is greater than that of the distal portion 216, and greater than the aperture 45 through which the distal portion 216 of the K-wire 24 is inserted. Accordingly, the engagement member 218 can provide a stop that is configured to abut the bone plate 22 so as to limit the insertion depth of the K-wire 24 into the underlying bone 27.

The K-wires 24 of the bone fixation system 20 can be identically constructed and configured to be inserted in either the K-wire hole 43 or the K-wire slot 45 as described above. Alternatively, if the hole 34 and the slot 45 define different lateral dimensions, the K-wires 24 can be provided with different diameters or lateral dimensions, one of which is equal to the diameter or lateral dimension of the hole 34 and the other of which is equal to the lateral width of the slot 45. The K-wires 24 can be referred to as temporary fixation members, temporary bone anchors or temporary bone fixation members, as they are driven into the underlying bone 27 and subsequently removed prior to completion of the surgical or bone fixation procedure. The bone anchors 30, on the other hand, can be referred to as permanent bone anchors or permanent bone fixation members, as they remain implanted in the underlying bone 27 after completion of the surgical procedure, even though the bone anchors 30 can be removed in a second subsequent surgical procedure.

Figure 7A:
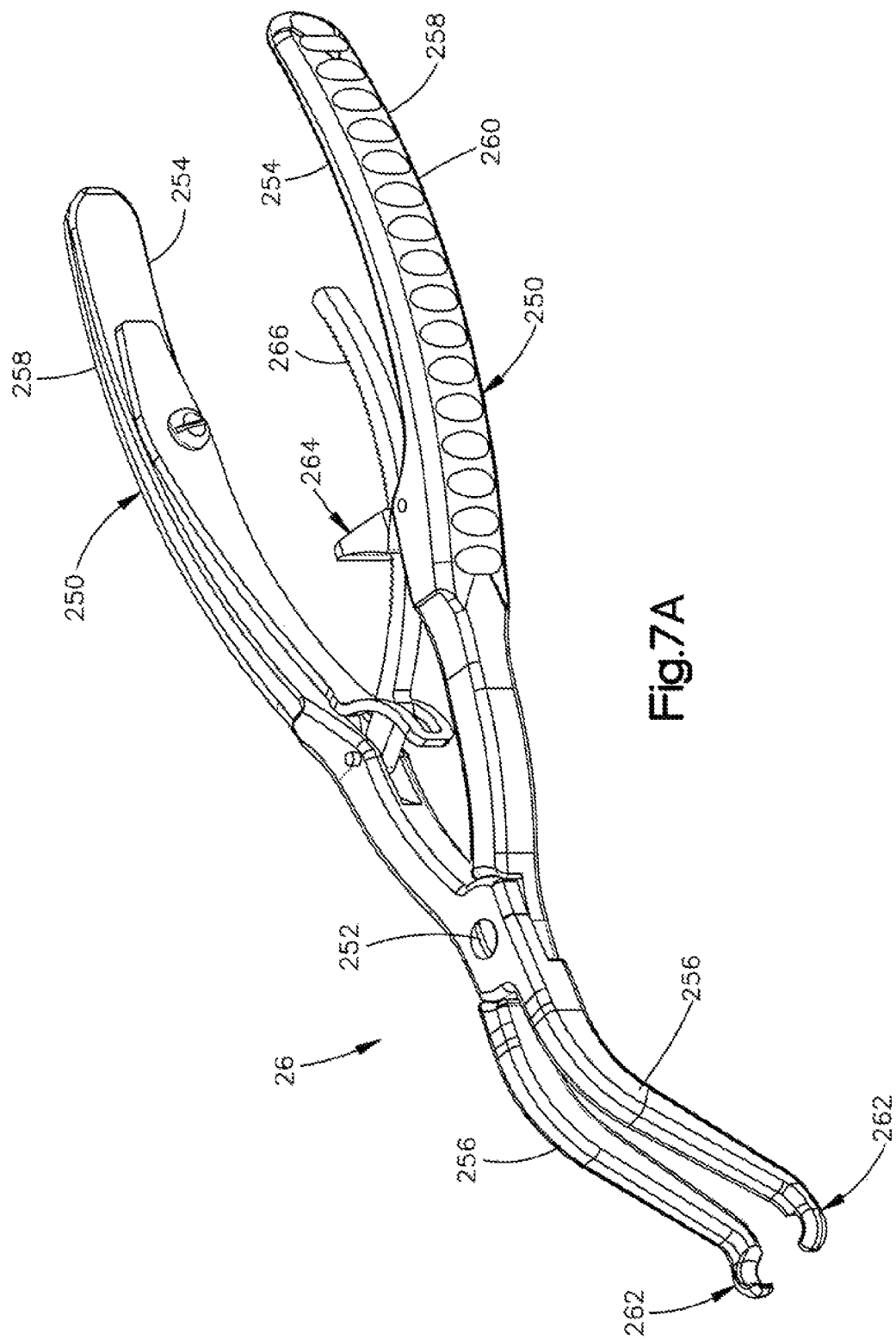
FIG. 7A is a perspective view of the forceps illustrated in FIG. 1A.
Figure 7B:
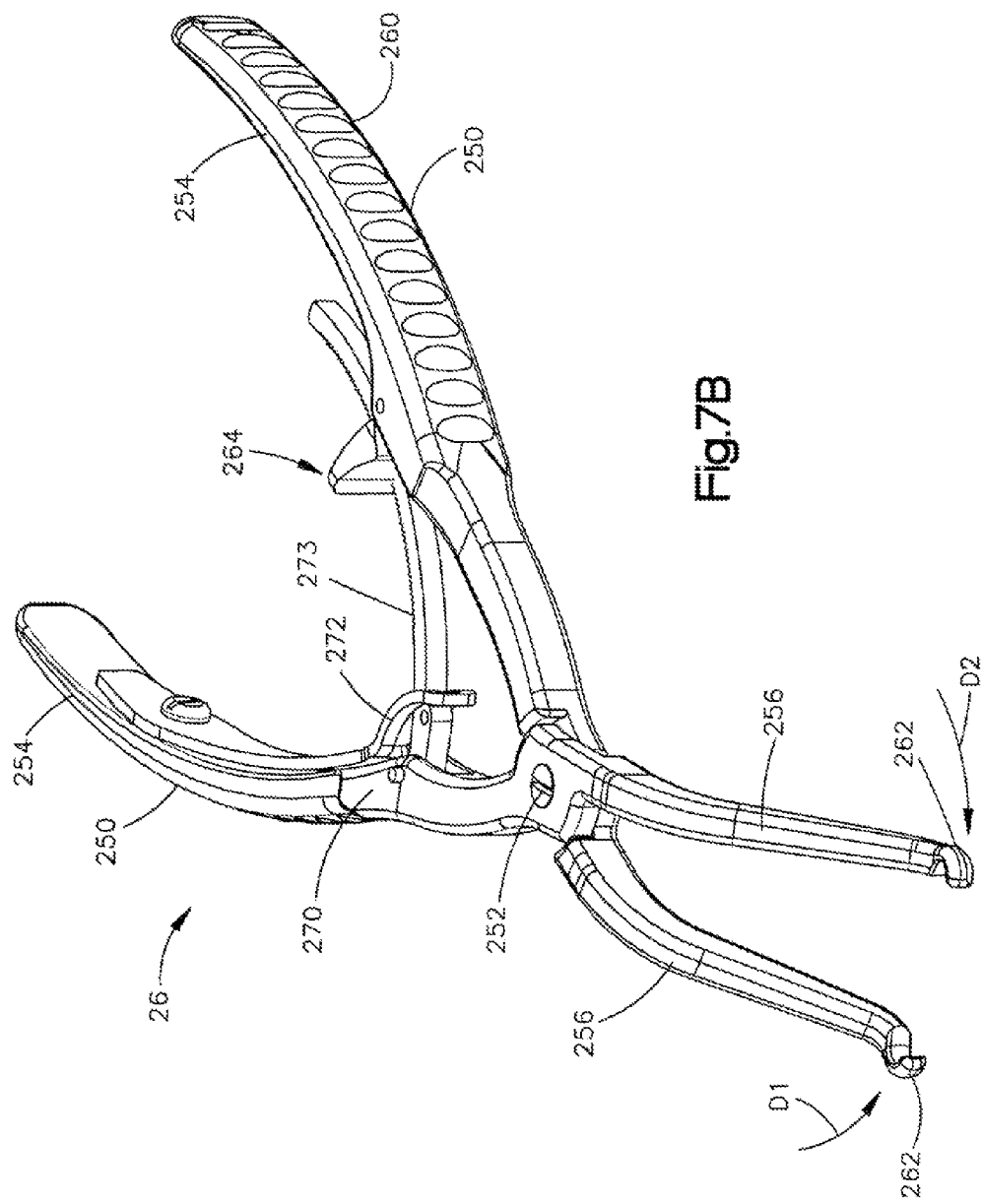
FIG. 7B is a perspective view of the forceps illustrated in FIG. 7A shown in an open configuration.

Referring now to FIGS. 7A-C, the forceps 26 includes a pair of arms 250 pivotally connected together at a joint 252, which divides the arms 250 between a proximal portion 254 and an opposing distal portion 256. The proximal portion 254 of each arm 250 defines a handle 258 that can present an outer grip surface 260, while the distal portion 256 of each arm 250 defines an engagement member 262 that is configured to engage the outer surface 220 of the engagement member 218 of a respective K-wire 24. The proximal portion 254 of each arm 250 is generally planar, while the distal portion 256 of each arm 250 extends inward and out of plane with respect to the proximal portion 254. In particular, the distal end 256 is curved such that the engagement members 262 extend toward the engagement member 218 when the handle 258 is spaced above (or outward from) the engagement member 218.

The arms 250 are pivotally connected, such that when the handles 258 are brought together, the engagement members 262 are likewise brought together, and when the handles 258 are moved apart, the engagement members are likewise moved apart. Referring also to FIG. 7D, the forceps 26 include a ratchet 264 that causes the arms 250 to move together incrementally. For instance, one of the arms 250 carries a rack 266 that carries a plurality of teeth 268 extending out from a rack body 269. In accordance with the illustrated embodiment, the rack 266 extends from the proximal 254 of the corresponding arm 250, and is pivotally connected to the arm 250 at a joint 270. The arm 250 that carries the rack 266 also carries a guide 272 that defines a guide channel 273 that receives the rack 266.

The opposing arm 250 carries a pair of opposed channel walls 274 that define a channel 276 therebetween. The channel 276 receives the rack 266 which is directed into the channel 276 by the guide 272, such that the rack 266 is translatable within the channel 276. The channel walls 274 further carry at least one tooth 278 that can be spring-biased into engagement with the teeth 268 of the rack 266. The tooth 278 and the teeth 268 can be configured such that the tooth 278 rides over the teeth 268 as the handles 258 are brought together. The spring force provides resistance as the tooth 278 rides along each tooth 268, and biases the tooth 278 into the valleys between the adjacent teeth 268 so as to provide tactile feedback as the handles 258, and thus the engagement members 262 incrementally close. The teeth 268 and 278 can further be configured such that interference prevents the tooth 268 from riding along the teeth 278 when a separation force is applied to the handles 258, if desired. The tooth 278 can include an engagement surface 279 that can be depressed by a user against the spring force to bring the tooth 278 out of engagement with the teeth 268 so as to allow for separation of the handles 258, and thus separation of the engagement members 262. Alternatively, the teeth 268 and 278 can be configured such that the tooth 268 incrementally rides along the teeth 278 in the manner described above both when the handles 268, and thus the engagement members 262 are separated, and when the handles 268, and thus the engagement members 262, are brought together.

Referring now also to FIG. 7E, each engagement member 262 defines an inner engagement surface 280 that faces the corresponding inner engagement surface 280 of the other arm 250, and an opposing outer surface 282. When the engagement members 262 each engage a complementary engagement member 218 of a corresponding K-wire 24, the inner surfaces 280 can abut the respective outer surface 220 of the engagement members 218.

In accordance with the illustrated embodiment, each engagement member 262 includes a pocket 284 that projects into the inner surface 280. The pocket 284 can have any size and shape as desired, and thus presents a corresponding inner engagement surface 286 that can have any size and shape as desired, such that the engagement surface 286 is configured to apply a compressive force on a respective engagement member 218 of a K-wire 24 that biases the corresponding K-wire 24 inwardly toward the opposing K-wire 24. The pocket 284 has an open outer end 285 configured to at least partially receive the engagement member 218 of the K-wire 24 along a direction toward the inner engagement surface 286.

In accordance with the illustrated embodiment, the engagement surface 286 extends along two radii of curvature that are directed substantially perpendicular to each other. One radius of curvature can be greater than the other, such that the engagement surface 286 defines a vertical curvature substantially equal to that of the outer surface 220 of the engagement member 218 of the K-wire 24. The engagement surface 286 can define a horizontal radius of curvature that is greater than that of the vertical radius of curvature, such that the engagement surface 286 has an average curvature that is greater in the vertical direction than in the horizontal direction. It should be appreciated that the vertical curvature can be circular and sized and shaped substantially identical to the outer surface 220 of the respective engagement member 218. The horizontal average curvature can be defined by a continuously curved surface, one or more angled surfaces, or a straight surface (thus defining an infinite radius of curvature). The curved surface 286 allows the pocket 284 to reliably receive the respective engagement member 218 at varying approach angles. Alternatively, the horizontal curvature can be substantially identical to the vertical curvature, and thus substantially identical to the spherical outer surface 220 of the engagement member 218 of the K-wire 24.

Referring also again to FIGS. 1A-B and 2H, during operation, the bone plate 22 is aligned with and placed over or on the underlying bone 27 such that the intermediate portion 35 extends over the bone gap 28, at least one bone anchor hole 41 is aligned with the bone segment 27a, and at least one bone anchor hole 41 is aligned with the bone segment 27b. One of the K-wires 24 is driven through the K-wire hole 43 and into one of the underlying bone segments 27a or 27b, and the other K-wire 24 is driven through the K-wire slot 45 and into the other bone segment 27b or 27a. The K-wire 24 is driven through a location of the K-wire slot 45 at a location spaced from the leading edge 71 such that the K-wire 24 is translatable in the slot 45 toward the leading edge 71. The bone gap site can be medically imaged to ensure that the bone plate 22 is properly aligned with the underlying bone 27. Next, the handles 258 are separated until the engagement members 262 are likewise separated a distance greater than that of the engagement members 218 of the K-wires 24, such that the engagement surfaces 286 fit over the engagement members 218.

Next, the forceps 26 are actuated so as to drive the distal portions 256 of the arms 250 together such that the engagement surfaces 286 move along a first direction D1 (see FIG. 7B) until they are brought into initial engagement with and abut or contact the respective outer engagement surfaces 220 of the engagement members 218. The first direction is angularly offset with respect to the central axis 213 of the wire body 212, and can for instance be substantially perpendicular with respect to the central axis 213. The pocket 284 at least partially receives the engagement member 218 in its open end 285, and thus does not encircle the engagement member 218.

Continued actuation of the forceps 26 so as to drive the engagement members 262 along the first direction causes the engagement surfaces 286 to apply a compressive force to the outer engagement surface 220 of the K-wire 24 disposed in the slot 45, thereby biasing the K-wire inward and causing the K-wire 24 to translate in the slot toward the leading edge 71 toward the opposing K-wire 24. The opposing K-wire 24 can be fixed in position in the K-wire hole 43, such that the movement of the K-wire 24 disposed in the slot 45 toward the opposing K-wire causes the corresponding underlying bone segment 27a or 27b to translate toward the other bone segment, thereby reducing the bone gap 28 as illustrated in FIG. 1B. In this regard, it should be appreciated that the engagement member 262 of the forceps 26 can be referred to as a reduction engagement member. Thus, it can be said that at least one of the K-wires 24 is translatable relative to the other K-wire 24 which may be fixed in position. Referring also to FIG. 9, once the bone gap 28 has achieved a desired reduction, at least one bone anchor 30 can be driven into a bone anchor hole 41 into the bone segment 27a, and at least one bone anchor 30 can be driven into a bone anchor hole 41 into the bone segment 27b, thereby fixing the bone segments 27a-b in their reduced configuration. The K-wires 24 can then be removed once the bone anchors 30 have fixed the bone plate 22 to the underlying bone 27. The engagement members 218 of the K-wires 24 can be brought together to a minimum retracted distance of X1 (see FIG. 8B), which is achieved when the engagement members 218 are received in the pockets 284 and abut each other.

It should be appreciated in accordance with an alternative embodiment that the K-wire hole 23 can be replaced with a dedicated K-wire slot 45, or that a K-wire slot 45 can be added on the side of the intermediate portion 35 that includes the K-wire hole 43. Thus, the bone plate 22 can include a pair of K-wire slots 45 disposed on opposed sides of the intermediate portion 35 of the bone plate 22. Both K-wires 24 can be inserted through respective K-wire slots 45 at a location spaced from the respective leading edges 71, such that both K-wires 24 are translatable within their respective slots 45 toward each other. Thus, it can be said that the both K-wires 24 are movable relative to each other. In accordance with still another embodiment, one of the K-wires 24 can be disposed adjacent the leading edge 71, or one of the K-wires can be driven into the bone 27 to a depth that causes the distal bone-plate facing end 226 to compress against the bone plate 22, thereby fixing the K-wire in position. Thus, engagement between the K-wire 24 and the bone plate 22 can prevent the K-wire from translating within the bone plate 22 while the other K-wire 24 is free to translate relative to the other K-wire 24 in the manner described above.

It should be appreciated that the K-wire slot 43 and hole 45 define respective cross-sections suitable for receiving K-wires 24, but less than the cross-sections of the bone anchors 30, such that the K-wire hole 43 and slot 45 are dedicated to receive only K-wires 24. However, it should be further appreciated that the K-wire hole 23 and the K-wire slot 25 can be multipurpose, and configured to also receive a bone anchor 30. For instance, either or both of the K-wire hole 23 and the K-wire slot 25 can be provided as a bone anchor hole 41 each sized to receive a bone anchor 30 in the manner described above.

In particular, one or both of the K-wires 24 can be inserted through a bone anchor hole 41 an opposed sides of the intermediate portion and driven into the underlying bone. The K-wires 24 have a diameter or cross-sectional dimension less than that of the bone anchor holes 41 in either or both of the lateral and longitudinal direction. Accordingly, one or both of the K-wires 24 can be initially driven into the underlying bone 21 at a location spaced from the leading edge of the hole 41 (portion of the interior surface that is closest to the opposing K-wire hole), such that one or both of the K-wires 24 is translatable within the respective hole 41 toward the other K-wire 24, thereby reducing the bone gap 28 in the manner described above. It should be appreciated that one of the K-wires 24 can be initially driven into the underlying bone 21 at a location adjacent to the leading edge of the hole 41 such that the leading edge prevents the K-wire 24 from translating toward the opposing K-wire 24. Alternatively, one of the K-wires 24 can be driven into the bone 27 to a depth that causes the distal bone-plate facing end 226 to compress against the outer surface 40 of the bone plate 22, thereby fixing the K-wire 24 in position, while the opposing K-wire 24 can translate within the bone anchor hole 41 as desired.

Thus, it should be appreciated that the bone plate 22 can include at least one K-wire slot 25 which can be in the form of a bone anchor hole 41, dedicated K-wire slot 45, or any alternatively constructed aperture 40 extending through the bone plate 22 and having a dimension greater than the cross-sectional dimension of the distal portion 216 of the K-wire 24, thus allowing the K-wire 24 to translate within the slot 25. The bone plate can further include at least one K-wire hole 23 which can be in the form of a bone anchor hole 41, dedicated K-wire hole 43, dedicated K-wire slot 45, or any alternatively constructed aperture 40, at least partially defined by a surface (which can be an interior surface such as the interior surface 55 illustrated in FIG. 2A or an outer bone plate surface 40) that is configured to prevent the K-wire hole 43 from translating toward the opposing K-wire 24.

It should be further appreciated that the methods described herein can include the steps of inserting the K-wires 24 into the underlying bone segments 27a-b without first placing a bone fixation plate over the bone segments, such that the forceps 26 can actuate one or both the K-wires 24 in the manner described herein to adjust the K-wires 24, and thus the underlying bone segments 27a-b, from a first relative position to a second different relative position so as to correspondingly adjust the size of the bone gap 28.

Referring now to FIG. 8A, it should be appreciated that the forceps 26 provides an instrument that can be configured to reduce the bone gap 28 in the manner described above, and can further be configured to distract the bone segments 27a-b. Thus, whether the bone gap 28 is reduced, or the bone segments 27a-b are distracted, it should be appreciated that at least one or both of the bone segments 27a-b are moved from a first position in relation to each other to a second relative position in relation to each other. The forceps 26 are configured to bias at least one of the K-wires 24 toward the other K-wire so as to change the size of the bone gap 28. In particular, the engagement member 262 defines the inner pocket 284 in the manner described above. Each engagement member 262 further defines a second outer pocket 300 that is configured to apply a force to the respective K-wire 24 that biases the K-wire 24 in a direction away from the opposing K-wire 24. The outer pockets 300 thus face away from each other, and are offset (e.g., recessed) from the pockets 284 with respect to the first direction of travel and a second direction of travel D2 (see FIG. 8A) opposite the first direction D1. The pockets 300 can have any size and shape as desired, and thus presents a corresponding outer engagement surface 302 that can have any size and shape as desired, such that the engagement surface 302 is configured to apply a distractive force on a respective engagement member 218 of a K-wire 24 that biases the K-wire 24 outward away from the opposing K-wire 24. In accordance with the illustrated embodiment, the outer pocket 300 is shaped substantially identically with respect to the inner pocket 284. Thus, the outer pocket 300 has an open outer end 301 configured to at least partially receive the engagement member 218 of the K-wire 24 along a direction toward the outer engagement surface 302.

In accordance with the illustrated embodiment, the outer engagement surface 302 extends along two radii of curvature that are directed substantially perpendicular to each other. One radius of curvature can be greater than the other, such that the engagement surface 302 defines a vertical curvature that corresponds to that of the outer surface 220 of the engagement member 218 of the K-wire 24. The engagement surface 302 can define a horizontal radius of curvature that is greater than that of the vertical radius of curvature, such that the engagement surface 302 has an average curvature that is greater in the vertical direction than in the horizontal direction. It should be appreciated that the vertical curvature can be circular and sized and shaped substantially identical to the outer surface 220 of the respective engagement member 218. The horizontal average curvature can be defined by a continuously curved surface, one or more angled surfaces, or a straight surface (thus defining an infinite radius of curvature). The curved surface 302 allows the pocket 300 to reliably receive the respective engagement member 218 at varying of approach angles. Alternatively, the horizontal curvature can be substantially identical to the vertical curvature, and thus substantially identical to the spherical outer surface 220 of the engagement member 218 of the K-wire 24.

Referring also again to FIGS. 1A-B, 2H, and 8B, during operation, the bone plate 22 is placed over the underlying bone 27 such that the intermediate portion 35 extends over the bone gap 28, at least one bone anchor hole 41 is aligned with the bone segment 27a, and at least one bone anchor hole 41 is aligned with the bone segment 27b. One of the K-wires 24 is driven through the K-wire hole 43 and into one of the underlying bone segments 27a or 27b, and the other K-wire 24 is driven through the K-wire slot 45 and into the other bone segment 27b or 27a. The K-wire is driven through a location of the K-wire slot 45 at a location spaced from the trailing edge 73 such that the K-wire 24 is translatable in the slot 45 toward the trailing edge 73. Next, the handles 258 are brought together so that the pockets 300 are separated a distance equal to or greater than Y1, which is the minimum distance achievable between the pockets 300 when the pockets 284 receive respective engagement members 218. It should be appreciated that the minimum distance Y1 is reduced when the pockets 284 are devoid of engagement members 218. The distance Y1 is less than the distance between the engagement members 218 of the K-wires 24 so that the engagement surfaces 302 fit between the engagement members 218. Next, the distal portions 256 of the arms 250 are brought away from each other along the second direction until the engagement surfaces 302 are brought into initial engagement with and abut or contact the respective outer engagement surfaces 220 of the engagement members 218. The second direction is angularly offset with respect to the central axis 213 of the wire body 212, and can for instance be substantially perpendicular with respect to the central axis 213. The pocket 300 receives the engagement member 218 in its open end 301, and thus does not encircle the engagement member 218.

Further actuation of the distal portions 256 away from each other in the second direction causes the engagement surfaces 302 to bias the outer engagement surface 220 of the K-wire 24 disposed in the slot 45 outward, thereby causing the K-wire 24 to translate in the slot 45 toward the trailing edge 73 away from the opposing K-wire 24. The opposing K-wire 24 can be fixed in position in the K-wire hole 43, such that the movement of the K-wire 24 disposed in the slot 45 away the opposing K-wire causes the corresponding underlying bone segment 27a or 27b to translate away from the other bone segment, thereby distracting the bone gap 28 from a position, for instance illustrated in FIG. 1B to a position illustrated in FIG. 1A. In this regard, it should be appreciated that the engagement member 262 of the forceps 26 can also be referred to as a distraction engagement member. Once the bone gap 28 has achieved a desired distraction, at least one bone anchor 30 can be driven into a bone anchor hole 41 into the bone segment 27a, and at least one bone anchor 30 can be driven into a bone anchor hole 41 into the bone segment 27b, thereby fixing the bone segments 27a-b in their reduced configuration.

It should be appreciated in accordance with an alternative embodiment that the K-wire hole 23 can be replaced with a dedicated K-wire slot 45, or that a K-wire slot 45 can be added on the side of the intermediate portion 35 that includes the K-wire hole 43. Thus, the bone plate 22 can include a pair of K-wire slots 45 disposed on opposed sides of the intermediate portion 35 of the bone plate 22. Both K-wires 24 can be inserted through respective K-wire slots 45 at a location spaced from the respective trailing edges 73, such that both K-wires 24 are translatable within their respective slots 45 away from each other. Thus, it can be said that the both K-wires 24 are movable relative to each other. In accordance with still another embodiment, one of the K-wires 24 can be disposed adjacent the trailing edge 73, or one of the K-wires can be driven into the bone 27 to a depth that causes the distal bone-plate facing end 226 to compress against the bone plate 22, thereby fixing the K-wire in position. Thus, engagement between the K-wire 24 and the bone plate 22 can prevent the K-wire from translating within the bone plate 22 while the other K-wire 24 is free to translate relative to the other K-wire 24 in the manner described above.

It should be appreciated that the K-wire slot 43 and hole 45 define respective cross-sections suitable for receiving K-wires 24, but less than the cross-sections of the bone anchors 30, such that the K-wire hole 43 and slot 45 are dedicated to receive only K-wires 24. However, it should be further appreciated that the K-wire hole 23 and the K-wire slot 25 can be multipurpose, and configured to also receive a bone anchor 30 in the manner described above.

Thus, it should be appreciated that the bone plate 22 can include at least one K-wire slot 25 which can be in the form of a bone anchor hole 41, dedicated K-wire slot 45, or any alternatively constructed aperture 40 extending through the bone plate 22 and having a dimension greater than the cross-sectional dimension of the distal portion 216 of the K-wire 24, thus allowing the K-wire 24 to translate within the slot 25. The bone plate 22 can further include at least one K-wire hole 23 which can be in the form of a bone anchor hole 41, dedicated K-wire hole 43, dedicated K-wire slot 45, or any alternatively constructed aperture 40, at least partially defined by a surface (which can be an interior surface such as the interior surface 55 illustrated in FIG. 2A or an outer bone plate surface 40) that is configured to prevent the K-wire hole 43 from translating away from the opposing K-wire 24.

It should be appreciated that the reduction pocket 284 and the distraction pocket 300 have been illustrated in accordance with various embodiments, and that the forceps 26 can include the reduction pocket 284 alone or in combination with the distraction pocket 300, or can alternatively include the distraction pocket 300 without the reduction pocket 284. Furthermore, it should be appreciated that the engagement member 262 can be constructed in accordance with any desired embodiment including any suitable reduction engagement surface and/or a distraction engagement surface.

Figure 8B:
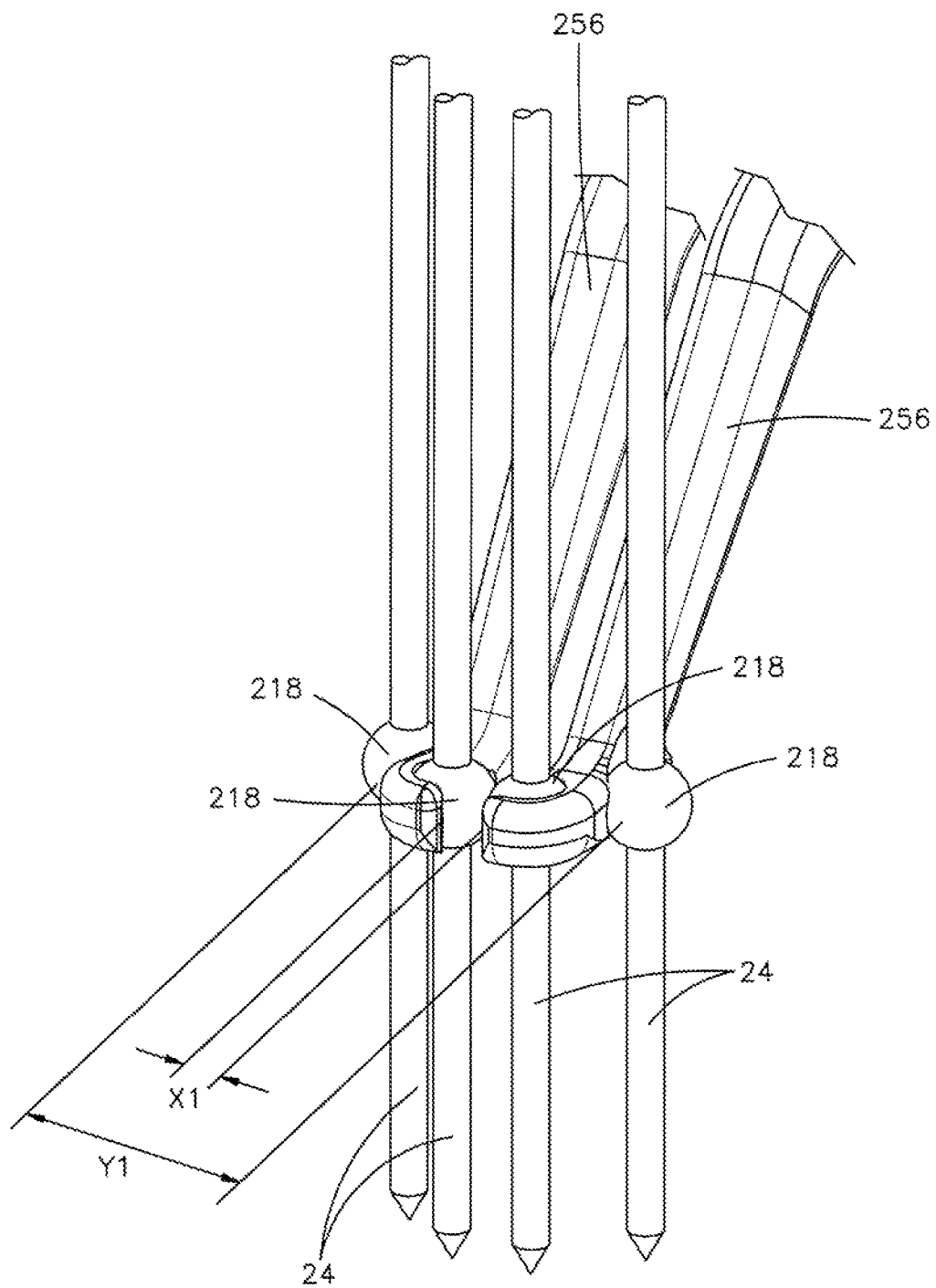
FIG. 8B is a perspective view of the distal end illustrated in FIG. 8A, schematically showing the compression and distraction engagement members operatively coupled to respective K-wires.
Figure 8D:
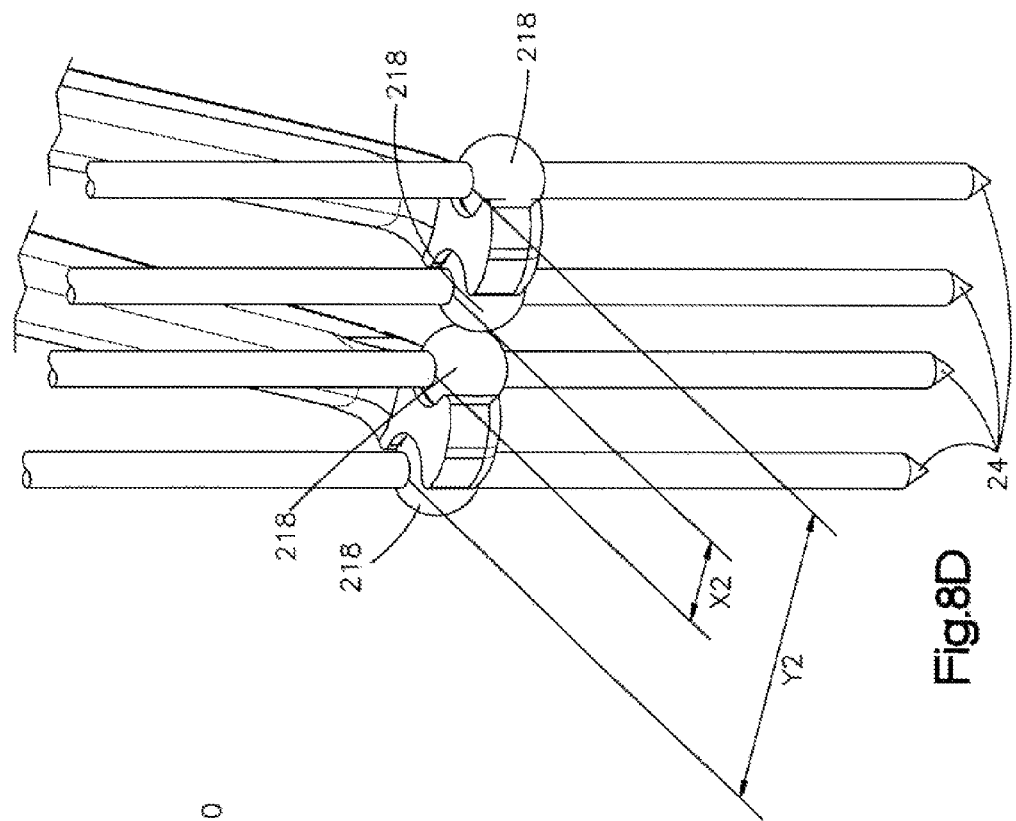
FIG. 8D is a perspective view of the distal end illustrated in FIG. 8C, schematically showing the compression and distraction engagement members operatively coupled to respective K-wires.
Figure 8C:
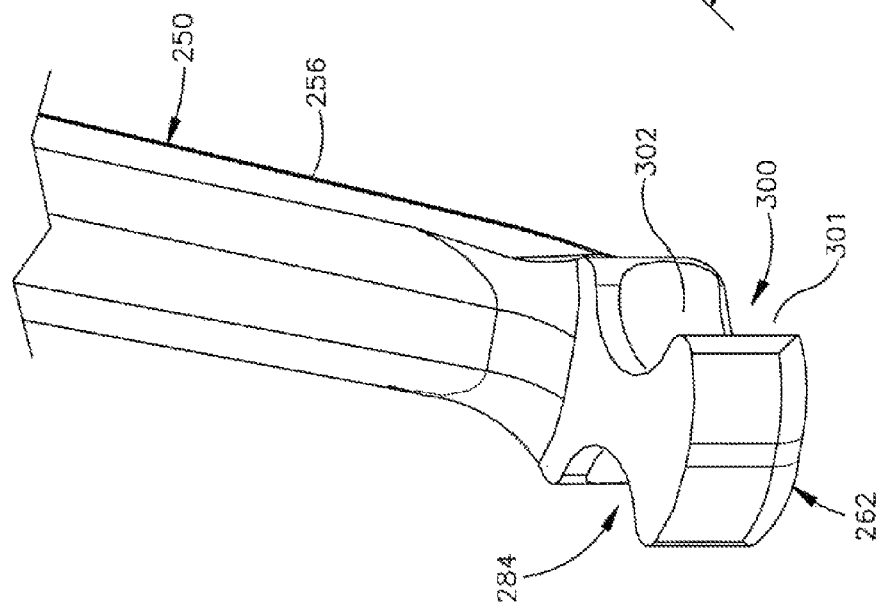
FIG. 8C is an enlarged perspective view of a distal end of one arm of the forceps illustrated in FIG. 7A, but constructed in accordance with an alternative embodiment, including a compression and distraction engagement members.

Referring now to FIGS. 8C-D, the outer pocket 300 can be substantially aligned with the inner pocket 284 with respect to the first and second directions of travel. Thus, the engagement members 218 of the K-wires 24 can be brought together to a minimum retracted distance of X1, which is achieved when the engagement members 218 are received in the pockets 284 and abut each other. The handles 258 can be brought together so that the pockets 300 are separated a distance equal to or greater than Y2, which is the minimum distance achievable between the pockets 300 when engagement members 218 are disposed in the inner pockets 284, it being appreciated that the minimum distance Y2 can be reduced further when engagement members 218 are not disposed in the pockets 284. Because the pockets 300 and substantially aligned with the pockets 284, the distance Y2 is greater than the distance Y1, which is achieved when the pockets 300 and the pockets 284 are offset with respect to the first and second directions of travel.

Referring now to FIGS. 8E-F, the engagement member 262 is illustrated in accordance with an alternative embodiment as a forked engagement member that defines a opposed inner and outer arms 350 and 352, respectively, that define a gap 354 therebetween. The gap 354 is sized to receive the engagement member 282. The inner arm 350 defines a first surface 356 that faces the gap 354, and an opposed outer surface 358 that faces the inner arm 352 of the other arm of the forceps 26. The outer arm 352 likewise defines a first surface 360 that faces the gap 354, and an opposed outer surface 362. The engagement member 262 includes the reduction pocket 284 formed in the first surface 360 at the distal portion of the outer arm 352, and the distraction pocket 300 formed in the first surface 356 at the distal portion of the inner arm 350. Thus, the reduction pocket 284 and the distraction pocket 300 face each other. The pockets 300 are illustrated as at least partially aligned with the pockets 284 along the first and second directions of travel.

During operation, the engagement members 218 of the K-wires 24 is received in the respective gaps 354, and the engagement members 262 can be brought together, thereby causing the engagement members 218 to be received in the reduction pockets 284. As the engagement members 262 are brought together, at least one of the engagement members 218 to translate toward the other so as to reduce the bone gap 28 in the manner described above to a minimum distance of X3, which can be greater than, less than, or equal to X1 and X2, depending on the thickness of the arms 350 and the engagement member 218. The engagement members 262 can also be brought away from each other from a minimum separation distance of Y3, which can be greater than, equal to, or less than Y1 and Y2, depending on the dimensions of the engagement members 262 and the engagement member 218.

Figure 10:
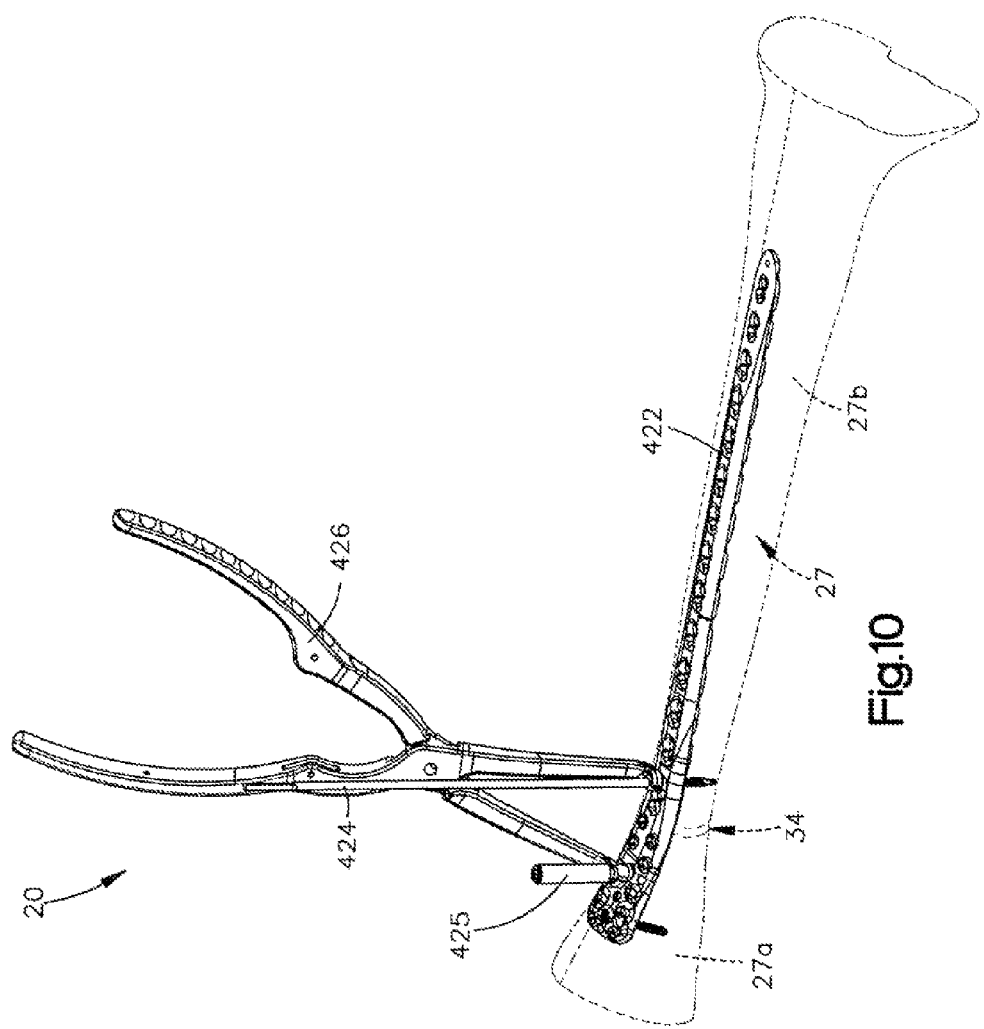
FIG. 10 is a perspective view of a bone fixation system constructed in accordance with an alternative embodiment operatively coupled to a pair of schematically illustrated bone segments separated by a bone gap, the bone fixation system including a bone fixation plate, a K-wire, a post, and a forceps.

Referring now to FIG. 10, the bone fixation system 20 can also include a bone fixation plate 422, a temporary fixation member illustrated as a K-wire 424, a second temporary fixation member illustrated as a post 425, and a forceps 426 configured to engage the K-wire 424 and the post 425. The bone fixation plate 422 is placed against or in proximity with the underlying bone 27 and is affixed to the first bone segment 27a with a bone anchor. The K-wire 424 is inserted through the plate 422 and into the second bone segment 27b, the post 425 is fixedly coupled to the bone plate 422 adjacent the first bone segment, and the forceps 426 can apply a force onto the K-wire 424 and the post 425 so as to translate at least one of or both of the bone segments 27a and 27b, thereby adjusting the relative positions of the bone segments 27a and 27b in relation to each other.

Referring to FIGS. 11A and 11B, an alternatively constructed bone fixation plate 422 includes a plate body 432 that extends substantially along a central longitudinal axis 431, and defines a proximal end 434 and a distal end 436 opposite the proximal end 434 along the longitudinal axis 431. The plate body 432 further includes a bone-facing inner surface 438 and an opposed outer surface 440 spaced from the inner surface 438 along the transverse direction T. The plate body 432 further defines opposed side surfaces 442 and 444 that are spaced from each other along the lateral direction A. The plate body 432 includes a head portion 446 at the distal end 436 that can be configured and dimensioned to conform to the contour of the near cortex of the underlying bone 27, and a shaft portion 448 connected to the head portion 446 and disposed longitudinally proximal from the head portion 446. The shaft portion 448 can be configured and dimensioned to conform to the contour of the near cortex of the underlying bone 27.

With continuing reference to FIGS. 11A and 11B, the bone plate 422 includes a plurality of apertures 439 that extend transversely through the plate body 432, from the bone-facing inner surface 438 through to the outer surface 440. As shown, the apertures 439 include a plurality of bone anchor holes 441, and a post receiving hole 443. In particular the head portion 446 includes a plurality of variable angle holes 452, and the shaft portion 448 includes a plurality of combination holes 457 that include a variable angle hole portion combined with a fixed angle hole portion. As shown, at least one of the combination holes 457 includes an elongated fixed angle hole portion 458 that is configured to receive the K-wire 424. It should be understood, however, that the bone plate 422 may include apertures 439 having other configuration. For example, at least some of the apertures 439 may be configured as a compression hole, a threaded locking hole, or a combination of both or any other configuration as desired. Furthermore, the head portion 446 and the shaft portion 448 may include any of the apertures as desired.

As shown in FIG. 11B, the post receiving hole 443 extends through the head portion 446 of the bone plate 422. The post receiving hole 443 includes a coupler 460, such as threads 461 that are configured to engage threads defined by the post 425 to thereby fixedly couple the post 425 to the bone plate 422. It should be understood, however, that the coupler 460 may include configurations other than threads 461, so long as the post 425 can be fixedly coupled to the bone plate 422. For example, the coupler 460 may define a tapered interior surface that is configured as a snap on mount. Furthermore, the post receiving hole 443 may be located anywhere along the bone plate 422. In particular, a dedicated post receiving hole 443 may be positioned at other locations on the plate 422 as desired. Alternatively, one of the bone anchor holes 441 or combination holes 457 may be configured to receive the post 425 to thereby define a post receiving hole 443.

As shown in FIG. 11B, the combination hole 457 that includes the elongated fixed angle hole portion 458 is configured to receive the K-wire 424 such that the K-wire 424 can translate within the elongated fixed angle hole portion 458. In this way, the elongated fixed angle hole portion 58 may be considered a K-wire slot 564. As shown, the K-wire slot 564 includes a lateral dimension, and a longitudinal dimension that is greater than the lateral dimension to allow the K-wire 424 to translate in the longitudinal direction. While the elongated fixed angle hole portion 58 is illustrated as being combined with a variable angle hole, it should be understood that the elongated fixed angle hole portion 58 may be a stand alone fixed angle hole that is not combined with a variable angle hole.

Now referring to FIGS. 12A and 12B, in an alternative embodiment, the K-wire 424 provides a temporary fixation member having a wire body 512 that is longitudinally elongate along a central axis 513. The K-wire 424 can be referred to as temporary fixation member, a temporary bone anchor or a temporary bone fixation member, as it is driven into the underlying bone 27 and subsequently removed prior to completion of the surgical or bone fixation procedure. The wire body 512 defines a proximal portion 514 and an opposing distal portion 516 that is spaced from the proximal portion 514 along the central axis 513. The K-wire 424 includes a first engagement member 518 and a second engagement member 519 that are attached to the wire body 512 and separate the distal portion 516 from the proximal portion 514. The proximal and distal portions 514 and 516 can be cylindrical in shape or can define any suitable alternative shape as desired. The engagement members 518 and 519 each define an outer engagement surface 520 that can be spherical as illustrated, or can define any suitable alternative shape. For instance, the outer surfaces 520 can be round (for instance cylindrical or otherwise curved), polygonal, or the like, and thus suitable to be engaged by the forceps.

The proximal portion 514 of the K-wire is configured to be engaged by an insertion tool so as to be rotatably driven. The distal portion 516 of the K-wire 424 is configured to be inserted through an aperture 439 of the bone plate 422, and temporarily driven into and thus fixed to the underlying bone 27. In particular, the K-wire 424 includes helical threads 522 at the distal portion 516 and a tapered or pointed driving end or tip 524 that can present one or more cutting flutes as desired such that the K-wire 424 can be self-tapping. The tip 524 is thus configured to be driven into an underlying bone to a depth such that rotation of the K-wire 424 causes the threads 522 to drive into the bone 27. The threads 522 extend along all or a region of the distal portion 516, for instance from a location proximate to the tip 524 a location proximate to the second engagement member 519. The threads 522 can extend to the second engagement member 519, or can terminate at a location spaced distally from the second engagement member 519.

With continuing reference to FIG. 12B, the first engagement member 518 can include an outer surface 520 that is spherical as illustrated, but can have any shape suitable for receiving a force that biases the K-wire 424 and the underlying bone in a desired direction as defined by the bone plate aperture 458 through which the distal portion 516 extends. For instance, the outer surface 520 can be cylindrical in shape about the central axis 513, or about any axis coincident with or intersecting the central axis 513. In this regard, the outer surface 520 can define a circular cross-section, an oval cross-section, or any alternative curved or polygonal shape, regular or irregular, in cross-section. Accordingly, the outer surface 520 can define a curved surface in any direction as desired, or can be polygonal, regular or irregular, angled, or can define any alternative shape as desired. The spherical outer surface 520 allows the forceps to engage the engagement member 518 at variable approach angles. The engagement member 518 can be integrally or discretely attached (e.g., welded) to the wire body 512.

Similarly the second engagement member 519 is positioned distal to the first engagement member 518 and can include an outer surface 520b that is spherical as illustrated, but can have any shape suitable for at least one of receiving a force that biases the K-wire 424 and providing a surface to rest within the elongated fixed angle portion 458 through which the K-wire 424 extends. For instance, the outer surface 520b can be cylindrical in shape about the central axis 513, or about any axis coincident with or intersecting the central axis 513. In this regard, the outer surface 520b can define a circular cross-section, an oval cross-section, or any alternative curved or polygonal shape, regular or irregular, in cross-section. Accordingly, the outer surface 520b can define a curved surface in any direction as desired, or can be polygonal, regular or irregular, angled, or can define any alternative shape as desired. The second engagement member 519 can be integrally or discretely attached (e.g., welded) to the wire body 512.

When the K-wire 424 is to be inserted into the elongated fixed axis hole 458 of the combination hole 457, the outer surface 520b of the second engagement member 519 will abut the bone plate 422 so as to limit the insertion depth of the K-wire 424 into the underlying bone 27. Because the elongated fixed axis portion 458 is recessed, the second engagement member 519 will be recessed within the elongated fixed axis portion 458 thereby positioning the first engagement member 518 to be engaged by the forceps. As shown the second engagement member 519 is distal to and proximate to the first engagement member 518. In the illustrated embodiment the second engagement member 519 abuts the first engagement member 518, though it should be understood that the first and second engagement members 518 and 519 may be spaced along the K-wire body 512. Additionally, if the K-wire 424 is inserted through a hole such as slot 45 of the bone plate 22 shown in FIG. 2A, the outer surface 520b of the second engagement member 519 will not only abut the bone plate 22, but will also be engaged by the forceps.

Referring to FIGS. 13A and 13B, the post 425 provides a temporary fixation member having a post body 612 that is longitudinally elongate along a central axis 613. The post 425 can be referred to as temporary fixation member, or a temporary plate fixation member, as it is fixedly coupled to the plate 422 and subsequently removed prior to completion of the surgical or bone fixation procedure. The post body 612 defines a proximal portion 614 and an opposing distal portion 616 that is spaced from the proximal portion 614 along the central axis 613. The post 425 includes an engagement member 618 that is attached to the post body 612 and separates the distal portion 616 from the proximal portion 614. The proximal and distal portions 614 and 616 can be cylindrical in shape or can define any suitable alternative shape as desired. The engagement member 618 can define an outer engagement surface 620 that can be spherical as illustrated, or can define any suitable alternative shape. For instance, the outer surface 620 can be round (for instance cylindrical or otherwise curved), polygonal, or the like, and thus suitable to be engaged by the forceps.

The proximal portion 614 of the post 425 is configured to be engaged by an insertion tool so as to be rotatably driven. The distal portion 616 of the post 425 is configured to be inserted into the post receiving hole 443 of the bone plate 422, and temporarily fixedly coupled to the bone plate 422. In particular, the post 425 includes a coupler such as helical threads 622 at the distal portion 616 that are configured to engage the internal threads 461 defined by the post receiving hole 443 of the bone plate 422. In the illustrated embodiment the distal portion 616 tapers, though it should be understood that the distal portion 616 may include other configurations as desired.

With continuing reference to FIG. 13B, the engagement member 618 can include an outer surface 620 that is spherical as illustrated, but can have any shape suitable for receiving a force that biases the post 425. For instance, the outer surface 620 can be cylindrical in shape about the central axis 613, or about any axis coincident with or intersecting the central axis 613. In this regard, the outer surface 620 can define a circular cross-section, an oval cross-section, or any alternative curved or polygonal shape, regular or irregular, in cross-section. Accordingly, the outer surface 620 can define a curved surface in any direction as desired, or can be polygonal, regular or irregular, angled, or can define any alternative shape as desired. The spherical outer surface 620 allows the forceps to engage the engagement member 618 at variable approach angles. The engagement member 618 can be integrally or discretely attached (e.g., welded) to the post body 612.

When the post 425 is to be inserted into the post receiving hole 443 of the bone plate 422, the outer surface 620 of the engagement member 618 will abut the bone plate 422. At this point the post 425 will be fixedly coupled to the bone plate 422, and the outer surface 620 of the engagement member 618 will be positioned to be engaged by the forceps along with the first engagement member 518 of the K-wire 424.

Referring to FIGS. 14A and 14B, the forceps 426 may be configured as compression forceps 426a as shown in FIG. 14A or as distraction forceps 426b as shown in FIG. 14B. As shown in FIGS. 14A and 14B, the forceps 426 include a pair of arms 650 pivotally connected together at a joint 652, which divide the arms 650 between a proximal portion 654 and an opposing distal portion 656. The proximal portion 654 is similar to the proximal portion 254 of the forceps 26 shown in FIG. 7C. The distal portions 656 of the forceps 426 extend substantially perpendicularly from the bone plate when the forceps 426 are in use. Such a configuration allows for an above approach to the bone plate 422 with the forceps 426. Like the forceps 26, the distal portion 656 of each arm 650 of the forceps 426 defines an engagement member 662 that is configured to engage the outer surfaces 520 and 620 of the K-wire 424 and the post 425 respectively.

Referring to FIG. 14A, the forceps 426a are configured for compression. Therefore as the proximal portions 654 of the arms 650 are brought together, the engagement members 662 are likewise brought together, and when the proximal portions 654 are moved apart, the engagement members 662 are likewise moved apart. As shown in FIG. 14A, each engagement member 662 defines an inner engagement surface 680 that faces the corresponding inner engagement surface 680 of the other arm 650, and an opposing outer surface 682. When the engagement members 662 each engage a complementary engagement member 518 or 618 of the K-wire 424 and the post 425, the inner surfaces 680 can abut the respective outer surfaces 520 and 620 of the engagement members 518 and 618 respectively.

In accordance with the illustrated embodiment, each engagement member 662 includes a pocket 684 that projects into the inner surface 680. The pockets 684 are configured to receive the engagement members 518 and 618 of the K-wire 424 and the post 425 respectively.

Now referring to FIG. 14B, the forceps 426b are configured for distraction. Therefore as the proximal portions 654 of the arms 650 are brought together, the engagement members 662 are conversely moved away from each other, and when the proximal portions 654 are moved apart, the engagement members 662 are conversely brought together. As shown in FIG. 14B, each engagement member 662 defines an outer engagement surface 780 that faces away from the corresponding engagement surface 780 of the other arm 650, and an opposing inner surface 782. When the engagement members 662 each engage a complementary engagement member 518 or 618 of the K-wire 424 and the post 425, the inner surfaces 780 can abut the respective outer surfaces 520 and 620 of the engagement members 518 and 618 respectively.

In accordance with the illustrated embodiment, each engagement member 662 of the forceps 426b includes a pocket 784 that projects into the outer surface 780. The pockets 784 are configured to receive the engagement members 518 and 618 of the K-wire 424 and the post 425 respectively.

It should be understood that the forceps 426, the bone plate 422, the K-wire 424, and the post 425 may be alternatively configured to include any of the features of the previously described forceps, bone plates, and K-wires. Therefore for example, the forceps 426 may include arms defining internal and external engagement surfaces as shown in FIG. 8B or 8C, or arms with front loading pockets as shown in FIG. 8E. Similarly, the bone plate 422 may include alternative shapes, apertures, and configurations as desired, the K-wire 424 and the post 425 may include features described in conjunction with the K-wires 24 shown in FIGS. 6A and 6B.

Now referring to FIGS. 15A-17B, the bone fixation system 20 shown in FIG. 10 may be configured in a variety ways to move the bone segments relative to each other. For example, the system 20 may be configured to compress the bone segments using the forceps 426a, distract the bone segments using the forceps 426a, compress the bone segments using the forceps 426b, and/or distract the bone segments using the forceps 426b depending on the positions of the K-wire 424 and the post 425.

Figure 15A:
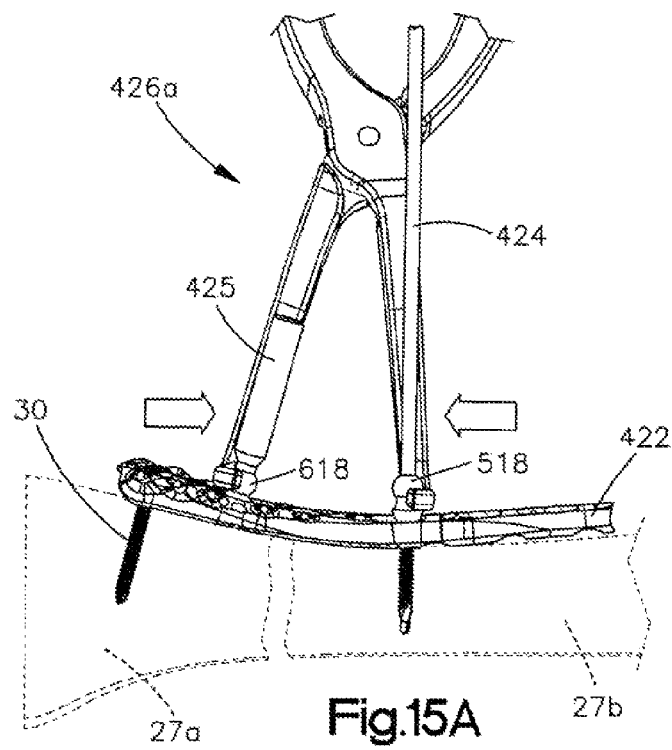
FIG. 15A is a front perspective view of the bone fixation system illustrated in FIG. 10 reducing the bone gap defined between the first and second bone segments, the bone fixation plate affixed to the first bone segment with a bone anchor, the post fixedly coupled to the bone fixation plate adjacent the first bone segment, and the K-wire extending through the bone plate and into the second bone segment.

As shown in FIG. 15A, in one configuration the bone plate 422 may be affixed to the first bone segment 27a with a bone anchor 30, the post 425 is fixedly coupled to the bone plate 422 adjacent the first bone segment 27a, and the K-wire 424 extends through the bone plate 422 and into the second bone segment 27b. In particular the post 425 is fixedly coupled to the post receiving hole 443 and the K-wire 424 extends through the elongated fixed angle hole 458. The forceps 426a may then be positioned such that the engagement members 520 and 620 of the K-wire 424 and the post 425 are received by the pockets 684 defined by the engagement members 662. By compressing or otherwise actuating the forceps 426a, the engagement members 662 are biased toward each other and at least one of the first bone segment 27a and the second bone segment 27b moves toward the other to thereby reduce the bone gap defined between the bone segments. In this configuration and with the forceps 426a, the first and second bone segments are pulled toward each other by the biasing forces against the K-wire 424 and the post 425.

Figure 15B:
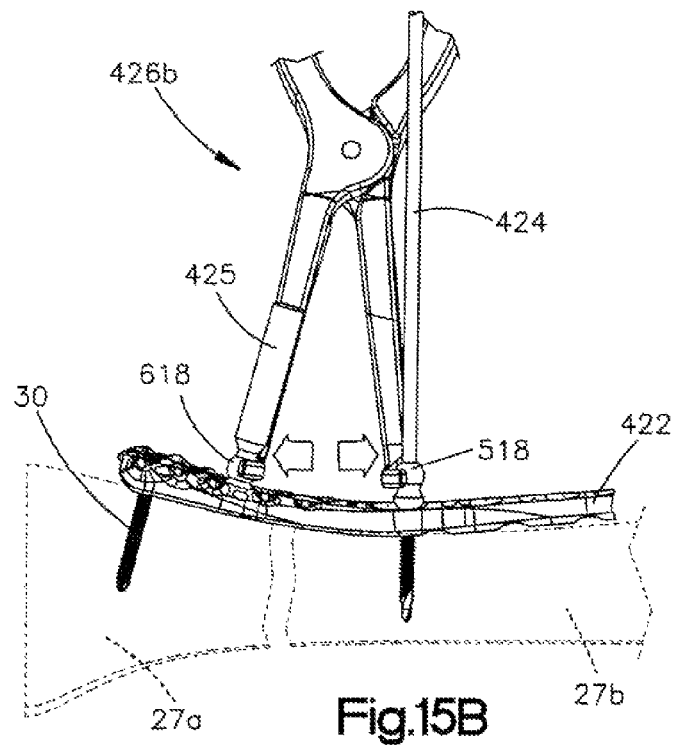
FIG. 15B is a front perspective view of the bone fixation system illustrated in FIG. 15A distracting the bone gap defined between the first and second bone segments with the forceps illustrated in FIG. 14B.

Alternatively, the bone segments 27a and 27b may be moved away from each other or otherwise distracted if forceps 426b are used. As shown in FIG. 15B, the forceps 426b may be positioned such that the engagement members 520 and 620 of the K-wire 424 and the post 425 are received by the pockets 784 defined by the engagement members 662 of the forceps 426b. By distracting or otherwise actuating the forceps 426b, the engagement members 662 are biased away from each other and at least one of the first bone segment 27a and the second bone segment 27b moves away from the other to thereby distract the bone gap defined between the bone segments. In this configuration and with the forceps 426b, the first and second bone segments are pushed away from each other by the biasing forces against the K-wire 424 and the post 425.

Figure 16A:
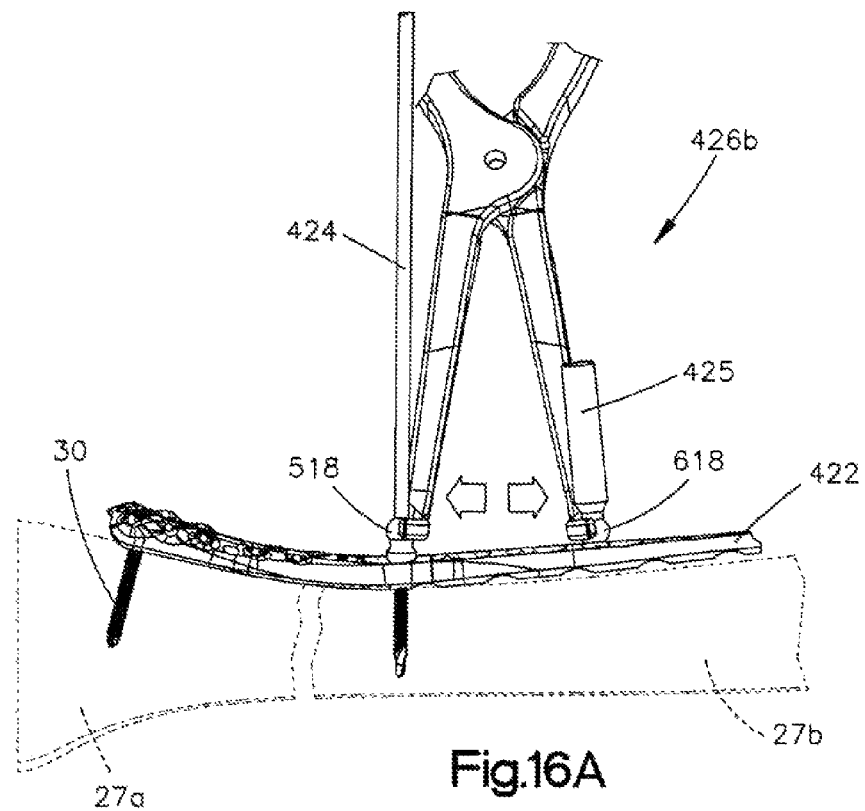
FIG. 16A is a front perspective view of the bone fixation system illustrated in FIG. 10 compressing the bone gap defined between the first and second bone segments, the bone fixation plate affixed to the first bone segment with a bone anchor, the K-wire extending through the bone plate and into the second bone segment, and the post fixedly coupled to the bone plate adjacent the second bone segment such that distraction of the forceps causes the bone gap to compress.

In another configuration and in reference to FIG. 16A, the bone plate 422 may be affixed to the first bone segment 27a with a bone anchor 30, the post 425 is fixedly coupled to the bone plate 422 adjacent the second bone segment 27b, and the K-wire 424 extends through the bone plate 422 and into the second bone segment 27b at a location closer to the bone gap than the post 425. In particular the post 425 is fixedly coupled to a variable angle hole that defines a post receiving hole 443, and the K-wire 424 extends through the elongated fixed angle hole 458. The forceps 426b may then be positioned such that the engagement members 520 and 620 of the K-wire 424 and the post 425 are received by the pockets 784 defined by the engagement members 662. By distracting or otherwise actuating the forceps 426b, the engagement members 662 are biased away from each other and at least one of the first bone segment 27a and the second bone segment 27b moves toward the other to thereby reduce the bone gap defined between the bone segments. In this configuration and with the forceps 424b, the first bone segment 27a is pulled by the biasing force against the post 425, and the second bone segment 27b is pushed by the biasing force against the K-wire 424.

Figure 16B:
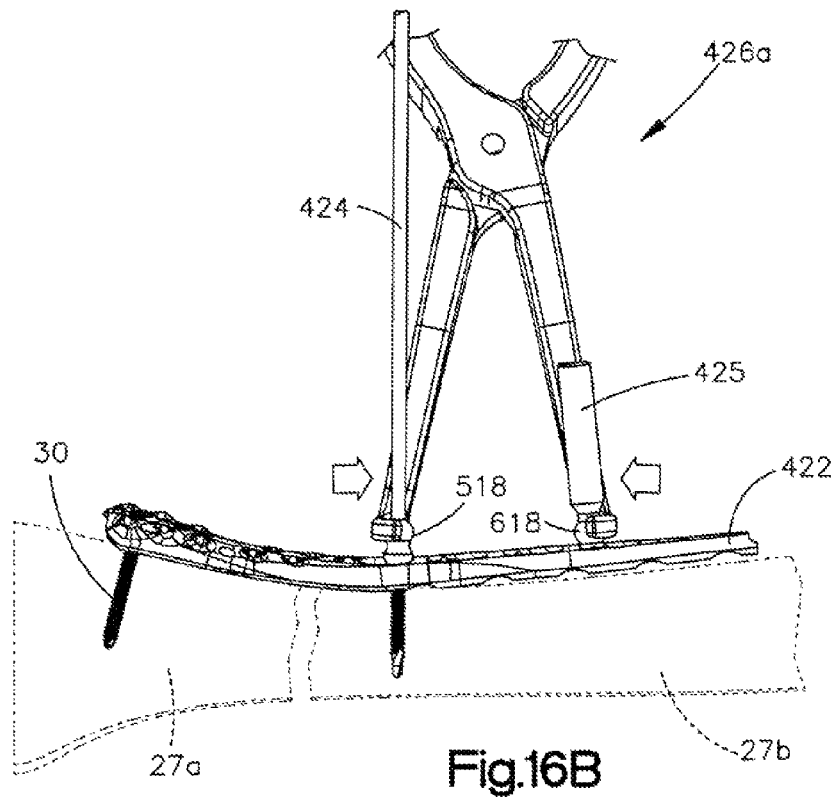
FIG. 16B is a front perspective view of the bone fixation system illustrated in FIG. 16A distracting the bone gap defined between the first and second bone segments with the forceps illustrated in FIG. 14A.

Alternatively, the bone segments 27a and 27b may be moved away from each other or otherwise distracted if forceps 426a are used. As shown in FIG. 16B, the forceps 426a may be positioned such that the engagement members 520 and 620 of the K-wire 424 and the post 425 are received by the pockets 684 defined by the engagement members 662 of the forceps 426a. By compressing or otherwise actuating the forceps 426a, the engagement members 662 are biased toward each other and at least one of the first bone segment 27a and the second bone segment 27b moves away from the other to thereby distract the bone gap defined between the bone segments. In this configuration and with the forceps 426a, the first bone segment 27a is pushed by the biasing force against the post 425, and the second bone segment 27b is pulled by the biasing force against the K-wire 424.

Figure 17A:
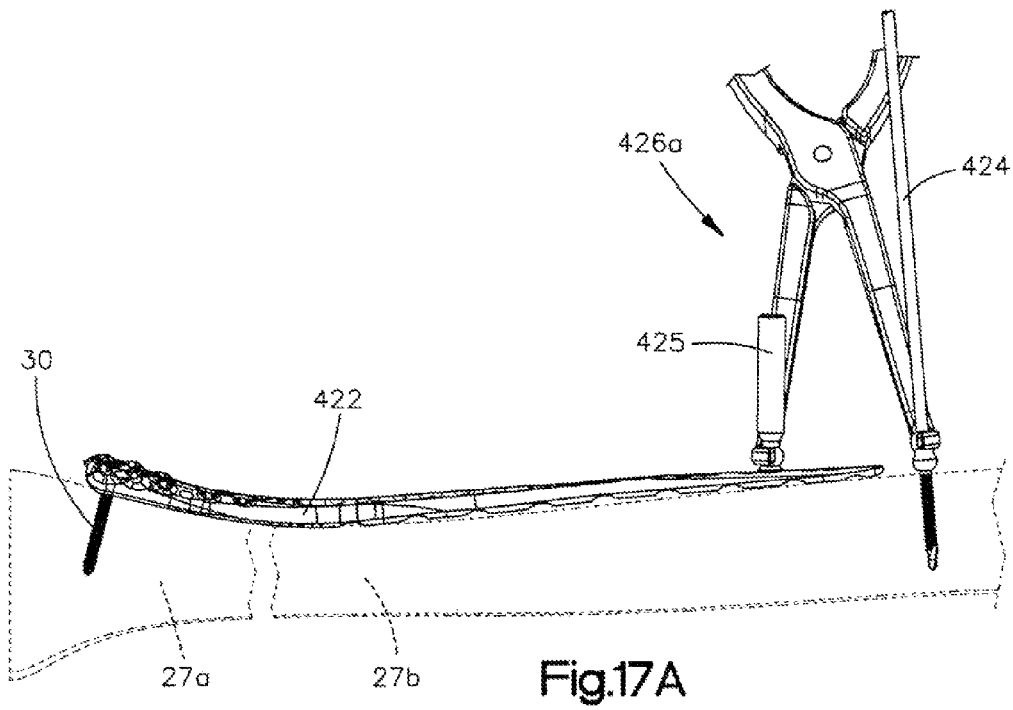
FIG. 17A is a front perspective view of the bone fixation system illustrated in FIG. 10 compressing the bone gap defined between the first and second bone segments, the bone fixation plate affixed to the first bone segment with a bone anchor, the K-wire extending directly into the second bone segment, and the post fixedly coupled to the bone plate adjacent the second bone segment such that compression of the forceps causes the bone gap to compress.

In another configuration and in reference to FIG. 17A, the bone plate 422 may be affixed to the first bone segment 27a with a bone anchor 30, the post 425 is fixedly coupled to the bone plate 422 adjacent the second bone segment 27b, and the K-wire 424 extends directly into the second bone segment 27b at a location further from the bone gap than the post 425. In particular the post 425 is fixedly coupled to a variable angle hole that defines a post receiving hole 443, and the K-wire 424 extends into the second bone segment 27b without passing through the bone plate 422. The forceps 426a may then be positioned such that the engagement members 520 and 620 of the K-wire 424 and the post 425 are received by the pockets 684 defined by the engagement members 662. By compressing or otherwise actuating the forceps 426a, the engagement members 662 are biased toward each other and at least one of the first bone segment 27a and the second bone segment 27b moves toward the other to thereby reduce the bone gap defined between the bone segments. In this configuration and with the forceps 424a, the first bone segment 27a is pulled by the biasing force against the post 425, and the second bone segment 27b is pushed by the biasing force against the K-wire 424.

Figure 17B:
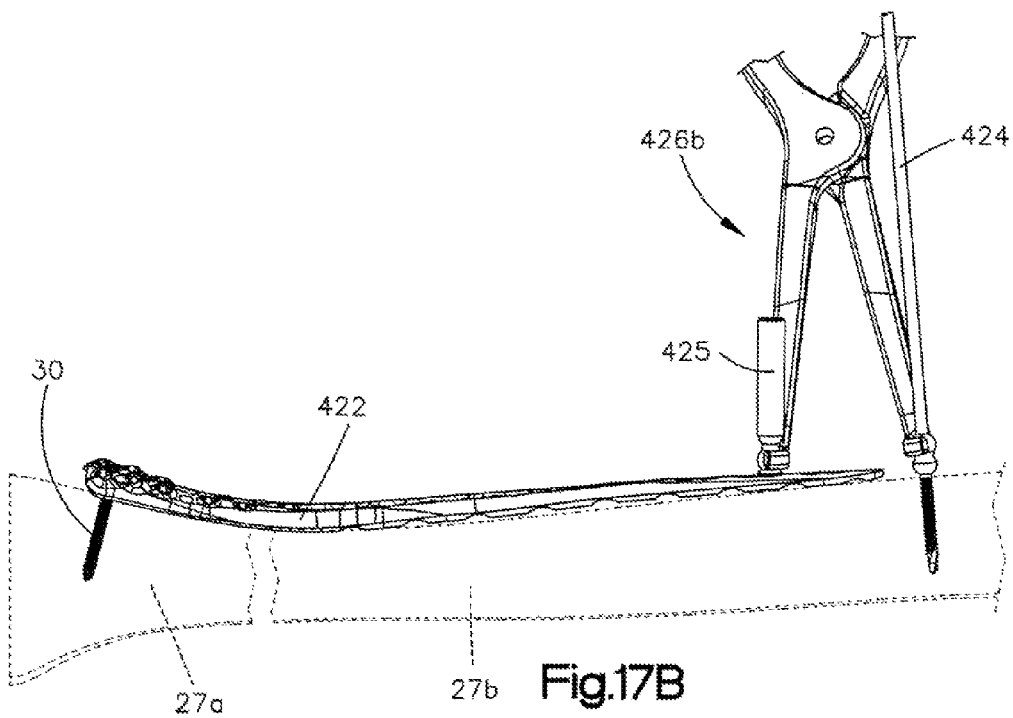
FIG. 17B is a front perspective view of the bone fixation system illustrated in FIG. 17A distracting the bone gap defined between the first and second bone segments with the forceps illustrated in FIG. 14B.

Alternatively, the bone segments 27a and 27b may be moved away from each other or otherwise distracted if forceps 426b are used. As shown in FIG. 17B, the forceps 426b may be positioned such that the engagement members 520 and 620 of the K-wire 424 and the post 425 are received by the pockets 784 defined by the engagement members 662 of the forceps 426b. By distracting or otherwise actuating the forceps 426b, the engagement members 662 are biased away from each other and at least one of the first bone segment 27a and the second bone segment 27b moves away from the other to thereby distract the bone gap defined between the bone segments. In this configuration and with the forceps 426b, the first bone segment 27a is pushed by the biasing force against the post 425, and the second bone segment 27b is pulled by the biasing force against the K-wire 424.

It should be appreciated that a bone fixation kit can be provided that includes at one or more, up to all, of the components of the bone fixation system 20, including but not limited to one or more bone fixation plates that can be sized and shaped the same or differently, a plurality of guide wires that can be sized and shaped the same or differently, a plurality of bone anchors configured the same or differently, and one or more forceps configured the same or differently. It should be appreciated that the components of the bone kit can be provided as described above with respect to the various embodiments and alternative embodiments. Furthermore, the components of the kit can be sold contemporaneously in a common packaging, or at different times in different packaging.

It should be appreciated that the methods described herein can include the steps of inserting the K-wires into the underlying bone segments 27a-b without first placing a bone fixation plate over the bone segments, such that the forceps can actuate the K-wires in the manner described herein to adjust the underlying bone segments 27a-b from a first relative position to a second different relative position. In this regard, the bone fixation kit described above can include one or more bone fixation plates as desired, or can be devoid of bone fixation plates.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein, unless otherwise indicated. Accordingly, those skilled in the art will realize that the invention is intended to encompass all modifications and alternative arrangements included within the spirit and scope of the invention, for instance as set forth by the appended claims.

The invention claimed is:

1. A forceps configured to apply a biasing force to a pair of temporary fixation members, each temporary fixation member having a distal portion and an engagement member disposed proximal of the distal portion, the engagement member defining a dimension greater than that of the distal portion, the forceps comprising:
   a pair of arms, each arm having:
      a proximal end and an opposed distal end;
      an arm engagement member defining a first pocket that extends into the distal end such that the first pocket defines a channel that extends through the distal end along a vertical direction, the first pocket further defining an engagement surface that defines a horizontal radius of curvature swept along a horizontal direction and a vertical radius of curvature swept along the vertical direction, the horizontal radius of curvature being equal to or greater than the vertical radius of curvature;
   wherein relative movement of the arms causes the distal ends to correspondingly move, such that each first pocket at least partially receives a respective one of the temporary fixation members and each engagement surface applies a biasing force against the engagement member of respective one of the temporary fixation members.

2. The forceps as recited in claim 1, wherein the first pockets of each arm face each other, such that the engagement surfaces are configured to apply a compressive force to the engagement members of the respective temporary fixation members when the distal ends are brought together.

3. The forceps as recited in claim 2, wherein each arm further comprises a second pocket at the distal end such that the first and second pockets of each arm face away from each other, each second pocket defining an engagement surface having a shape corresponding to that of the engagement member of the temporary fixation member such that the engagement surfaces are configured to apply a distractive force to the engagement members of the respective temporary fixation members when the distal ends are brought apart.

4. The forceps as recited in claim 3, wherein the second pocket of each arm is aligned with the first pocket along a direction that is perpendicular to the vertical direction.

5. The forceps as recited in claim 3, wherein the second pocket of each arm is offset with respect to the first pocket.

6. The forceps as recited in claim 3, wherein each arm engagement member of the forceps is forked and comprises first and second arms that define a gap therebetween, the gap sized to receive the engagement member of the temporary fixation member.

7. The forceps as recited in claim 1, wherein the first pockets face toward each other, such that the engagement surfaces are configured to apply a compressive force to the engagement members of the respective temporary fixation members when the distal ends are brought together.

8. The forceps as recited in claim 1, wherein the handles are pivotally coupled.

9. The forceps as recited in claim 8, wherein the distal ends are moved closer together as the handles are moved closer together.

10. The forceps as recited in claim 8, wherein the distal ends are moved farther apart as the handles are moved farther apart.

11. The forceps as recited in claim 1, further comprising a ratchet connected between the arms and configured to incrementally move the arms when a force is applied to the arms.

12. The forceps as recited in claim 1, wherein the engagement surface conforms to the engagement member of the temporary fixation member along at least one direction.

13. The forceps as recited in claim 12, wherein the engagement surface is circular in the direction.

14. The forceps as recited in claim 1, wherein the each temporary fixation member is a K-wire configured to engage one of the bone segments.

15. The forceps as recited in claim 1, wherein one of the temporary fixation members is a K-wire configured to engage one of the bone segments, and the other one of the temporary fixation members is a post configured to engage a bone plate.

16. The forceps as recited in claim 3, wherein the second pockets each define a second engagement surface having a horizontal radius of curvature and a vertical radius of curvature.

17. A forceps configured to apply a biasing force to a pair of temporary fixation members, each temporary fixation member having a distal portion and an engagement member disposed proximal of the distal portion, the engagement member defining a dimension greater than that of the distal portion, the forceps comprising:
   a pair of arms, each arm having:
      a proximal end and an opposed distal end;
      an arm engagement member defining a first pocket that extends into the distal end and a second pocket that extends into the distal end such that the first and second pockets face away from each other, the first and second pockets each defining a respective engagement surface that defines a horizontal radius of curvature and a vertical radius of curvature;
   wherein (i) a first relative movement of the arms causes the distal ends to correspondingly move, such that each first pocket at least partially receives a respective one of the temporary fixation members such that the engagement surfaces of the first pockets apply a compressive force to the engagement members of the temporary fixation members, and (ii) a second relative movement of the arms causes the distal ends to correspondingly move, such that each second pocket at least partially receives a respective one of the temporary fixation members such that the engagement surfaces of the second pockets apply a distractive force to the engagement members of the temporary fixation members.

18. The forceps as recited in claim 17, wherein the temporary fixation members are configured to extend through the distal ends along a first direction and wherein the second pocket of each arm is aligned with the first pocket along a direction that is perpendicular to the first direction.

19. The forceps as recited in claim 17, wherein the second pocket of each arm is offset with respect to the first pocket.

20. The forceps as recited in claim 17, wherein the horizontal radius of curvature is swept along a horizontal direction and the vertical radius of curvature is swept along a vertical direction.

* * * * *